(12) United States Patent
Berger et al.

(10) Patent No.: US 8,501,786 B2
(45) Date of Patent: Aug. 6, 2013

(54) HYDROXYMETHYL PYRROLIDINES AS BETA 3 ADRENERGIC RECEPTOR AGONISTS

(75) Inventors: Richard Berger, Princeton, NJ (US); Lehua Chang, Ramsey, NJ (US); Scott D. Edmondson, Clark, NJ (US); Stephen D. Goble, Edison, NJ (US); Bart Harper, New York, NY (US); Nam Fung Kar, Brooklyn, NY (US); Ihor E. Kopka, Hampton, NJ (US); Bing Li, Towaco, NJ (US); Gregori J. Morriello, Randolph, NJ (US); Chris R. Moyes, Westfield, NJ (US); Dong-Ming Shen, Edison, NJ (US); Liping Wang, Dayton, NJ (US); Harvey Wendt, Medford Lakes, NJ (US); Cheng Zhu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 206 days.

(21) Appl. No.: 12/936,275

(22) PCT Filed: Mar. 23, 2009

(86) PCT No.: PCT/US2009/037911
§ 371 (c)(1),
(2), (4) Date: Oct. 4, 2010

(87) PCT Pub. No.: WO2009/123870
PCT Pub. Date: Oct. 8, 2009

(65) Prior Publication Data
US 2011/0028461 A1    Feb. 3, 2011

(51) Int. Cl.
| | | |
|---|---|---|
| A61K 31/443 | (2006.01) |
| A61K 31/4436 | (2006.01) |
| A61K 31/4439 | (2006.01) |
| C07D 401/14 | (2006.01) |
| C07D 413/14 | (2006.01) |
| C07D 417/14 | (2006.01) |

(52) U.S. Cl.
USPC ......... 514/340; 514/336; 514/341; 514/342; 546/269.1; 546/271.4; 546/272.4; 546/268.4; 546/272.7; 546/275.4; 546/276.4

(58) Field of Classification Search
USPC .......... 546/269.1, 271.4, 272.4, 268.4, 272.7, 546/275.4, 276.4; 514/336, 340, 341, 342
See application file for complete search history.

(56) References Cited

U.S. PATENT DOCUMENTS 6,291,491 B1    9/2001    Weber et al.

OTHER PUBLICATIONS

Dow et al. Potent and selective, sulfamide-based human beta3-adrenergic receptor agonists, Bioorganic & Medicinal Chemistry Letters, vol. 14, No. 12, p. 3235-3240 (2004).

*Primary Examiner* — Patricia L Morris
(74) *Attorney, Agent, or Firm* — Patricia A. Shatynski; Valerie J. Camara

(57) ABSTRACT

The present invention provides compounds of Formula I, pharmaceutical compositions thereof, and method of using the same in the treatment or prevention of diseases mediated by the activation of β3-adrenoceptor.

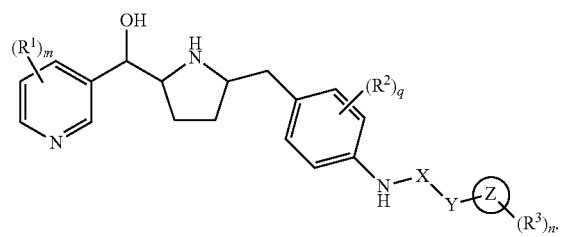

8 Claims, No Drawings

HYDROXYMETHYL PYRROLIDINES AS BETA 3 ADRENERGIC RECEPTOR AGONISTS

CROSS REFERENCE TO RELATED APPLICATIONS

This application is a U.S. National Phase application under 35 U.S.C. §371 of PCT Application No. PCT/US2009/037911, filed Mar. 23, 2009, which claims priority under 35 U.S.C. §119(e) from U.S. Provisional Application Ser. No. 61/123,062, filed Apr. 4, 2008.

BACKGROUND OF THE INVENTION

The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

β Adrenergic receptors (βAR) are present in detrusor smooth muscle of various species, including human, rat, guinea pig, rabbit, ferret, dog, cat, pig and non-human primate. However, pharmacological studies indicate there are marked species differences in the receptor subtypes mediating relaxation of the isolated detrusor; β1AR predominate in cats and guinea pig, β2AR predominate in rabbit, and β3AR contribute or predominate in dog, rat, ferret, pig, cynomolgus and human detrusor. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97%, cf 1.5% for β1AR mRNA and 1.4% for β2AR mRNA). Moreover, β3AR mRNA expression was equivalent in control and obstructed human bladders. These data suggest that bladder outlet obstruction does not result in downregulation of β3AR, or in alteration of β3AR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states.

Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume.

Overactive bladder is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological conditions, bladder outlet obstruction, and other causes. From a pathophysiologic perspective, the overactive bladder symptom complex, especially when associated with urge incontinence, is suggestive of detrusor overactivity. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy). Therefore, there is need for new, well-tolerated therapies that effectively treat urinary frequency, urgency and incontinence, either as monotherapy or in combination with available therapies. Agents that relax bladder smooth muscle, such as β3AR agonists, are expected to be effective for treating such urinary disorders.

SUMMARY OF THE INVENTION

The present invention relates to novel β3AR agonists, pharmaceutical compositions containing them, as well as methods for the treatment or prophylaxis of disorders mediated through the β3AR using such novel compounds.

DESCRIPTION OF THE INVENTION

The present invention describes compounds of structural Formula I:

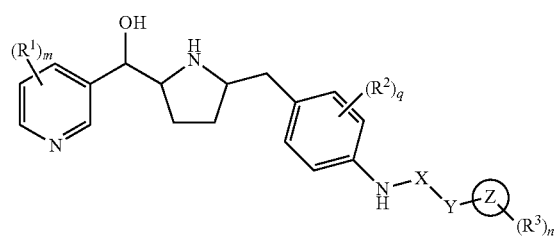

wherein
m is 0, 1, 2, 3 or 4;
n is 0, 1, 2, 3, 4 or 5;
q is 0, 1, 2, 3 or 4;
X is —CO— or —SO$_2$—;
Y is selected from the group consisting of:
   (1) C$_1$-C$_5$ alkanediyl, C$_2$-C$_5$ alkenediyl, and C$_2$-C$_5$ alkynediyl, wherein each of alkanediyl, alkenediyl and alkynediyl is optionally substituted with one to three groups independently selected from halogen, —OR$^a$, —S(O)$_p$—C$_1$-C$_3$ alkyl, wherein p is 0, 1 or 2,
   (2) (CR$^a$R$^a$)$_j$-Q-(CR$^a$R$^a$)$_k$ wherein j and k are integers independently selected from 0, 1 and 2,
   (3) a bond, and
   (4) phenylene optionally substituted with one to three groups independently selected from R$^1$;
Z is selected from the group consisting of:
   (1) phenyl,
   (2) a 5- or 6-membered heterocyclic ring with from 1 to 4 heteroatoms selected from oxygen, sulfur and nitrogen,
   (3) a benzene ring fused to a C$_5$-C$_{10}$ carbocyclic ring,
   (4) a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen, and (5) a 5- or 6-membered heterocyclic ring with from 1 to 4 heteroatoms selected from oxygen, sulfur and nitrogen fused to a $C_5$-$C_{10}$ carbocyclic ring;

$R^1$ is selected from the group consisting of:
(1) $C_1$-$C_5$ alkyl optionally substituted with 1 to 5 halogen atoms,
(2) $C_3$-$C_6$ cycloalkyl,
(3) halogen,
(4) nitro,
(5) cyano,
(6) $C(O)R^a$,
(7) $C(O)_2R^a$,
(8) $C(O)NR^aR^b$, and
(9) $QR^b$;

$R^2$ is selected from halogen or $C_1$-$C_5$ alkyl;
$R^3$ is selected from the group consisting of:
(1) $C_1$-$C_6$ alkyl optionally substituted with 1 to 5 groups independently selected from halogen, —$OR^a$ and —$CO_2R^a$ and —$CONR^aR^b$,
(2) —$(CH_2)_n$-phenyl or —$(CH_2)_n$—O-phenyl wherein said phenyl in each is optionally substituted with 1 to 3 groups independently selected from halogen, $C_1$-$C_5$ alkyl optionally substituted with 1-5 halogen atoms, and —$OR^a$,
(3) oxo,
(4) thioxo,
(5) halogen,
(6) —CN,
(7) $C_3$-$C_6$ cycloalkyl,
(8) a 5 or 6-membered heterocyclic ring with from 1 to 4 heteroatoms selected from oxygen, sulfur and nitrogen, and wherein said ring is optionally ortho-fused to a benzene ring, and optionally substituted with 1 to 3 groups independently selected from halogen, $C_1$-$C_5$ alkyl optionally substituted with 1-5 halogen atoms, and $OR^a$,
(9) —$OR^a$,
(10) —$C(O)OR^a$,
(11) —$C(O)R^a$,
(12) —$C(O)NR^aR^b$,
(12) —$NR^aR^b$,
(13) —$NR^aC(O)R^b$,
(14) —$NR^aC(O)OR^b$, and
(15) —$NR^aC(O)NR^aR^b$;

$R^a$ is selected from hydrogen and $C_1$-$C_6$ alkyl optionally substituted with 1 to 5 halogen atoms;
$R^b$ is selected from
(1) hydrogen,
(2) $C_1$-$C_6$ alkyl optionally substituted with 1 to 5 groups selected from
  (a) hydroxy,
  (b) halogen,
  (c) —$CO_2R^a$,
  (d) —$S(O)_p$—$C_1$-$C_3$ alkyl,
  (e) $C_3$-$C_8$ cycloalkyl,
  (f) $C_1$-$C_6$ alkoxy optionally substituted with 1 to 5 halogens, and
  (g) phenyl optionally substituted with 1 to 5 groups independently selected from halogen, nitro, —$NR^aR^a$, trifluoromethyl, trifluoromethoxy, $C_1$-$C_5$ alkyl and $OR^a$,
(3) $C_3$-$C_8$ cycloalkyl, or
(4) phenyl optionally substituted with 1 to 5 groups selected from the group consisting of:
  (a) halogen,
  (b) nitro,
  (c) —$NR^aR^a$,
  (d) —OH,
  (e) $C_1$-$C_6$ alkoxy optionally substituted with 1 to 5 halogens,
  (f) —$S(O)_p$—$C_1$-$C_6$ alkyl, and
  (g) $C_1$-$C_6$ alkyl optionally substituted with up to 5 groups selected from hydroxy, halogen, trifluoromethyl, cyano, $CO_2R^a$, $C_3$-$C_8$ cycloalkyl, and $QR^c$;

$R^c$ is selected from the group consisting of:
(1) Z optionally substituted with up to 5 groups selected from halogen, trifluoromethyl, cyano, $C_1$-$C_5$ alkyl and $C_1$-$C_5$ alkoxy, and
(2) $C_1$-$C_6$ alkyl;

Q is selected from the group consisting of:
(1) —$N(R^a)$—,
(2) —O— or
(3) —$S(O)_{p-}$; wherein p is 0, 1 or 2;
or a pharmaceutically acceptable salt thereof.

In one embodiment of the compounds of Formula I are compounds of Formula Ia:

Ia wherein Y, Z, $R^3$ and n are as defined above in Formula I.

In one embodiment of Formulas I and Ia are compounds wherein Y is methylene, —$CH(CH_3)$— or a bond. In one subset thereof Y is methylene. In another subset thereof Y is a bond.

In another embodiment of Formulas I and Ia are compounds where Y is phenylene.

In another embodiment of Formulas I and Ia are compounds wherein Z is a 5- or 6-membered heterocyclic ring with from 1 to 4 heteroatoms selected from oxygen, sulfur and nitrogen. In one subset Z is a 5-membered heterocycle having one nitrogen atom and 0-3 additional heteroatoms independently selected from N, O and S. In another subset Z is a 6-membered heterocycle having 1, 2 or 3 nitrogen atoms, or 1 nitrogen atom and an oxygen or sulfur atom. In yet another subset, Z is selected from the group consisting of thiazolyl, oxazolyl, pyridyl, dihydropyridyl, triazolyl (including 1,2,4-triazolyl and 1,2,3-triazolyl), tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, and oxadiazolyl (including 1,2,4-oxadiazolyl and 1,2,5-oxadiazolyl). In one subset of this embodiment, Y is methylene.

In another embodiment of Formulas I and Ia are compounds wherein Z is a 5- or 6-membered heterocyclic ring with from 1 to 4 heteroatoms selected from oxygen, sulfur and nitrogen fused to a $C_5$-$C_{10}$ carbocyclic ring. In one subset the carbocyclic ring has 5 or 6 carbon atoms. In another subset the heterocycle is either a 5-membered heterocycle having one nitrogen atom and 0-3 additional heteroatoms independently selected from N, O and S, or a 6-membered heterocycle having 1, 2 or 3 nitrogen atoms, or 1 nitrogen atom and an oxygen or sulfur atom, and the carbocycle has 5 or 6 carbon atoms. In yet another subset Z is selected from the group consisting of: indolyl, benzimidazolyl, benzthiazolyl, quinolinyl, isoquinolinyl, tetrahydroquinolinyl, tetrahydroisoquinolinyl, chromenyl, benztriazolyl,

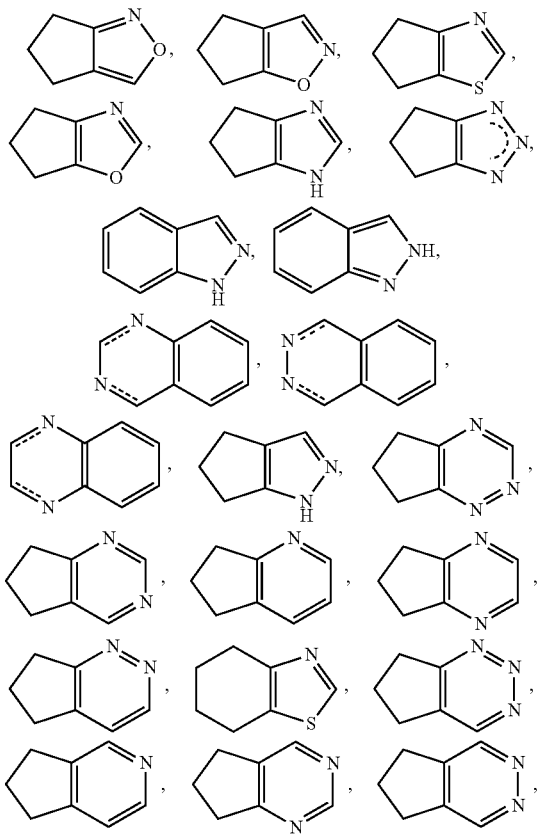

where the dash bond "---" means a single or double bond while conforming to the valency rule for the ring atoms. In one subset of this embodiment Y is methylene. In another subset, Y is a bond.

In another embodiment of Formula I and Formula Ia are compounds wherein Z is a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen. In one subset the fused ring has 2-5 heteroatoms, at least one of which is nitrogen. In another subset the fused ring has 2-4 nitrogen atoms and no other heteroatoms. In yet another subset the fused ring has one oxygen or sulfur atom, and 1-3 nitrogen atoms. In yet another subset, Z is selected from the group consisting of:

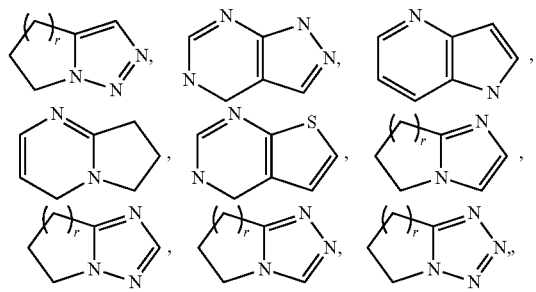

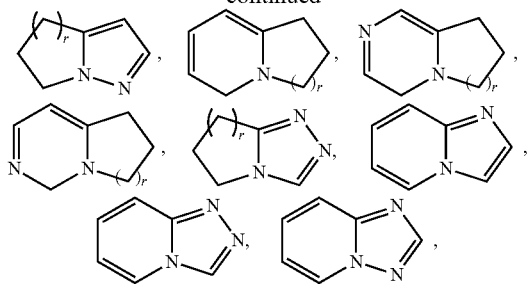

wherein r is 1 or 2. In one subset of this embodiment Y is methylene. In nother subset, Y is a bond.

In compounds of Formulas I and Ia, examples of $R^3$ (when n is not 0) include, but are not limited to, $—NR^aR^a$, $C_1$-$C_6$alkyl optionally substituted with halogen or $—OR^a$, $—OR^a$, $C_3$-$C_6$cycloalkyl, phenyl optionally substituted with halogen, benzyl, pyridyl, thiazolyl, oxo, halogen, cyano, optionally halo-substituted $C_1$-$C_6$alkanoyl, ($C_1$-$C_6$alkyl)NHC(O)NH—, $—C(O)NR^aR^a$. More particular examples of $R^3$ include methyl, ethyl, propyl, isopropyl, trifluoromethyl, oxo, fluoro and chloro.

In another embodiment of Formulas I and Ia are compounds having the specified stereoconfiguration at the indicated chiral center:

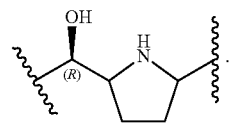

In another embodiment of Formulas I and Ia are compounds having the specified stereoconfiguration at the indicated chiral centers, with the chiral center marked with an asterisk being R or S:

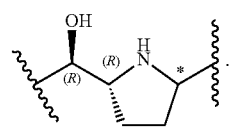

In one subset, the configuration at the chiral center marked with an asterisk is S.

As used herein "alkyl" is intended to include both branched- and straight-chain saturated aliphatic hydrocarbon groups having the specified number of carbon atoms, e.g., methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tertbutyl (t-Bu), isopentyl, isohexyl and the like. "Cycloalkyl" means a monocyclic saturated carbocyclic ring, having the specified number of carbon atoms, e.g., 3, 4, 5 or 6 carbon atoms. Examples of cycloalkyl include cyclopropyl, cyclobutyl, cyclopentyl and cyclohexyl.

The term "alkanediyl" refers to a straight or branched divalent hydrocarbon radical having the specified number of carbon atoms. "Alkenediyl" and "alkynediyl" refer to straight or branched, unsaturated divalent hydrocarbon radicals. An "alkenediyl" is characterized by a carbon-carbon double bond and an "alkynediyl" is characterized by a carbon-carbon triple bond. Examples of "alkanediyl" include, but are not limited to, methylene (—CH$_2$—), ethylene (—CH$_2$CH$_2$—), 1,1-ethanediyl (—CH(CH₃)—), 1,2-propanediyl (—CH(CH₃)CH₂—), 2-methyl-1,1-propanediyl (—CH[C(CH₃)₂]—); examples of "alkenediyl" include, but are not limited to, 1,1-ethenediyl (—C(=CH₂)—), 1,2-ethenediyl (—CH=CH—), and 2-propen-1,1-diyl (—CH(CH=CH₂)—); examples of "alkynediyl" include, but are not limited to, 1,2-ethynediyl (—C≡C—) and 3-butyn-1,1-diyl (—CH(CH₂C≡CH)—). Example of a halogen substituted alkanediyl is —C(CH₃)(F)—.

The term "optionally substituted" means "unsubstituted or substituted," and therefore, the generic structural formulas described herein encompasses compounds containing the specified optional substituent as well as compounds that do not contain the optional substituent. Each variable is independently defined each time it occurs within the generic structural formula definitions.

The terms "halo" or "halogen" are meant to include fluoro, chloro, bromo and iodo, unless otherwise noted. Fluoro and chloro are preferred.

The term "carbocycle" or "carbocyclic" refers to saturated, partially unsaturated and aromatic rings having only ring carbon atoms. Examples include, but are not limited to cyclopentyl, cyclohexyl, cycloheptyl, cyclooctyl, cyclopentenyl, cyclohexenyl, cyclohexadienyl, and phenyl. The term "aryl" refers to an aromatic carbocycle. Within the definition for Z, the term "a benzene ring fused to a $C_5$-$C_{10}$ carbocyclic ring" includes, but is not limited to, naphthyl, dihydronaphthyl, tetrahydronaphthyl, indanyl, indenyl, benzocycloheptene, tetrahydrobenzocyloheptene, and the like; preferably benzene is fused to a $C_5$-$C_6$ carbocyclic ring. Such fused ring may be attached to the rest of the molecule via a carbon atom on either ring.

The term "heterocycle" or "heterocyclic" refers to saturated, partially unsaturated and aromatic rings having at least one ring heteroatom and at least one ring carbon atom; the heterocycle may be attached to the rest of the molecule via a ring carbon atom or a ring nitrogen atom. The term "heteroaryl" or "heteroaromatic" refers to an aromatic heterocycle. Within the definition for Z, the term "a 5- or 6-membered heterocyclic ring with from 1 to 4 heteroatoms selected from oxygen, sulfur and nitrogen" includes, but is not limited to, pyrrolyl, thienyl, furanyl, imidazoly, pyrazolyl, oxazolyl, isoxazolyl, thiazolyl, isothiazolyl, triazolyl, tetrazolyl, oxadiazolyl, thiadiazolyl, pyrrolidinyl, tetrahydrofuranyl, pyridinyl, dihydropyridinyl, tetrahydropyridinyl, pyrimidinyl, dihydropyrimidinyl, tetrahydropyrimidinyl, pyrazinyl, dihydropyrazinyl, tetrahydropyrazinyl, pyridazinyl, dihydropyridazinyl, tetrahydropyridazinyl, piperidinyl, piperazinyl, morpholinyl, pyranyl, dihydropyranyl, tetrahydropyranyl, and the like.

Within the definition for Z, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" includes, but is not limited to, naphthyridinyl, dihydronaphthyridinyl, tetrahydronaphthyridinyl, imidazopyridinyl, pteridinyl, purinyl, quinolizinyl, indolizinyl, tetrahydroquinolizinyl, tetrahydroindolizinyl,

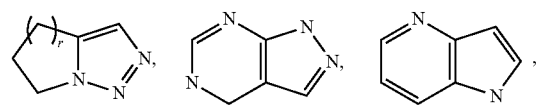

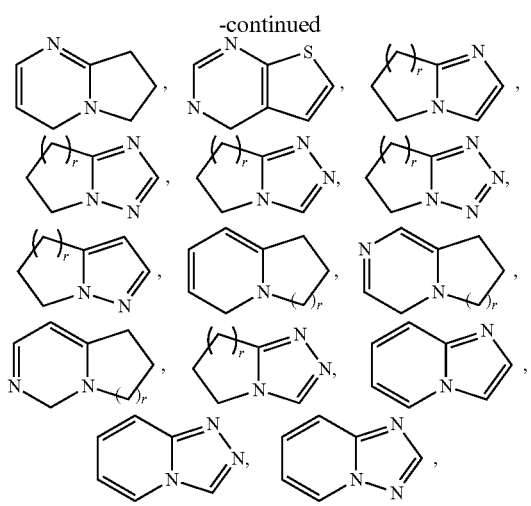

wherein r is 1 or 2. Such fused ring may be attached to the rest of the molecule via a carbon atom or a nitrogen atom on either ring.

To avoid any doubt, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" as used herein includes compounds having only one nitrogen as the sole heteroatom when the nitrogen is located at the bridgehead.

Within the definition for Z, the term "a 5- or 6-membered heterocyclic ring with from 1 to 4 heteroatoms selected from oxygen, sulfur and nitrogen fused to a $C_5$-$C_{10}$ carbocyclic ring" includes, but is not limited to, indolyl, isoindolyl, benzofuranyl, benzothienyl, benzimidazolyl, benzotriazolyl, benzoxazolyl, benzisoxazolyl, benzthiazolyl, benzisothiazolyl, quinolinyl, isoquinolinyl, quinoxalinyl, quinazolinyl, cinnolinyl, indazolyl, tetrahydroquinolinyl, tetrahydroindazolyl, dihydroindazolyl, chromenyl, chromanyl,

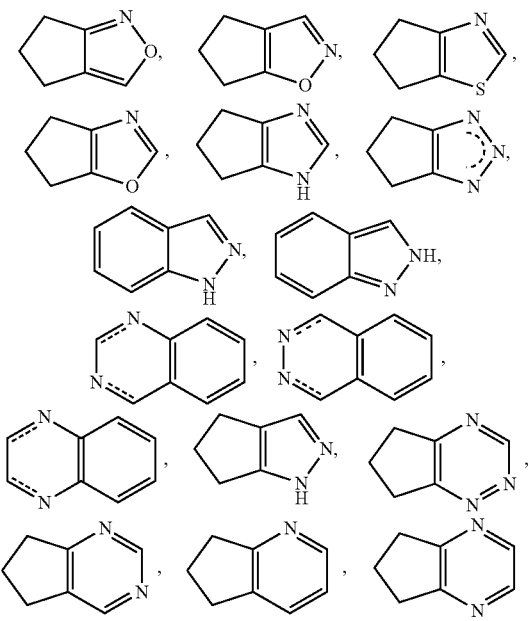

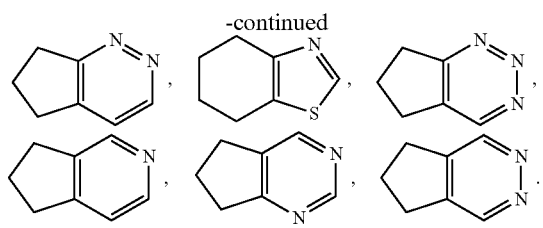

Such fused ring may be attached to the rest of the molecule via a carbon atom or a nitrogne atom on either ring.

For the terms $(R^1)_m$, $(R^2)_q$, $(R^3)_n$, as well as any other similar notations, when m or q or n is 0, then $R^1$, $R^2$ or $R^3$ is hydrogen; when m, q or n is greater than 1, then each occurrence of $R^1$, $R^2$ or $R^3$ is independently selected from other occurrences of $R^1$, $R^2$ or $R^3$, respectively. For example, when n is 2, the two $R^3$ substituents can be the same or different.

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formulas I and Ia are shown without a definitive stereochemistry at certain positions. The present invention includes all stereoisomers of Formulas I and Ia and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I or Ia may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are included within the scope of the present invention.

Pharmaceutically Acceptable Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glutamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, maize, mandelic, methanesulfonic, muck, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formulas I and Ia. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono, sesqui-, di- and trihydrates.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of Formula I or Ia or with a compound which may not be a compound of Formula I or Ia, but which converts to a compound of Formula I or Ia in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound of Formula I or Ia. The term "mammal" includes human and non-human animals such as dogs and cats and the like. The diseases, disorders or conditions for which compounds of the present invention are useful in treating or preventing include, but are not limited to, (1) overactive bladder, (2) urinary incontinence, (3) urge urinary incontinence, (4) urinary urgency, (5) diabetes mellitus, (6) hyperglycemia, (7) obesity, (8) hyperlipidemia, (9) hypertriglyceridemia, (10) hypercholesterolemia, (11) atherosclerosis of coronary, cerebrovascular and peripheral arteries, (12) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (13) neurogenic inflammation of airways, including cough, asthma, (14) depression, (15) prostate diseases such as benign prostate hyperplasia, (16) irritable bowel syndrome and other disorders needing decreased gut motility, (17) diabetic retinopathy, (18) preterm labor, and (19)-elevated intraocular pressure and glaucoma.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I or Ia are administered orally.

The effective dosage of active ingredient employed may vary depending on the particular compound employed, the mode of administration, the condition being treated and the severity of the condition being treated. Such dosage may be ascertained readily by a person skilled in the art.

When treating overactive bladder (OAB) in conjunction with other anti-OAB agents, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

When treating diabetes mellitus and/or hyperglycemia, as well as other diseases or disorders for which compounds of Formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

Another aspect of the present invention provides pharmaceutical compositions which comprises a compound of Formula I and a pharmaceutically acceptable carrier. The pharmaceutical compositions of the present invention comprise a compound of Formula I or Ia as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, intravesical, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I or Ia can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of Formula I or Ia may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds of Formula I or Ia may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I or Ia. When a compound of Formula I or Ia is used contemporaneously with one or more other drugs, a pharmaceutical unit dosage form containing such other drugs in addition to the compound of Formula I or Ia is preferred. Accordingly, the pharmaceutical compositions of the present invention include those that also contain one or more other active ingredients, in addition to a compound of Formula I or Ia. Examples of other active ingredients that may be combined with a compound of Formula I, either administered separately or in the same pharmaceutical compositions, include, but are not limited to:

(a) overactive bladder medicines including (i) muscarinic receptor antagonists (e.g. tolterodine, oxybutynin, hyoscyamine, propantheline, propiverine, trospium, solifenacin, darifenacin, fesoterodine, temiverine, and other anticholinergics), (ii) NK-1 or NK-2 antagonists (e.g. aprepitant, cizolirtine, compounds disclosed in WP2005/073191, WO2005/032464, and other reported NK-1 antagonists), (iii) alpha adrenergic receptor antagonists (e.g. alfuzosin, doxazosin, prazosin, tamsulosin, terazosin, and others), (iv) potassium channel openers (e.g. cromakalim, pinacidil, and others), (v) vanilloids and other afferent-nerve modulators—agonists and antagonists (e.g. capsaicin, resiniferatoxin, and others), (vi) dopamine D1 receptor agonists (e.g. pergolinde), (vii) serotonergic and/or norepinephrine reuptake inhibitors (e.g. duloxetine), (viii) neuromuscular junction inhibition of acetylcholine release (e.g. botulinum toxin), (ix) calcium channel blockers (e.g. diltiazem, nifedipine, verapamil, and others), (x) inhibitors of prostaglandin synthesis (e.g. flurbiprofen), (xi) gamma aminobutyric acid receptor antagonists (e.g. baclofen), (xii) vaginal estrogen preparations (xiii) selective norepinephrine reuptake inhibitors, (xiv) 5-HT2C agonists, (xv) voltage gated sodium channel blocker, (xvi) P2X purinergic receptor antagonists, (xvii) PAR2 inhibitors, (xviii) phosphodiesterase 5 inhibitors; (xix) ATP sensitive potassium channel openers, (xx) purinergic receptor antagonists.

(b) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(c) insulin or insulin mimetics;

(d) sulfonylureas such as tolbutamide and glipizide;

(e) α-glucosidase inhibitors (such as acarbose), (f) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor a agonists such as fenofibric acid derivatives (gemfibrozil, clofibrat, fenofibrate and benzafibrate), (iv) inhibitors of cholesterol absorption for example beta-sitosterol and ezetimibe, and (acyl CoA:cholesterol acyltransferase) inhibitors for example melinamide, (v) probucol, (vi) vitamin E, and (vii) thyromimetics;

(g) PPARδ agonists such as those disclosed in WO97/28149;

(h) antiobesity compounds such as fenfluramine, dexfenfluramine, phentermine, sibutramine, orlistat, and other β3 adrenergic receptor agonists;

(i) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(j) PPARα agonists such as described in WO 97/36579 by Glaxo;

(k) PPARγ antagonists as described in WO97/10813; and (l) serotonin reuptake inhibitors such as fluoxetine and sertraline.

The compounds of Formula I or Ia of the present invention can be prepared according to the procedures of the following Schemes and Examples using appropriate materials, and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Throughout the application, the following terms have the indicated meanings unless otherwise noted:

| Term | Meaning |
|---|---|
| Ac | Acyl ($CH_3C(O)$—) |
| Aq. | Aqueous |
| Bn | Benzyl |
| BOC (Boc) | t-Butyloxycarbonyl |
| BOP | Benzotriazol-1-yloxytris(dimethylamino)phosphonium hexafluorophosphate |
| ° C. | Degree Celsius |
| Calc. or calc'd | Calculated |
| Celite | Celite ™ diatomaceous earth |
| DCC | Dicyclohexylcarbodiimide |
| DIEA | N,N-diisopropyl-ethylamine |
| DMF | N,N-dimethylformamide |
| EDC | 1-Ethyl-3-(3-dimethylaminopropyl) carbodiimide |
| Eq. | Equivalent(s) |
| ES-MS and ESI-MS | Electron spray ion-mass spectroscopy |
| Et | Ethyl |
| EtOAc | Ethyl acetate |
| g | Gram(s) |
| h or hr | Hour(s) |
| HATU | O-(7-azabenzotriazol-1-yl)-N,N,N',N'-tetramethyluronium hexafluorophosphate |
| HCl | Hydrogen chloride |
| HOAc | Acetic acid |
| HOAT | 1-Hydroxy-7-azabenzotriazole |
| HOBT | 1-Hydroxybenzotriazole |
| HPLC | High performance liquid chromatography |
| IPA | Isopropyl alcohol |
| LiOH | Lithium hydroxide |
| LDA | Lithium diisopropylamide |
| LiHMDS | Lithium bis(trimethylsilyl)amide |
| LC/MS or LC-MASS | Liquid chromatography mass spectrum |
| L | Liter(s) |
| Me | Methyl |
| MeOH | Methanol |
| MF | Molecular formula |
| min | Minute(s) |
| mg | Milligram(s) |
| mL | Milliliter(s) |
| mmol | Millimole(s) |
| MOZ (Moz) | p-Methoxybenzyloxycarbonyl |
| MS | Mass spectrum |
| NaH | Sodium hydride |
| OTf | Trifluoromethanesulfonyl |
| 10% Pd/C | Palladium, 10 weight percent on activated carbon |
| Ph | Phenyl |
| Prep. | Prepared |
| r.t. or rt | Room temperature |
| Sat. | Saturated |
| SCF $CO_2$ S | Super critical fluid carbon dioxide |
| TBAF | Tetrabutylammonium fluoride |
| TEA or $Et_3N$ | Triethylamine |
| Tf | Triflate or trifluoromethanesulfonate |
| TFA | Trifluoroacetic acid |
| THF | Tetrahydrofuran |
| TBDS or TBS | Tert-butyldimethylsilyl |
| TMSOK | Potassium trimethylsilanolate |
| TLC | Thin-layer chromatography |

Reaction Schemes I-X illustrate the methods employed in the synthesis of the compounds of the present invention of Formula I or Ia. All substituents are as defined above unless indicated otherwise. The synthesis of the novel compounds of Formula I or Ia which are the subject of this invention may be accomplished by one or more of several similar routes. The preparation of these intermediates is described in the following Schemes, wherein $R^1$ to $R^{14}$ are either defined in the schemes or as defined above.

In Scheme I, commercially available I-1 is first treated with trimethylacetyl chloride in the presence of a weak organic base such as triethylamine at −25° C. for 2 h. The sequential addition of anhydrous lithium chloride and (S)-(−)-4-benzyl-2-oxazolidinone to the mixture followed by gradual warming to room temperature over a period of time between 12 and 16 h affords imide I-2. The reaction is usually performed in an inert organic solvent, such as THF, under an inert atmosphere, such as nitrogen. The alcohol I-4 is prepared according to published procedures (See Evans et al., J. Am. Chem. Soc. 2002, 124, 392-394). For example, treatment of I-2 with anhydrous magnesium chloride, triethylamine, the appropriate aldehyde I-3, such as 6-chloropyridine-3-carboxaldehyde, and chlorotrimethylsilane at room temperature over a period of 72 h yields the trimethylsilyl ether of the aldol product I-4. The reaction is usually performed in an organic solvent such as ethyl acetate under an inert atmosphere such as nitrogen. Treatment of the trimethylsilyl ether intermediate with a trifluoroacetic acid and methanol mixture affords the desired alcohol I-4. Conversion of I-4 to I-5 can be achieved by selecting the desired silyl protecting agent, such as tert-butyl dimethylsilyl trifluoromethanesulfonate, and reacting it in the presence of a weak organic base, such as 2,6-lutidine, at 0° C. for a period of between 12 to 16 h. The hydrolysis of imide I-5 is achieved by treatment with lithium peroxide at 0° C. for a period of 15-18 h. The peroxy acid is subsequently reduced with an aqueous solution of sodium sulfite to afford the carboxylic acid I-6. The reaction is usually performed in a mixture of an inert organic solvent, such as THF, and water under an inert atmosphere, such as nitrogen. Finally, I-6 is treated with diphenylphosphoryl azide in the presence of a weak organic base such as triethylamine for a period of 6 h at room temperature. Addition of the appropriate alcohol, such as 4-methoxybenzyl alcohol, with heating to 100° C. for a period between 12 and 16 h yields the corresponding carbamate I-7. The reaction is usually performed in an inert organic solvent, like toluene, under an inert atmosphere, such as nitrogen. This material forms the basis in which the pyrrolidine core can been synthesized.

Scheme I

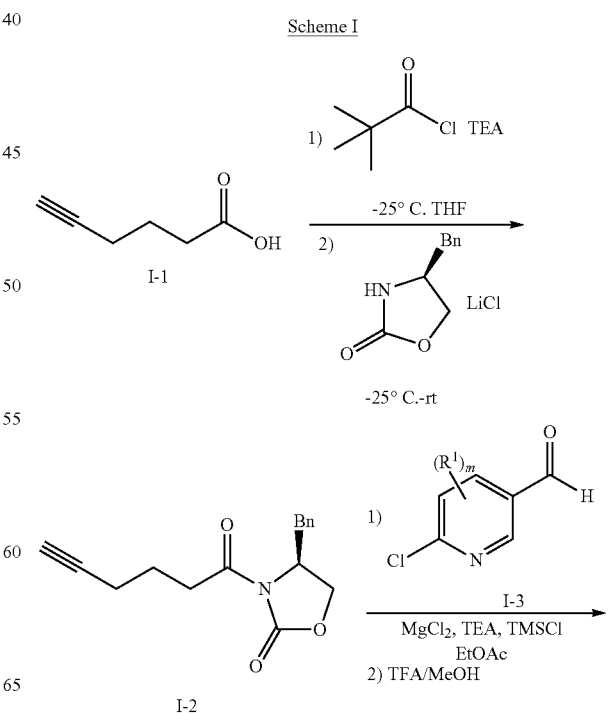

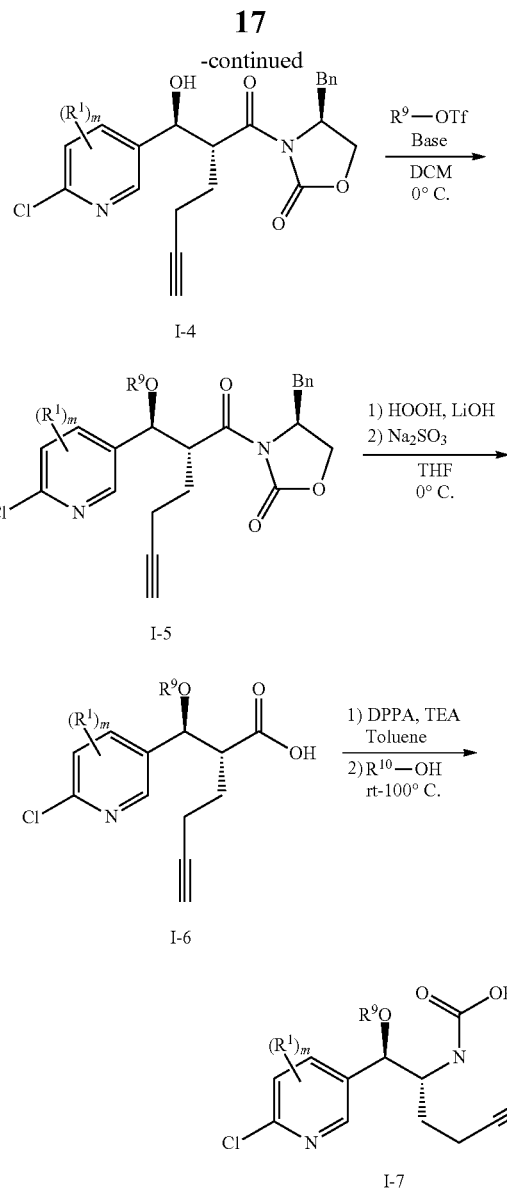

I-4

I-5

I-6

I-7

R⁹ is silyl hydroxy protecting group; R¹⁰ is carboxyl protecting group

Scheme II describes the synthesis of the cis-pyrrolidine (I-12) and trans-pyrrolidine (I-13) intermediates from the appropriately protected amine I-7 described in Scheme 1. The alkyne I-7 may be reacted in a Sonagashira type cross-coupling reaction with the corresponding commercially available aryl halide I-8 to afford I-9 using the appropriate reaction conditions known to those skilled in the art. The reaction conditions can include the use of catalysts, such as tetrakis(triphenylphosphine)-palladium(0), with copper(I)iodide in the presence of an organic base, such as triethylamine, or palladium(II)acetate with an organic base, such as tetrabutylammonium acetate, in an organic solvent, such as acetonitrile or DMF, under an inert atmosphere, such as nitrogen. Ketone I-10 may be prepared by the reaction of alkyne I-9 with pyrrolidine at a temperature of 80° C. in a solvent such as DMF for a period of between 3-6 h. Subsequent treatment with a 10% aqueous acetic acid solution for a period of between 15-60 min at room temperature yields ketone I-10. The carbamate protecting group of I-10 can be removed using the appropriate reaction conditions known to those skilled in the art to afford the corresponding amine, which subsequently undergoes an intramolecular ring closure with the ketone to afford the imine I-11. The reaction conditions can include trifluoroacetic acid in an organic solvent, such as dichloromethane, and hydrochloric acid in an organic solvent such as ether. Reduction of the imine I-11 can be achieved by treatment with sodium cyanoborohydride in an organic solvent, such as methanol, at a temperature of 0° C. under an inert atmosphere, such as nitrogen, for a period of between 18-24 h. This affords the cis-pyrrolidine (I-12) and trans-pyrrolidine (I-13) intermediates which can be separated by silica gel chromatography. I-12 is the major diastereomer produced in the reaction and is the first diastereomer to elute off the column.

Scheme II

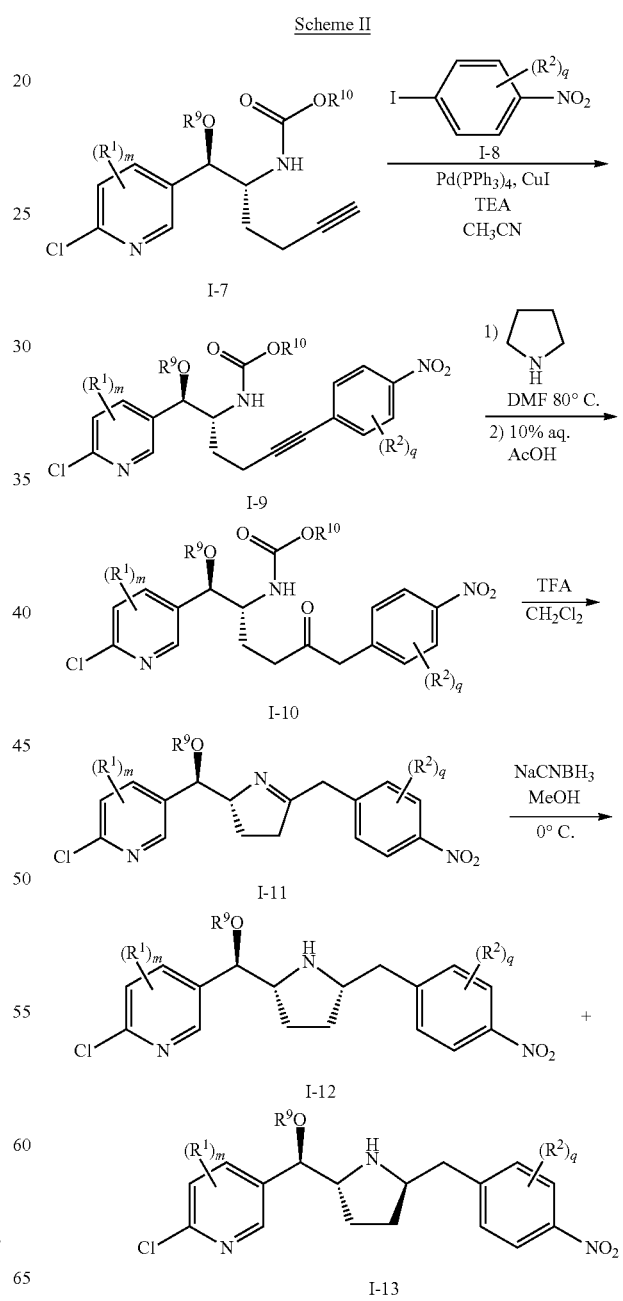

Scheme III describes the synthesis of the cis-pyrrolidine and trans-pyrrolidine cores I-15 from their corresponding intermediates I-12 and I-13 described in Scheme II. Protection of the pyrrolidine nitrogen of I-12 or I-13 with a Boc group is achieved by treatment with tert-butyl dicarbonate in the presence of a weak organic base, such as triethylamine. The reaction is usually performed in an organic solvent, such as dichloromethane, under an inert atmosphere, such as nitrogen, to afford the product of structural formula I-14. Hydrogenation of the intermediate I-14 by treatment with 10% palladium on carbon in the presence of potassium acetate under an atmosphere of hydrogen between 15 and 50 psi in a solvent, such as ethyl acetate or ethanol, over an 8-12 h period of time affords I-15. Alternatively I-14 can be treated with zinc metal in a solvent, such as acetic acid, at a temperature between 25 and 75° C. over an 8-12 h period of time to afford I-15. Depending on the choice of conditions, halogen substituents $R^1$ and $R^2$ can either remain or be removed at this time depending on preference of the final intermediate.

Scheme III

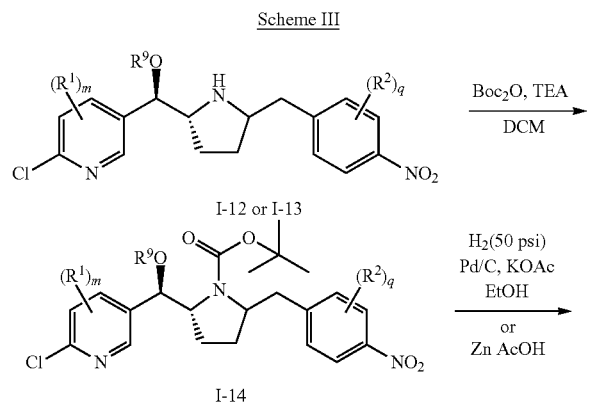

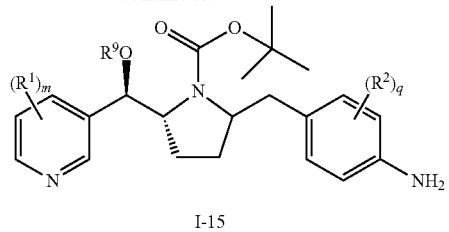

Scheme IV describes the preparation of sulfonamides of structural formula I-18 from either the cis- or trans-pyrrolidine intermediate I-15 by methods known to those skilled in the art. For example, treatment of I-15 with the desired sulfonyl chloride I-16 in the presence of a suitable organic base, such as DIEA, affords sulfonamide I-17. The reaction is usually performed in an inert organic solvent such as DMF, between room temperature and 50° C., for a period of 12-24 h. The sulfonyl chlorides I-16 are either commercially available, known in the literature or readily prepared by methods commonly known to those skilled in the art. Removal of the Boc and silyl protecting groups of I-17 simultaneously via treatment with a 3:3:1 mixture of acetonitrile:TFA:water at a temperature of 50° C. for a period of time between 1 and 6 h affords the desired sulfonamides I-18. Alternatively, sequential treatment of I-17 with a tetrabutylammonium fluoride solution in THF containing 5% water followed by treatment with a TFA solution in dichloromethane also yields the desired product of structural formula I-18. Additional deprotection steps may be included if other protecting groups are present. These protecting groups may include trityl groups, tert-butylcarbamate groups or other groups suitable for the protection of heterocyclic compounds or functional groups such as amines, hydroxyls, carboxylic acids or other groups known to those skilled in the art.

Scheme IV

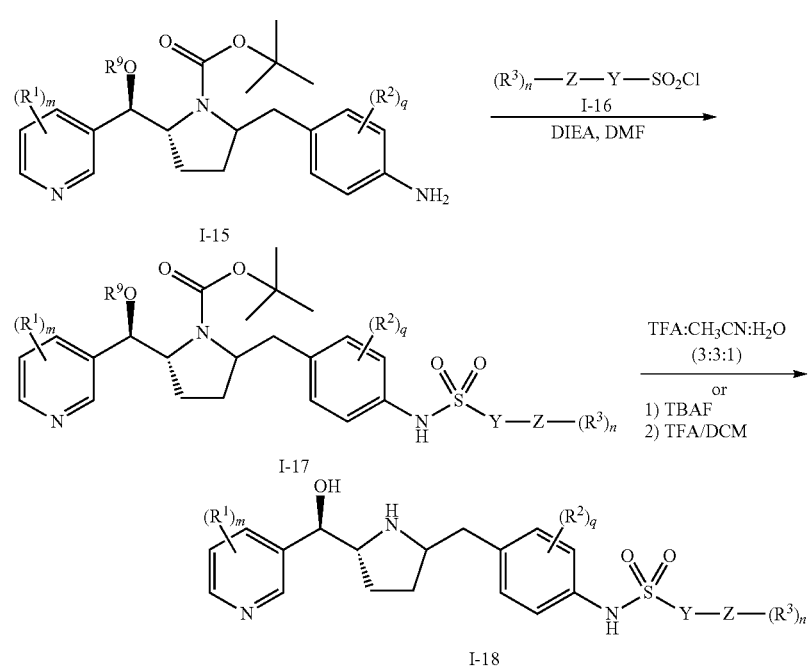

Scheme V describes the preparation of amides of structural formula I-21 from either the cis- or trans-pyrrolidine intermediate I-15 by methods known to those skilled in the art. For example, treatment of I-15 with the desired carboxylic acid I-19 in the presence of the appropriate amide coupling reagent, such as EDC, DCC, HAM or BOP, and the appropriate additive such as HOAT or HOBT, and either with or without a suitable organic base, such as N,N-diisopropylethylamine or triethylamine, affords amides of structural formula I-20. Alternatively, the desired carboxylic acid I-19 can be activated with methanesulfonyl chloride in the presence of 1-methylimidazole and reacted with I-15 to afford the desired amides of structural formula I-20. The reaction is usually performed in an inert organic solvent such as DMF, between room temperature and 50° C., for a period of 12-24 h. The carboxylic acids I-19 are either commercially available, known in the literature or readily prepared by methods commonly known to those skilled in the art. Removal of the Boc and silyl protecting groups of I-20 simultaneously via treatment with a 3:3:1 mixture of acetonitrile:TFA:water at a temperature of 50° C. for a period of time between 1 and 6 h affords amides of formula I-21. Alternatively, sequential treatment of I-20 with a tetrabutylammonium fluoride solution in THF containing 5% water followed by treatment with a TFA solution in dichloromethane also yields the desired product of structural formula I-21. Additional deprotection steps may be included if other protecting groups are present. These protecting groups may include trityl groups, tert-butylcarbamate groups or other groups suitable for the protection of heterocyclic compounds or the functional groups such as amines, hydroxyls, carboxylic acids or other groups known to those skilled in the art.

Scheme VI illustrates the preparation of N-aryl-proline derivatives I-19a by employing a cross-coupling reaction between an aromatic or heteroaromatic bromide and proline using methods known to those skilled in the art. For example, treatment of proline and an aromatic or heteroaromatic bromide I-22 with copper(I)iodide in the presence of a suitable inorganic base, such as potassium carbonate, affords the desired products of the various carboxylic acids of general structural formula I-19a. The reaction is usually performed in an inert organic solvent, such as DMF, at 100° C. for a period of 10-18 h.

Scheme VI

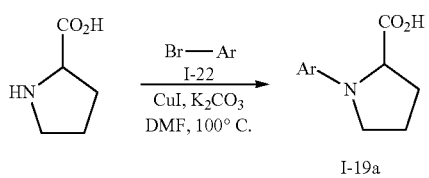

Scheme VII illustrates the preparation of the fused cycloalkylthiazole carboxylic acids of structural formula I-19b from intermediate I-23 using methods known to those skilled in the art. For example treatment of I-23 with a thiourea or a thioamide of structural formula I-24 affords esters of structural formula I-25. The reaction is usually performed in an organic solvent, such as ethanol, at 50° C. for a period of 12-24 h. Treatment of ester I-25 with lithium hydroxide in a 3:1:1 mixture of THF:methanol:water at ambient temperature for a period of time between 1 and 6 h affords the final desired carboxylic acids of formula I-19b.

Scheme V

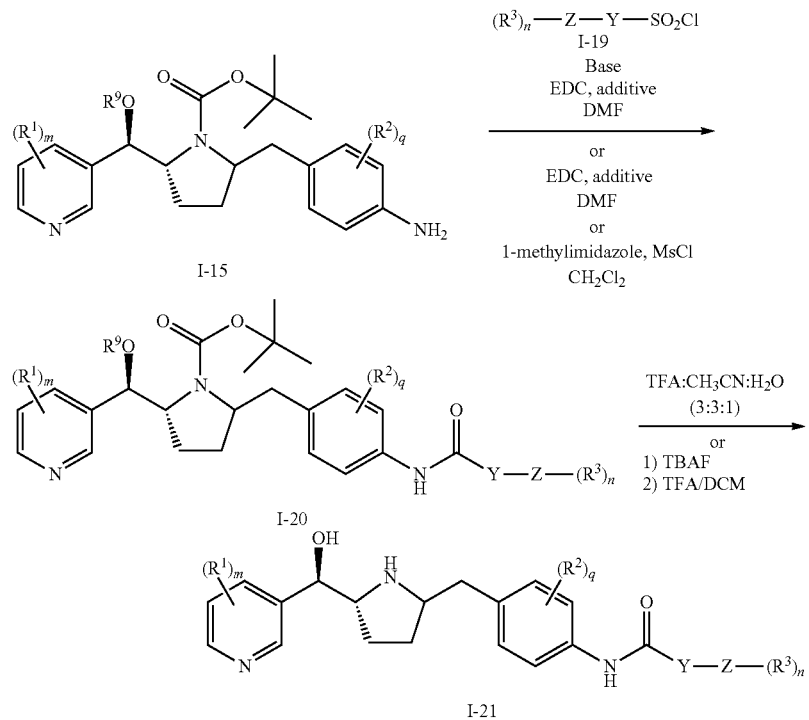

Scheme VII

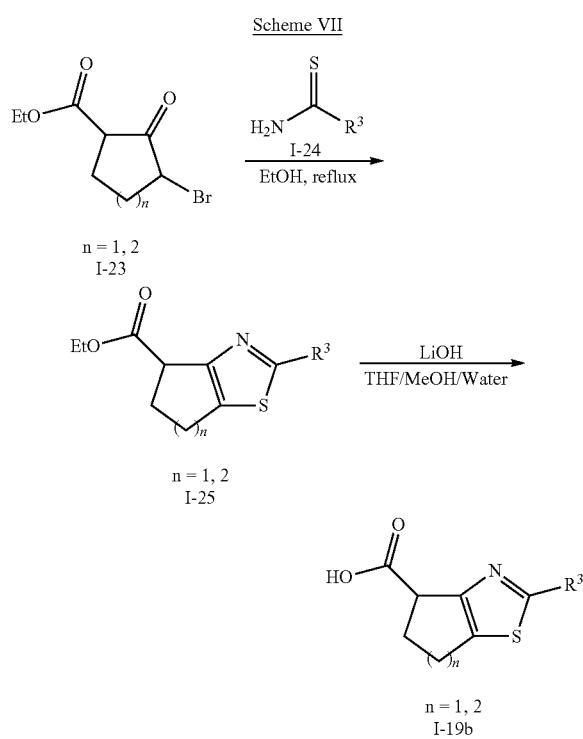

Scheme VIII describes the preparation of ureas of structural formula I-28 from either the cis- or trans-pyrrolidine intermediate I-15 by methods known to those skilled in the art. For example, treatment of I-15 with isocyanate I-26 and an amine in the presence of a suitable organic base, such as triethylamine, affords sulfonamides of structural formula I-27. The reaction is usually performed in an inert organic solvent such as DMF, between room temperature and 50° C., for a period of 12-24 h. Removal of the Boc and silyl protecting groups of I-27 simultaneously via treatment with a 3:3:1 mixture of acetonitrile:TFA:water at a temperature of 50° C. for a period of time between 1 and 6 h affords the sulfonamides of formula I-28. Alternatively, sequential treatment of I-27 with a tetrabutylammonium fluoride solution in THF containing 5% water followed by treatment with a TFA solution in dichloromethane also yields the desired product of structural formula I-28. Additional deprotection steps may be included if other protecting groups are present. These protecting groups may include trityl groups, tert-butylcarbamate groups or other groups suitable for the protection of heterocyclic compounds or the functional groups such as amines, hydroxyls, carboxylic acids or other groups known to those skilled in the art.

Scheme VIII

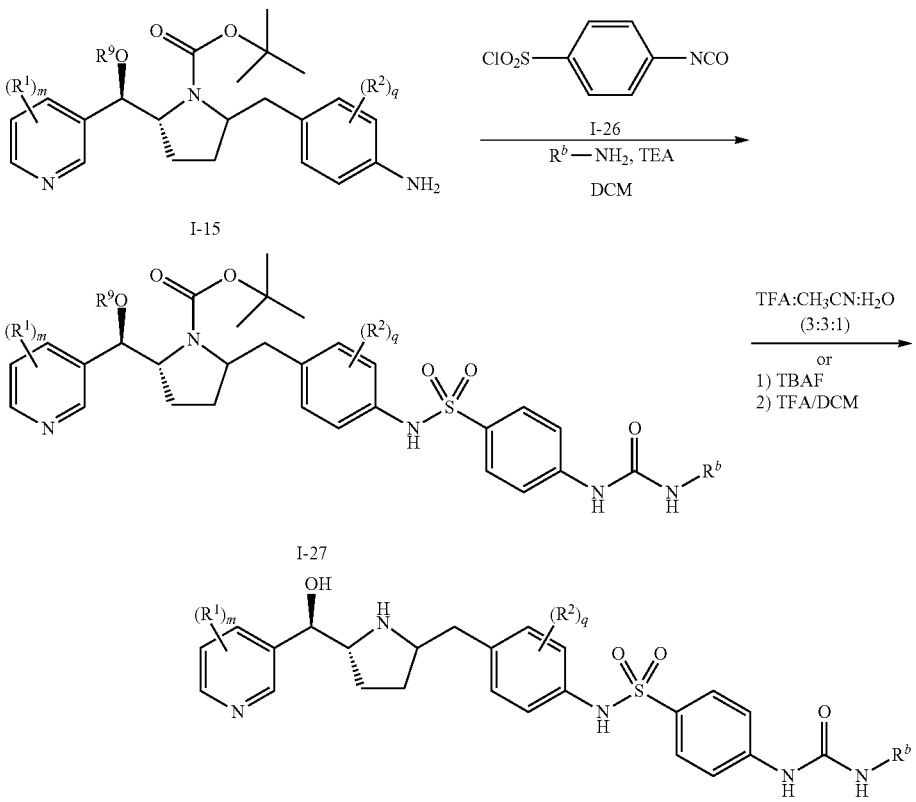

Scheme IX describes an alternative preparation of amides of structural formula I-21 from either the cis- or trans-pyrrolidine intermediate I-15 by methods known to those skilled in the art. For example, removal of the silyl protecting group of I-15 via treatment with a tetrabutylammonium fluoride solution in an inert organic solvent, such as THF, containing 5% water affords alcohols of general structural formula I-29. The reaction is usually performed in an inert organic solvent such as THF, between room temperature and 50° C., for a period of 12-24 h. Treatment of I-29 with the desired carboxylic acid I-19 in the presence of the appropriate amide coupling reagent, such as EDC, DCC, HATU or BOP, and the appropriate additive such as HOAT or HOBT, and either with or without a suitable organic base, such as N,N-diisopropylethylamine or triethylamine, affords amides of structural formula I-30. Alternatively, the desired carboxylic acid I-19 can be activated with methanesulfonyl chloride in the presence of 1-methylimidazole and reacted with I-29 to afford the desired amides of structural formula I-30. Removal of the Boc protecting groups of I-30 via treatment with a solution of TFA in an inert organic solvent, such as dichloromethane, at ambient temperature for a period of time between 1 and 6 h affords amides of formula I-21. Alternatively, treatment of I-30 with a solution of hydrogen chloride in an organic solvent, such as 1,4-dioxane or ethyl acetate, also yields the desired product of structural formula I-21. Additional deprotection steps may be included if other protecting groups are present. These protecting groups may include trityl groups, tert-butylcarbamate groups or other groups suitable for the protection of heterocyclic compounds or the functional groups such as amines, hydroxyls, carboxylic acids or other groups known to those skilled in the art.

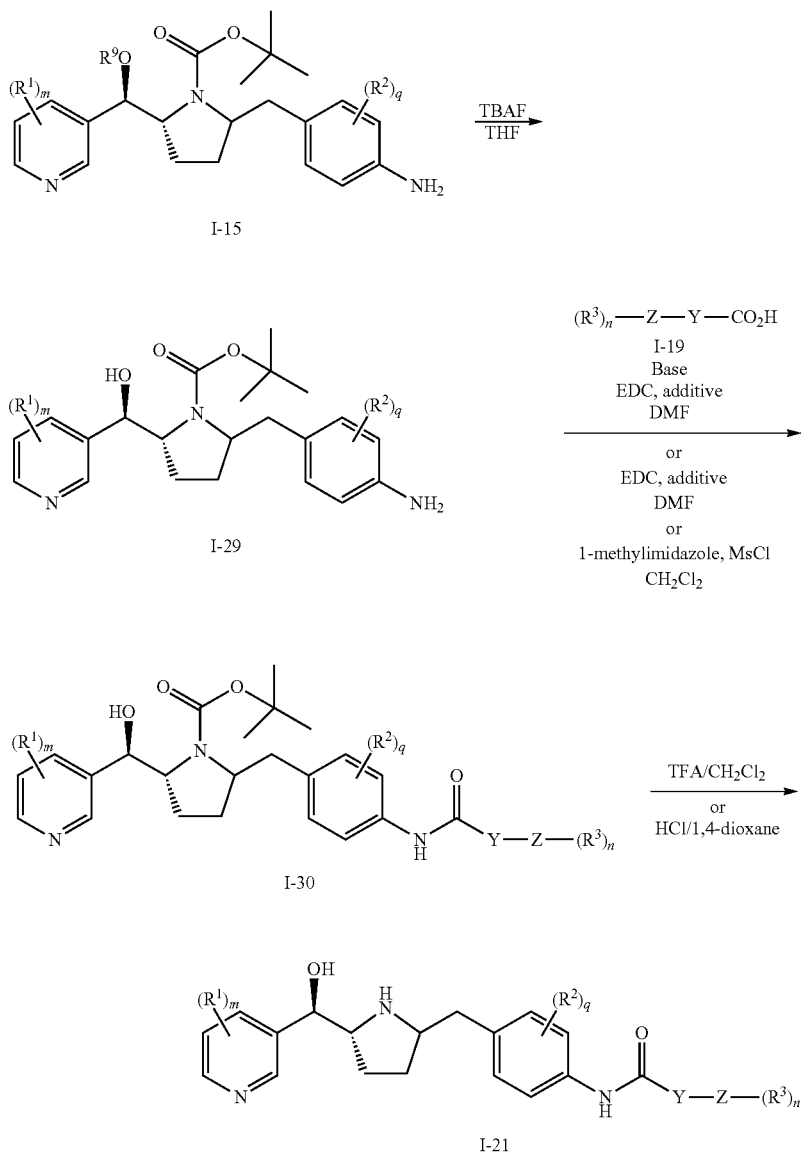

Scheme IX

Scheme X describes the preparation of amides of structural formula I-33 from either the cis- or trans-pyrrolidine intermediate I-29 by methods known to those skilled in the art. For example, bromination of I-29 via treatment with an N-bromosuccinimide solution in an inert organic solvent, such as DMF, affords alcohols of general structural formula I-31. The reaction is usually performed in an inert organic solvent such as DMF, between room temperature and 40° C., for a period of 5-24 h. Treatment of I-31 with the desired carboxylic acid I-19 in the presence of the appropriate amide coupling reagent, such as EDC, DCC, HATU or BOP, and the appropriate additive such as HOAT or HOBT, and either with or without a suitable organic base, such as N,N-diisopropylethylamine or triethylamine, affords amides of structural formula I-32. Alternatively, the desired carboxylic acid I-19 can be activated with methanesulfonyl chloride in the presence of 1-methylimidazole and reacted with I-31 to afford the desired amides of structural formula I-32. The reaction is usually performed in an inert organic solvent such as DMF, between room temperature and 50° C., for a period of 12-24 h. The carboxylic acids I-19 are either commercially available, known in the literature or readily prepared by methods commonly known to those skilled in the art. Removal of the Boc protecting groups of I-32 via treatment with a solution of TFA in an inert organic solvent, such as dichloromethane, at ambient temperature for a period of time between 1 and 6 h affords amides of formula I-33. Alternatively, treatment of I-32 with a solution of hydrogen chloride in an organic solvent, such as 1,4-dioxane or ethyl acetate, also yields the desired product of general structural formula I-33. Additional deprotection steps may be included if other protecting groups are present. These protecting groups may include trityl groups, tert-butylcarbamate groups or other groups suitable for the protection of heterocyclic compounds or the functional groups such as amines, hydroxyls, carboxylic acids or other groups known to those skilled in the art.

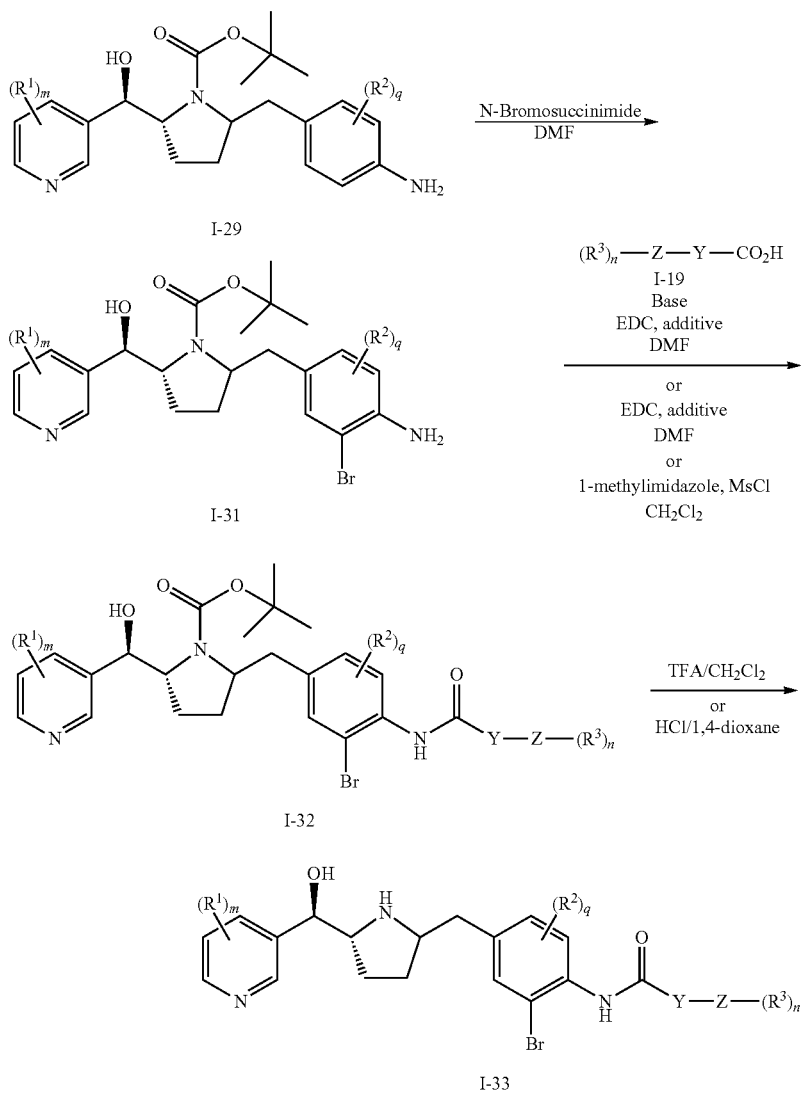

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

4-Methoxybenzyl{(1R)-1-[(R)-{[tert-butyl(dimethyl) silyl]oxy}(6-chloropyridin-3-yl)methyl]pent-4-yn-1-yl}carbamate (i-1)

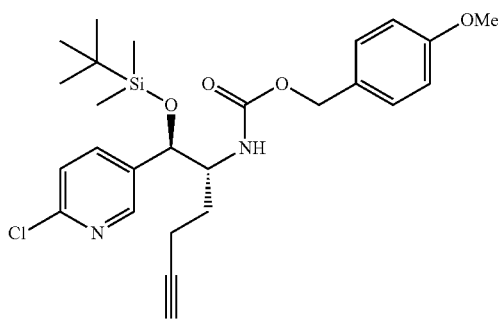 [SMILES: C#CCC[C@@H](NC(=O)OCc1ccc(OC)cc1)[C@H](O[Si](C)(C)C(C)(C)C)c1ccc(Cl)nc1]

Step A: (4S)-4-Benzyl-3-hex-5-ynoyl-1,3-oxazolidin-2-one

To a solution of 10 g (89 mmol) of 5-hexynoic acid and 31.0 mL (223 mmol) of triethylamine in 450 mL of anhydrous tetrahydrofuran at −25° C. under an atmosphere of nitrogen was added 12 mL (98 mmol) of trimethylacetyl chloride over 20 min. Upon addition a white precipitate formed and the resulting suspension was stirred for 2 h. Next, 4.2 g (98 mmol) of anhydrous lithium chloride and 17 g (94 mmol) of (S)-(−)-4-benzyl-2-oxazolidinone were added sequentially and the mixture was allowed to gradually warm to ambient temperature over 12 h. All volatiles were removed in vacuo and the residue was diluted with water (500 mL) and extracted with ether (3×200 mL). The combined organic layers were washed with brine (100 mL), dried over magnesium sulfate, filtered and concentrated in vacuo. The crude residue was purified by silica gel chromatography eluting with a 10-25% ethyl acetate in hexanes gradient to afford the title compound as a colorless solid (22 g, 93%). $^1$H NMR (500 MHz, CDCl$_3$): δ 7.35-7.31 (m, 2H), 7.28-7.25 (m, 1H), 7.19-7.21 (m, 2H), 4.69-4.64 (m, 1H), 4.22-4.15 (m, 2H), 3.28 (dd, J=13.4, 3.3 Hz, 1H), 3.13-3.01 (m, 2H), 2.78 (dd, J=13.4, 9.6 Hz, 1H), 2.34-2.30 (m, 2H), 1.99 (t, J=2.7 Hz, 1H), 1.96-1.88 (m, 2H). LC-MS: m/z (ES) 272.2 (MH)$^+$, 294.3 (MNa)$^+$.

Step B: (4S)-4-Benzyl-3-{(2R)-2-[(S)-(6-chloropyridin-3-yl)(hydroxy)methyl]hex-5-ynoyl}-1,3-oxazinan-2-one To a stirred solution of 23.0 g (837 mmol) of (4S)-4-benzyl-3-hex-5-ynoyl-1,3-oxazolidin-2-one from step A in 200 mL of anhydrous ethyl acetate at ambient temperature under an atmosphere of nitrogen was added 1.6 g (17 mmol) of anhydrous magnesium chloride, 23.0 mL (166 mmol) of triethylamine, 14.0 g (100 mmol) of 6-chloropyridine-3-carboxaldehyde and 16.0 mL (124 mmol) of chlorotrimethylsilane and the resulting mixture was stirred for 72 h. The heterogeneous reaction mixture was filtered through a 300 mL plug of silica gel eluting with an additional 1 L of ethyl acetate. The filtrate was evaporated to dryness in vacuo and the residue suspended in 200 mL of methanol and 5.0 mL of trifluoroacetic acid. The resulting mixture was stirred at ambient temperature under nitrogen for 5 h during which time the reaction became homogeneous. All volatiles were then removed in vacuo and the residue was purified by silica gel chromatography eluting with a 10-15% ethyl acetate in hexanes gradient to afford the title compound as a white solid (30 g, 88%). LC-MS: m/z (ES) 413.2 (MH)$^+$.

Step C: (4S)-4-Benzyl-3-{(2R)-2-[(S)-{[tert-butyl (dimethyl)silyl]oxy}(6-chloropyridin-3-yl)methyl] hex-5-ynoyl}-1,3-oxazinan-2-one To a stirred solution of 29.7 g (71.9 mmol) of (4S)-4-benzyl-3-{(2R)-2-[(S)-(6-chloropyridin-3-yl)(hydroxy)methyl]hex-5-ynoyl}-1,3-oxazinan-2-one from Step B and 15.0 mL (126 mmol) of 2,6-lutidine in 300 mL of anhydrous dichloromethane at 0° C. under an atmosphere of nitrogen was added 22 mL (94 mmol) of tert-butyldimethylsilyl trifluoromethanesulfonate at a rate slow enough to keep the internal temperature below 3° C. The reaction mixture was stirred for 16 h at 0° C. then evaporated in vacuo to remove all volatiles. The residue was diluted with 400 mL of water and extracted with diethyl ether (3×300 mL). The combined organics were washed sequentially with a 0.5 M aqueous hydrochloric acid solution (100 mL), water (100 mL) brine (100 mL) then dried over magnesium sulfate. After filtration and evaporation in vacuo the residue was purified by silica gel chromatography eluting with a 5-8% ethyl acetate in hexanes gradient to afford the title compound as a colorless foam (37 g, 97%). LC-MS: m/z (ES) 527.3 (MH)$^+$.

Step D: (2R)-2-[(S)-{[Tert-butyl(dimethyl)silyl]oxy} (6-chloropyridin-3-yl)methyl]hex-5-ynoic acid To a stirred solution of 37 g (70 mmol) of (4S)-4-benzyl-3-{(2R)-2-[(S)-{[tert-butyl(dimethyl)silyl]oxy}(6-chloropyridin-3-yl)methyl]hex-5-ynoyl}-1,3-oxazinan-2-one from Step C in 520 mL of a 3 to 1 mixture of anhydrous tetrahydrofuran to water at 0° C. under an atmosphere of nitrogen was added 30 mL (350 mmol) of a 35% aqueous hydrogen peroxide solution at a rate slow enough to keep the internal temperature below 3° C. Next, 140 mL (140 mmol) of a 1.0 M aqueous sodium hydroxide solution was added at a rate slow enough to keep the internal temperature of the reaction below 5° C. After complete addition the resulting mixture was stirred for 18 h at 0° C. then quenched with a solution of 350 mL (420 mmol) of a 1.2 M aqueous sodium sulfite solution at a rate slow enough to keep the internal temperature of the mixture below 15° C. All volatiles were removed in vacuo and the remaining aqueous phase was cooled to 0° C. and acidified with a 2.5 M aqueous hydrogen chloride solution until a pH of 3 was achieved. The aqueous phase was then extracted with ethyl acetate (3×200 mL) and the combined organics were washed with brine (10 ml), dried over magnesium sulfate, filtered and evaporated in vacuo. The residue was purified by silica gel chromatography eluting with 15% ethyl acetate and 3% acetic acid in hexanes to afford the title compound as a white solid (16 g, 62%). LC-MS: m/z (ES) 368.2 (MH)$^+$.

Step E: 4-Methoxybenzyl{(1R)-1-[(R)-{[tert-butyl (dimethyl)silyl]oxy}(6-chloropyridin-3-yl)methyl] pent-4-yn-1-yl}carbamate To a solution of 16 g (44 mmol) of (2R)-2-[(S)-{[tert-butyl (dimethyl)silyl]oxy}(6-chloropyridin-3-yl)methyl]hex-5- ynoic acid from Step D and 12 mL (87 mmol) of triethylamine in 150 mL of anhydrous toluene at ambient temperature under an atmosphere of nitrogen was added 10 mL (46 mmol) of diphenylphosphoryl azide. The mixture was stirred for 6 h and then 14.0 mL (109 mmol) of 4-methoxybenzyl alcohol was added. The resulting mixture was heated to 100° C. for 16 h, cooled to ambient temperature and then evaporated in vacuo to remove all volatiles. The crude residue was purified by silica gel chromatography eluting with 15% ethyl acetate in hexanes to afford the title compound (i-1) as a yellow foam (17 g, 78%). $^1$H NMR (500 MHz, CDCl$_3$): δ 8.28 (d, 2.0 Hz, 1H), 7.53 (dd, J=8.2, 2.3 Hz, 1H), 7.22 (d, J=8.4 Hz, 2H), 7.18 (d, J=8.2 Hz, 1H), 6.90 (d, J=8.4 Hz, 2H), 4.96-4.89 (m, 2H), 4.82 (d, J=2.5 Hz, 1H), 4.74 (d, J=9.6 Hz, 1H), 3.90-3.84 (m, 1H), 3.82 (s, 3H), 2.30-2.26 (m, 2H), 1.97 (t, J=2.5 Hz, 1H), 1.89-1.83 (m, 1H), 1.58-1.52 (m, 1H), 0.89 (s, 9H), 0.08 (s, 3H), −0.12 (s, 3H). LC-MS: m/z (ES) 503.3 (MH)$^+$.

INTERMEDIATE 2 AND INTERMEDIATE 3

5-{(R)-{[tert-butyl(dimethyl)silyl]oxy}[(2R,5S)-5-(4-nitrobenzyl)pyrrolidin-2-yl]methyl}-2-chloropyridine (i-2) and 5-{(R)-{[tert-butyl(dimethyl)silyl]oxy}[(2R,5R)-5-(4-nitrobenzyl)pyrrolidin-2-yl]methyl}-2-chloropyridine (i-3)

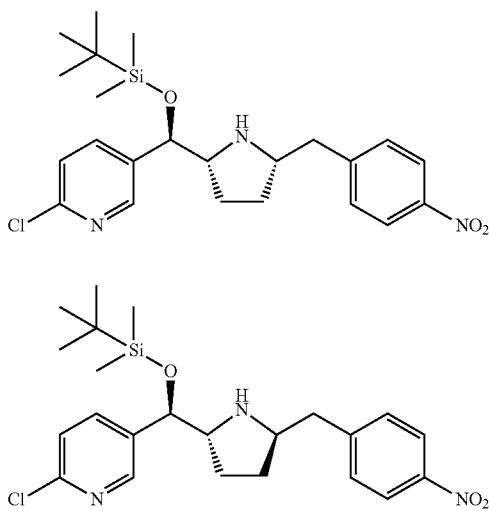

Step A: 4-Methoxybenzyl[(1R)-1-[(R)-{[tert-butyl(dimethyl)silyl]oxy}(6-chloropyridin-3-yl)methyl]-5-(4-nitrophenyl)pent-4-yn-1-yl]carbamate To a mixture of 9.2 g (37 mmol) of 4-iodonitrobenzene and 1.2 g (1.0 mmol) of tetrakis(triphenylphosphine)palladium (0) in 300 mL of anhydrous acetonitrile under an atmosphere of nitrogen was added copper(I)iodide 0.38 g (2.0 mmol). The resulting mixture was stirred at ambient temperature for 15 min then 16.8 g (33.4 mmol) of Intermediate 1 was added followed by 47.0 mL (334 mmol) of triethylamine. The reaction was stirred at ambient temperature for 15 h then evaporated to remove all volatiles. The residue was diluted with 100 mL of a saturated aqueous sodium bicarbonate solution and the aqueous suspension was extracted with diethyl ether (3×100 mL). The combined organic layers were washed with water (50 mL) and brine (50 ml), dried over magnesium sulfate, filtered and evaporated in vacuo. The residue was purified by silica gel chromatography eluting with 15% ethyl acetate in hexanes to afford the title compound as a yellow solid (18 g, 84%). LC-MS: m/z (ES) 624.4 (MH)$^+$.

Step B: 4-Methoxybenzyl[(1R)-1-[(R)-{[tert-butyl(dimethyl)silyl]oxy}(6-chloropyridin-3-yl)methyl]-5-(4-nitrophenyl)-4-oxopentyl]carbamate To 17.5 g (28.0 mmol) of 4-methoxybenzyl[(1R)-1-[(R)-{[tert-butyl(dimethyl)silyl]oxy}(6-chloropyridin-3-yl)methyl]-5-(4-nitrophenyl)pent-4-yn-1-yl]carbamate from Step A in 100 mL of anhydrous N,N-dimethylformamide under an atmosphere of nitrogen was added 7.0 mL (84 mmol) of pyrrolidine. The resulting mixture was heated to 80° C. for 5 h. After cooling to ambient temperature, 5 mL of a 10% aqueous acetic acid solution was added and the resulting mixture stirred for 3 h. All volatiles were then removed in vacuo and the residue diluted with 500 mL of a saturated aqueous sodium bicarbonate solution and 200 mL of diethyl ether. The layers were separated and the aqueous phase extracted with diethyl ether (2×200 mL). The combined organic layers were washed with water (50 mL) then brine (50 ml), dried over magnesium sulfate, filtered and evaporated in vacuo to afford the title compound as a yellow gum (18 g, >99%) that was used without further purification. LC-MS: m/z (ES) 642.3 (MH)$^+$.

Step C: 5-{(R)-{[Tert-butyl(dimethyl)silyl]oxy}[(2R)-5-(4-nitrobenzyl)-3,4-dihydro-2H-pyrrol-2-yl]methyl}-2-chloropyridine To a stirred solution of 18 g (28 mmol) of 4-methoxybenzyl[(1R)-1-[(R)-{[tert-butyl(dimethyl)silyl]oxy}(6-chloropyridin-3-yl)methyl]-5-(4-nitrophenyl)-4-oxopentyl]carbamate from Step B in 75 mL of anhydrous dichloromethane was added 75 ml of trifluoroacetic acid. The resulting mixture was stirred at ambient temperature for 2 h during which time the reaction became dark red in color. All volatiles were removed in vacuo and the residue dissolved in 300 mL of dichloromethane. The solution was washed with a saturated aqueous sodium bicarbonate solution (2×100 mL), brine (100 ml) and then dried over magnesium sulfate and filtered. All volatiles were evaporated in vacuo to afford the title compound as a dark red gum (13 g, >99%) that was used immediately without further purification. LC-MS: m/z (ES) 460.4 (MH)$^+$.

Step D: 5-{(R)-{[tert-butyl(dimethyl)silyl]oxy}[(2R,5S)-5-(4-nitrobenzyl)pyrrolidin-2-yl]methyl}-2-chloropyridine and 5-{(R)-{[tert-butyl(dimethyl)silyl]oxy}[(2R,5R)-5-(4-nitrobenzyl)pyrrolidin-2-yl]methyl}-2-chloropyridine To a stirred suspension of 13 g (28 mmol) of 5-{(R)-{[tert-butyl(dimethyl)silyl]oxy}[(2R)-5-(4-nitrobenzyl)-3,4-dihydro-2H-pyrrol-2-yl]methyl}-2-chloropyridine from Step C in 200 mL of anhydrous methanol at 0° C. under an atmosphere of nitrogen was added 12 g (190 mmol) of sodium cyanoborohydride and the resulting mixture was stirred for 6 h. The reaction mixture was quenched at 0° C. by slow addition of 150 mL of water followed by evaporation of all volatile organics in vacuo. The remaining aqueous phase was then extracted with ethyl acetate (3×150 mL) and the combined organic layers were washed with water (50 mL) then brine (50 ml), dried over magnesium sulfate, filtered and evaporated in vacuo. The crude residue was purified by silica gel chromatography eluting with a 5-10% acetone in hexanes gradient to afford the two title compounds.

First spot to elute (i-2—cis isomer): 5-{(R)-{[tert-butyl(dimethyl)silyl]oxy}[(2R,5S)-5-(4-nitrobenzyl)pyrrolidin-2-yl]methyl}-2-chloropyridine is a yellow gum (6.5 g, 50%): $^1$H NMR (500 MHz, CDCl$_3$): δ 8.31 (d, J=2.3 Hz, 1H), 8.13 (d, J=8.7 Hz, 2H), 7.62 (dd, J=8.2, 2.3 Hz, 1H), 7.36 (d, J=8.7 Hz, 2H), 7.27 (d, J=8.5 Hz, 1H), 4.45 (d, J=6.9 Hz, 1H), 3.32-3.27 (m, 1H), 3.19-3.14 (m, 1H), 2.83 (dd, J=13, 5.0 Hz, 1H), 2.72 (dd, J=13, 8.0 Hz, 1H), 1.90 (br s, 114), 1.79-1.72 (m, 1H), 1.42-1.38 (m, 2H), 1.31-1.24 (m, 1H), 0.82 (s, 9H), 0.19 (s, 3H), −0.15 (s, 3H). LC-MS: m/z (ES) 462.5 (MH)$^+$.

Second spot to elute (i-3—trans isomer): 5-{(R)-{[tert-butyl(dimethyl)silyl]oxy}[(2R,5R)-5-(4-nitrobenzyl)pyrrolidin-2-yl]methyl}-2-chloropyridine is a yellow gum (0.65 g, 5.0%): $^1$H NMR (500 MHz, CDCl$_3$): δ 8.26 (d, J=2.1 Hz, 1H), 8.15 (d, J=8.5 Hz, 2H), 7.60 (dd, J=8.2, 2.3 Hz, 1H), 7.36 (d, J=8.5 Hz, 2H), 7.28 (d, J=8.2 Hz, 1H), 4.31 (d, J=7.6 Hz, 1H), 3.38-3.30 (m, 2H), 2.86 (dd, J=13.2, 5.2 Hz, 1H), 2.73 (dd, J=13.2, 8.5 Hz, 1H), 1.93-1.87 (m, 1H), 1.82 (br s, 1H), 1.69-1.62 (m, 1H), 1.49-1.41 (m, 1H), 1.39-1.32 (m, 1H), 0.75 (s, 9H), −0.12 (s, 3H), −0.27 (s, 3H). LC-MS: m/z (ES) 462.5 (MH)$^+$.

INTERMEDIATE 4

Tert-butyl(2S,5R)-2-(4-aminobenzyl)-5-[(R)-{[tert-butyl(dimethyl)silyl]oxy}(pyridin-3-yl)methyl]pyrrolidine-1-carboxylate (i-4)

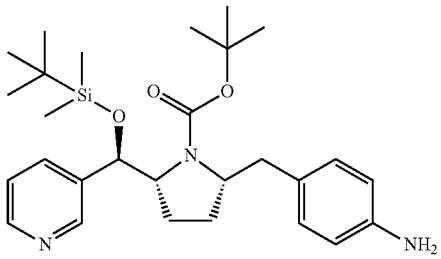 [SMILES: CC(C)(C)OC(=O)N1[C@H](Cc2ccc(N)cc2)CC[C@@H]1[C@H](O[Si](C)(C)C(C)(C)C)c1cccnc1]

Step A: Tert-butyl(2R,5S)-2-[(R)-{[tert-butyl(dimethyl)silyl]oxy}(6-chloropyridin-3-yl)methyl]-5-(4-nitrobenzyl)pyrrolidine-1-carboxylate To a stirred solution of 6.5 g (14 mmol) of i-2 in 100 mL of anhydrous dichloromethane at ambient temperature under an atmosphere of nitrogen was added 4.9 mL (21 mmol) of diisopropylethylamine followed by 3.6 g (28 mmol) of di-tert-butyl dicarbonate and the resulting mixture was stirred for 4 h. The reaction mixture was evaporated to dryness in vacuo and the crude residue purified by silica gel chromatography eluting with a 5-10% ethyl acetate in hexanes gradient to afford the title compound as a colorless gum (6.4 g, 81%). LC-MS: m/z (ES) 562.3 (MH)$^+$.

Step B: Tert-butyl(2S,5R)-2-(4-aminobenzyl)-5-[(R)-{[tert-butyl(dimethyl)silyl]oxy}(pyridine-3-yl)methyl]pyrrolidine-1-carboxylate To 0.70 g (0.66 mmol) of 10% palladium on carbon was added a solution of 6.4 g (11 mmol) of tert-butyl(2R,5S)-2-[(R)-{[tert-butyl(dimethyl)silyl]oxy}(6-chloropyridin-3-yl)methyl]-5-(4-nitrobenzyl)pyrrolidine-1-carboxylate from Step A in 75 mL of anhydrous ethanol followed by 1.2 g (12 mmol) of potassium acetate. The resulting suspension was agitated under an atmosphere of hydrogen at 50 psi for 8 h. then filtered through a plug of Celite®. The plug was washed with ethanol (100 mL) and the combined filtrates were concentrated in vacuo. The residue was purified by silica gel chromatography eluting with 40% ethyl acetate in hexanes to afford the title compound as a colorless solid (0.31 g, 76%). LC-MS: m/z (ES) 498.4 (MH)$^+$.

INTERMEDIATE 5

Tert-butyl(2R,5R)-2-(4-aminobenzyl)-5-[(R)-{[tert-butyl(dimethyl)silyl]oxy}(pyridin-3-yl)methyl]pyrrolidine-1-carboxylate (i-5)

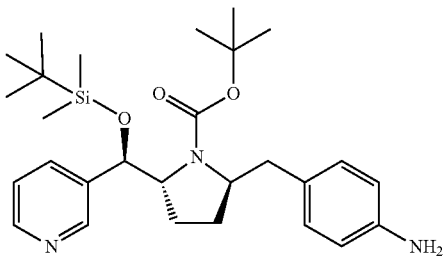 [SMILES: CC(C)(C)OC(=O)N1[C@@H](Cc2ccc(N)cc2)CC[C@@H]1[C@H](O[Si](C)(C)C(C)(C)C)c1cccnc1]

Step A: Tert-butyl(2R,5R)-2-[(R)-{[tert-butyl(dimethyl)silyl]oxy}(6-chloropyridin-3-yl)methyl]-5-(4-nitrobenzyl)pyrrolidine-1-carboxylate To a stirred solution of 0.27 g (0.58 mmol) of i-3 in 10 mL of anhydrous dichloromethane at ambient temperature under an atmosphere of nitrogen was added 0.25 mL (1.4 mmol) of diisopropylethylamine followed by 0.19 g (1.4 mmol) of di-tert-butyl dicarbonate and the resulting mixture was stirred for 4 h. The reaction mixture was evaporated to dryness in vacuo and the crude residue purified by silica gel chromatography eluting with a 5-10% ethyl acetate in hexanes gradient to afford the title compound as a colorless gum (0.14 g, 42%). LC-MS: m/z (ES) 562.3 (MH)$^+$.

Step B: Tert-butyl(2R,5R)-2-(4-aminobenzyl)-5-[(R)-{[tert-butyl(dimethyl)silyl]oxy}(pyridin-3-yl)methyl]pyrrolidine-1-carboxylate To 0.020 g (0.024 mmol) of 10% palladium on carbon was added a solution of 0.14 g (0.24 mmol) of tert-butyl (2R,5R)-2-[(R)-{[tert-butyl(dimethyl)silyl]oxy}(6-chloropyridin-3-yl)methyl]-5-(4-nitrobenzyl)pyrrolidine-1-carboxylate from Step A in 4 mL of anhydrous ethanol followed by 0.024 g (0.24 mmol) of potassium acetate. The resulting suspension was agitated under an atmosphere of hydrogen at 50 psi for 8 h. then filtered through a plug of Celite®. The plug was washed with ethanol (10 mL) and the combined filtrates were concentrated in vacuo. The residue was purified by silica gel chromatography eluting with 40% ethyl acetate in hexanes to afford the title compound as a colorless solid (0.065 g, 54%). LC-MS: m/z (ES) 498.4 (MH)$^+$.

INTERMEDIATE 6

(2S)-1-(1,3-thiazol-2-yl)pyrrolidine-2-carboxylic acid (i-6)

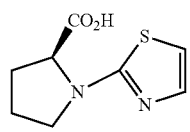 [SMILES: O=C(O)[C@@H]1CCCN1c1nccs1]

To a solution of 80 mg (0.70 mmol) of L-Proline in 3 mL of anhydrous N,N-dimethylformamide at ambient temperature was added 0.062 ml (0.70 mmol) of 2-bromothiazole, 288 mg (2.09 mmol) of potassium carbonate, and 13 mg (0.068 mmol) of copper(I)iodide. The reaction mixture was heated to 100° C. overnight then filtered through a plug of Celite®. The crude residue was purified by reverse-phase HPLC (TMC Pro-Pac C18; 0-60% 0.1% trifluoroacetic acid in acetonitrile/ 0.1% trifluoroacetic acid in water gradient). The pure fractions were lyophilized overnight to give the title compound as a light brown solid. (0.065 g, 50%). LC-MS: m/z (ES) 199.2 $(MH)^+$.

INTERMEDIATE 7

(2S)-1-(3-methoxyphenyl)pyrrolidine-2-carboxylic acid

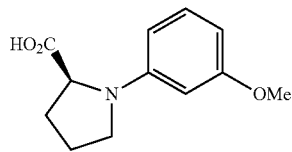 [SMILES: COc1cccc(N2CCC[C@H]2C(=O)O)c1]

Intermediate 7 was prepared using a procedure similar to that described above for Intermediate 6 (i-6).

INTERMEDIATE 8

2-Methyl-5,6-dihydro-4H-cyclopenta[d][1,3]thiazole-4-carboxylic acid (i-8)

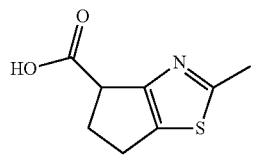

Step A: Ethyl 2-methyl-5,6-dihydro-4H-cyclopenta[d][1,3]thiazole-4-carboxylate

To a cooled (0° C.) solution of 56.0 g (359 mmol) of ethyl 2-oxocyclopentane-2-carboxylate in chloroform (500 mL) was added 8.5 mL (359 mmol) of neat bromine over a 20 min period. After complete addition the reaction mixture allowed to warm to ambient temperature and stirred overnight. Nitrogen gas was then bubbled through the mixture for 90 min to remove the hydrogen bromide generated during the reaction. The organic phase was then washed with 500 mL of water, 250 mL of a saturated aqueous sodium bicarbonate solution and finally 200 mL of brine. The organic phase was then dried over magnesium sulfate, filtered and evaporated in vacuo. The crude residue was next dissolved in 500 mL of EtOH and 26.9 g (359 mmol) of solid thioacetamide was added. The resulting mixture was stirred at ambient temperature for 1 h then at reflux overnight. The mixture was cooled, evaporated in vacuo, and the residue partitioned between dichloromethane and a saturated aqueous sodium bicarbonate solution. The layers were separated and the organic phase was washed with brine, dried over magnesium sulfate, filtered and evaporated in vacuo. The crude residue was purified by MPLC (Biotage Horizon: 2×FLASH 65i) eluent: 100% Hexanes (450 ml), gradient rising from 100% Hexanes to 25% EtOAc in hexanes (1400 ml), then 25% EtOAc in hexanes to give the title compound as a dark oil. $^1$H NMR (500 MHz, CDCl$_3$) δ: 4.22 (q, J=7.0 Hz, 2H), 3.96 (m, 1H), 3.04 (m, 1H), 2.88 (m, 1H), 2.76 (m, 2H), 2.70 (s, 3H), 1.30 (t, J=7.0 Hz, 3H).

Step B: 2-Methyl-5,6-dihydro-4H-cyclopenta[d][1,3]thiazole-4-carboxylic acid

To a solution of 31.5 g (149 mmol) of ethyl 2-methyl-5,6-dihydro-4H-cyclopenta[d][1,3]thiazole-4-carboxylate from step A in a mixture of 450 mL of anhydrous THF and 100 mL of methanol was added a solution of 149 mL of a 1.0 M solution (149 mmol) of lithium hydroxide. The resulting mixture stirred at room temperature for 3 h and then the volatile organics were evaporated in vacuo. The aqueous residue was extracted with Et$_2$O (2×250 ml.) and then acidified to pH=3 with 170 mL of a 1.0 N hydrochloric acid solution. The solution was saturated with solid sodium chloride and then extracted with dichloromethane (3×250 mL). The combined organic layers were dried over magnesium sulfate, filtered and evaporated in vacuo. The crude residue was then triturated with acetonitrile, filtered and dried under vacuum to give the title compound as an off white solid. $^1$HNMR (500 MHz, CDCl$_3$) δ: 11.75 (br s, 1H), 4.02 (m, 1H), 3.00 (m, 1H), 2.90-2.66 (m, 6H).

INTERMEDIATES 9-12

Intermediates 9 (i-9) through 12 (i-12) were prepared using a procedure analogous to that used in the preparation of Intermediate 8. Step A was modified by substituting the appropriate thioamide in place of thioacetamide.

TABLE 1

| INTERMEDIATE | R |
|---|---|
| i-9 | Me |

TABLE 1-continued

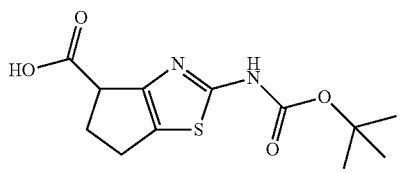 [SMILES: CC(C)(C)OC(=O)Nc1nc2c(s1)CCC2C(=O)O]

| INTERMEDIATE | R |
|---|---|
| i-10 | cyclopropyl |
| i-11 | isopropyl (CHMe₂) |
| i-12 | CH₂OMe |

INTERMEDIATE 13

2-[(Tert-butoxycarbonyl)amino]-5,6-dihydro-4H-cyclopenta[d][1,3]thiazole-4-carboxylic acid (i-13)

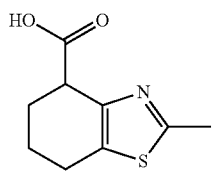

Step A: Ethyl 2-amino-5,6-dihydro-4H-cyclopenta[d][1,3]thiazole-4-carboxylate Prepared using a procedure analogous to that found in Step A of Intermediate 8 which was modified by replacing thioacetamide with thiourea. $^1$H NMR (500 MHz, CDCl$_3$) δ: 5.30 (br s, 2H), 4.21 (q, J=7.0, 2H), 3.81 (m, 1H), 2.91 (m, 1H), 2.78 (m, 1H), 2.66 (m, 2H), 1.30 (t, J=7.0, 3H).

Step B: Ethyl 2-[(tert-butoxycarbonyl)amino]-5,6-dihydro-4H-cyclopenta[d][1,3]thiazole-4-carboxylate To a solution of 0.230 g (1,08 mmol) of ethyl 2-amino-5,6-dihydro-4H-cyclopenta[d][1,3]thiazole-4-carboxylate from step A in 5 mL of dichloromethane was added 0.236 g (1.08 mmol) of di-tert butyl dicarbonate, 0.15 mL (1.08 mmol) of triethylamine and 0.013 g (0.11 mmol) of N,N-dimethylamino pyridine and the resulting mixture was stirred at ambient temperature for 2 h. The reaction was washed with 10 mL of a 1.0 N hydrochloric acid solution, 5 mL of brine, dried over magnesium sulfate, filtered and evaporated in vacuo. The crude residue was purified by MPLC (Biotage Horizon: FLASH 25+S) eluent: 100% Hexanes (100 ml), gradient 0-15% EtOAc in Hexanes (900 ml) then 15% EtOAc in Hexanes (500 ml) to give the title compound as a white foam. $^1$H NMR (500 MHz, CDCl$_3$) δ: 9.23 (br s, 1H), 4.17 (q, J=7.1 Hz, 2H), 3.95 (t, J=6.6 Hz, 1H), 3.04 (m, 1H), 2.86 (m, 1H), 2.76 (m, 2H), 1.55 (s, 9H), 1.23 (t, J=7.1 Hz, 3H).

Step C: 2-[(Tert-butoxycarbonyl)amino]-5,6-dihydro-4H-cyclopenta[d][1,3]thiazole-4-carboxylic acid Prepared from ethyl 2-[(tert-butoxycarbonyl)amino]-5,6-dihydro-4H-cyclopenta[d][1,3]thiazole-4-carboxylate of Step B above using a procedure analogous to that found in Step B of Intermediate 8. $^1$H NMR (500 MHz, CDCl$_3$) δ: 3,96 (m, 1H), 3.06 (m, 1H), 2.88 (m, 2H), 2.71 (m, 1H), 1.55 (s, 9H).

INTERMEDIATE 14

2-Methyl-4,5 6,7-tetrahydro-1,3-benzothiazole-4-carboxylic acid (i-14)

Step A: Ethyl 2-methyl-4,5,6,7-tetrahydro-1,3-benzothiazole-4-carboxylate

To a solution of 15 g (88 mmol) of ethyl 2-oxocyclohexanecarboxylate in 40 mL of anhydrous diethyl ether cooled to 0° C. was added 4.5 mL (88 mmol) of bromine dropwise over 15 min. After complete addition the mixture was allowed to warm to ambient temperature over 90 min. The mixture was next diluted with 100 mL of ethyl acetate and washed with a saturated aqueous sodium bicarbonate solution, brine, dried over magnesium sulfate, filtered and evaporated in vacuo. The residue was taken up in 100 mL of ethanol and 6.6 g (88 mmol) of thioacetamide was added. The mixture was stirred at ambient temperature for 1 h, then at reflux overnight. After evaporation of all volatiles in vacuo the residue was partitioned between a saturated aqueous sodium bicarbonate solution and dichloromethane. The layers were separated and the organic phase was dried over magnesium sulfate and evaporated in vacuo. The crude residue was purified by MPLC (Biotage Horizon: FLASH 65i) eluent: 100% Hexanes (500 ml), gradient 0 to 25% EtOAc in hexanes (1200 ml) then 25% EtOAc in hexanes (1200 ml) to give the title compound as a pale orange oil. $^1$H NMR (500 MHz, CDCl$_3$) δ: 4.22 (q, J=7.1, 2H), 3.84 (t, J=5.5, 1H), 2.80 (m, 1H), 2.73 (m, 1H), 2.65 (s, 3H), 2.18 (m, 1H), 2.11-1.95 (m, 2H), 1.85 (m, 1H), 1.29 (t, J=7.1, 3H).

Step B: 2-Methyl-4,5,6,7-tetrahydro-1,3-benzothiazole-4-carboxylic acid

Prepared from ethyl 2-methyl-4,5,6,7-tetrahydro-1,3-benzothiazole-4-carboxylate from Step A above using a procedure analogous to that found in Step B of Intermediate 8. $^1$H NMR (500 MHz, CDCl$_3$) δ: 9.26 (br s, 1H), 3.81 (q, J=7.3 and 5.9, 1H), 2.75 (m, 2H), 2.68 (s, 3H), 2.24 (m, 1H), 2.18-2.01 (m, 2H), 1.82 (m, 1H).

INTERMEDIATE 15

6,7-Dihydro-5H-cyclopenta[b]pyridine-7-carboxylic acid, trifluoroacetic acid salt (i-15)

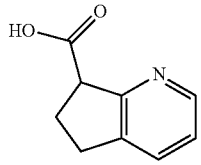 [SMILES: O=C(O)C1CCc2cccnc21]

To a cooled (0° C.) solution of 16 mL (25 mmol) of a 1.6 M n-butyl lithium solution in hexanes was added 3.9 mL (25 mmol) of N,N,N',N'-tetramethylethylenediamine followed by a solution of 3.0 mL (25 mmol) of 2,3,-cyclopentenopyridine in 5 mL of anhydrous tetrahydrofuran. The resulting mixture was allowed to warm to ambient temperature over 15 min and then anhydrous carbon dioxide gas was bubbled through the reaction mixture for 1 h. The solid precipitate was next filtered and the crude solid purified by reverse phase HPLC (TMC Pro-Pac C18; 0-40% 0.1% trifluoroacetic acid in acetonitrile/0.1% trifluoroacetic acid in water gradient) to give the title compound as a yellow solid. LC-MS: m/z (ES) 164.1 (MH)$^+$.

INTERMEDIATE 16

4-{4-[4-(Trifluoromethyl)phenyl]-1,3-thiazol-2-yl}benzenesulfonyl chloride (i-16)

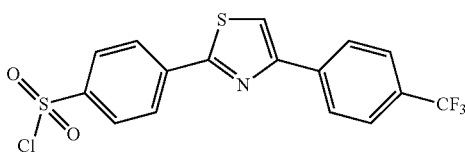 [SMILES: O=S(=O)(Cl)c1ccc(-c2nc(-c3ccc(C(F)(F)F)cc3)cs2)cc1]

Intermediate 16 was prepared according to published procedures. See Ikemoto et al., *Tetrahedron* 2003, 59, 1317-1325.

INTERMEDIATE 17

Tert-butyl(2S,5R)-2-4-aminobenzyl)-5-[(R)-hydroxy(pyridin-3-yl)methyl]pyrrolidine-1-carboxylate (i-17)

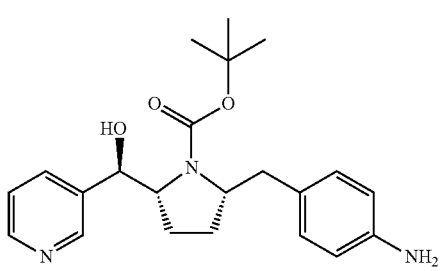 [SMILES: CC(C)(C)OC(=O)N1[C@H](Cc2ccc(N)cc2)CC[C@@H]1[C@H](O)c1cccnc1]

To a stirred solution of 30.0 g (60.3 mmol) of Intermediate 4 (tert-butyl(2S,5R)-2-(4-aminobenzyl)-5-[(R)-{[tert-butyl(dimethyl)yl]oxy}(pyridine-3-yl)methyl]pyrrolidine-1-carboxylate) in 100 mL of THF was added 90 mL (90 mmol) of a 1.0 M solution of tetrabutylammonium fluoride in THF. The resulting mixture was stirred for 7 h then diluted with 200 mL of water. The layers were separated and the aqueous phase extracted with ethyl acetate (3×100 mL). The combined organics were washed with brine, dried over magnesium sulfate, filtered, and evaporated to dryness in vacuo. The crude residue was purified by silica gel chromatography eluting with a 40-80% gradient of ethyl acetate in hexanes to afford the title compound as a white foam (20 g, 87%). $^1$H NMR (500 MHz, CDCl$_3$): δ 8.51-8.49 (m, 2H), 7.72 (d, J=7.4 Hz, 1H), 7.28-7.25 (m, 1H), 6.96 (d, J=8.2 Hz, 2H), 6.64 (d, J=8.2 Hz, 2H), 6.43 (br s, 1H), 4.41-4.40 (m, 1H), 4.10-4.02 (m, 2H), 3.46 (br s, 2H), 2.92-2.88 (m, 1H), 2.50 (dd, J=13.3, 8.5 Hz, 1H), 1.72-1.60 (m, 3H), 1.51 (s, 9H), 1.48-1.38 (m, 1H). LC-MS: m/z (ES) 384(MH)$^+$.

INTERMEDIATE 18

5,6-Dihydro-4H-pyrrolo[1,2-b]pyrazole-6-carboxylic acid (i-18)

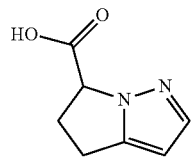

Step A: 7-(Trimethylsilyl)-5-oxohept-6-ynoic acid

This intermediate was prepared according to the known experimental procedure found in: Nayyar, N. K.; Hutchison, D. R.; Martinelli, M. J. *J. Org. Chem.* 1997, 62, 982.

Step B: (5Z)-5-[(Tert-butoxycarbonyl)hydrazono]-7-(trimethylsilyl)hept-6-ynoic acid To a stirred solution of 54.0 g (254 mmol) of 7-(trimethylsilyl)-5-oxohept-6-ynoic acid from step A in 750 mL of IPA under an atmosphere of nitrogen was added 33.6g (254 mmol) of tert-butyl carbazate. The reaction mixture was stirred for 4 h at ambient temperature then evaporated in vacuo to remove all volatiles. This afforded the title compound as a yellow gum which was used without further purification (77 g, 93%). LC-MS: m/z (ES) 327 (MH)$^+$.

Step C: 4-[1-(Tert-butoxycarbonyl)-1H-pyrazol-3-yl]butanoic acid

To a stirred solution of 77.0 g, (236 mmol) of (5Z)-5-[(tert-butoxycarbonyl)hydrazono]-7-(trimethylsilyl)hept-6-ynaic acid from step B in 500 mL of THF was added 350 ml (350 mmol) of a 1.0 M solution of tetrabutylammonium fluoride in THF over 30 min. The resulting mixture was stirred at ambient temperature for 48 h. and then evaporated to dryness in vacuo. The residue was diluted with 1 L of a 5% aqueous acetic acid solution and the aqueous phase extracted with ethyl acetate (3×350 mL). The combined organic layers were washed with water (2×100 mL), and brine (150 mL), dried over magnesium sulfate, filtered and avaporated to dryness in vacuo. The crude residue was purified by silica gel chromatography eluting with 3% acetic acid and 35% ethyl acetate in hexanes mixture to afford the title compound as yellow oil (60 g, quantitative yield). LC-MS: m/z (ES) 255 (MH)$^+$.

Step D: Tert-butyl 3-[4-(benzyloxy)-4-oxobutyl]-1H-pyrazole-1-carboxylate

To a stirred solution of 60.0 g (236 mmol) of 4-[1-(tert-butoxycarbonyl)-1H-pyrazol-3-yl]butanoic acid from step C in 400 mL of DMF was added 48.9 g (354 mmol) of potassium carbonate followed by dropwise addition of 40.0 mL (300 mmol) of benzyl bromide. The resulting mixture was stirred for 24 h, quenched with water, and extracted with ethyl acetate (3×300 mL). The combined organic layers were washed (Brine), dried over magnesium sulfate, filtered and evaporated to dryness in vacuo. The crude residue was purified by silica gel chromatography eluting with 30% EtOAc in hexanes to afford the title compound as a yellow oil (55.6 g, 68.4%). LC-MS: m/z (ES) 345 (MH)$^+$.

Step E: Tert-butyl 3-[4-(benzyloxy)-3-bromo-4-oxobutyl]-1H-pyrazole-1-carboxylate To a stirred solution of 27.5 g (80.0 mmol) of tert-butyl 3-[4-(benzyloxy)-4-oxobutyl]-1H-pyrazole-1-carboxylate from step D in 250 mL of anhydrous THF at −78° C. under an atmosphere of nitrogen was added 88 mL (88 mmol) of a 1.0 M solution of sodium bis(trimethylsilyl)amide in anhydrous THF. The resulting dark yellow solution was stirred for 1 h at −78° C. and then 12 ml (96 mmol) of chlorotrimethylsilane was added dropwise over 5 min. The resulting mixture was stirred for 25 min during which time the reaction became a light yellow color. Next, 16 g (88 mmol) of solid N-bromosuccinimide was added in one portion and the resulting mixture was stirred for 3 hrs at −78° C. followed by gradual warming to 0° C. over 1 h. The reaction was quenched with a saturated aqueous ammonium chloride solution and the aqueous phase extracted with ethyl acetate (3×200 mL). The combined organics were washed with brine, dried over magnesium sulfate, filtered and evaporated to dryness in vacuo to afford the title compound as a yellow gum. The crude product appears to be a 1:1 mixture of starting material and desired product by NMR and was used without further purification in the next step. LC-MS: m/z (ES) 424 (MH)$^+$.

Step F: Benzyl 5,6-dihydro-4H-pyrrolo[1,2-b]pyrazole-6-carboxylate

To a stirred solution of 16.9 g (40.0 mmol) of text-butyl 3-[4-(benzyloxy)-3-bromo-4-oxobutyl]-1H-pyrazole-1-carboxylate from step E in 50 mL of dichlormethane was added 50 mL of TFA. The resulting mixture was stirred for 2 h at ambient temperature then all volatiles were evaporated in vacuo. The residue was then diluted with 50 mL of toluene and evaporated again in vacuo to remove all residual TFA. The crude material was then dissolved in 125 mL of anhydrous acetone and 14.0 g (100 mmol) of solid potassium carbonate was slowly added over 15 min followed by 1.2 g (8.0 mmol) of sodium iodide. The resulting mixture was then heated at reflux for 16 h, cooled to room temperature and evaporated to dryness in vacuo. The residue was diluted with 100 mL of a saturated, aqueous ammonium chloride solution and then extracted with ethyl acetate (3×100 mL). The combined organics layers were washed with brine, dried over magnesium sulfate, filtered and evaporated in vacuo. The crude residue was purified by silica gel chromatography eluting with a 10-80% EtOAc in hexanes gradient to afford the title compound as a clear gum 6.2 g (64% yield). LC-MS: m/z (ES) 243 (MH)$^+$.

Step G: 5,6-Dihydro-4H-pyrrolo[1,2-b]pyrazole-6-carboxylic acid

A 100 mL round bottom flask under an atmosphere of nitrogen was charged with 0.600 mg (0.560 mmol) of 10 weight percent palladium on activated carbon and wet with 10 ml of ethanol. Next, a solution of 6.0 g (0.025 mol) of benzyl 5,6-dihydro-4H-pyrrolo[1,2-b]pyrazole-6-carboxylate from step F in 40 mL of ethanol was added and the mixture placed under 1 atmosphere of hydrogen. The reaction was stirred for 3 h then filtered through a pad of Celite®. The pad was washed with 20 mL of ethanol and the filtrate was evaporated in vacuo to afford the title compound as a colorless solid (3.7 g, quantitative yield). $^1$H NMR (500 MHz, DMSO-d$_6$): δ 11.90 (br s, 1H), 7.44 (s, 1H), 5.98 (s, 1H), 4.87 (dd, J=8.9, 3.7 Hz, 1H), 2.94-2.82 (m, 3H), 2.58-2.52 (m, 1H). LC-MS: m/z (ES) 153 (MH)$^+$.

INTERMEDIATE 19

2-(2-benzylamino)-2-oxoethyl)-5,6-dihydro-4H-cyclopenta[d]thiazole-4-carboxylic acid (i-19)

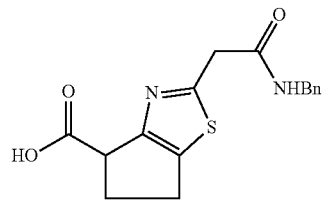

Intermediate 19 was prepared according to the procedure used for Intermediate 8 except that 3-amino-N-benzyl-3-thioxopanamide was used in place of thioacetamide. LC-MS: m/z (E/S) 317 (MH)$^+$.

INTERMEDIATE 20

4-Chloro-5-pyrimidinyl acetic acid (i-20)

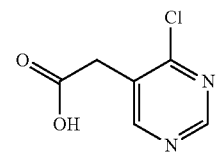 [SMILES: O=C(O)Cc1cncnc1Cl]

Step A: Ethyl(4-chloro-5-pyrimidinyl)acetate

This material was synthesized according to the procedure of Zymalkowski and Reimann et al, *Archiv. Der. Pharmazie* 1966, 299, 362.

Step B: 4-Chloro-5-pyrimidinyl acetic acid

To a solution of 0.6 g (3 mmol) of ethyl(4-chloro-5-pyrimidinyl)acetate from Step A in 0.5 mL of water and 1.5 mL of ethanol was added 215 mg (5.11 mmol) of lithium hydroxide hydrate. The reaction mixture was stirred at ambient temperature for 2 h then concentrated in vacuo to remove all volatiles.

The residue was diluted with 7 mL of 2.0 N aqueous hydrogen chloride and then concentrated in vacuo to remove all volatiles to yield the title compound (0.43 g, 83%). ¹H-NMR (500 MHz, CD₃OD) δ: 8.88 (s, 1H), 8.70 (s, 1H), 3.96 (s, 2H). LC-MS: m/z (E/S) 173 (MH)⁺.

INTERMEDIATE 21

4-Methoxy-5-pyrimidinyl acetic acid (i-21)

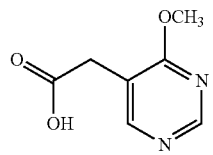 [SMILES: COc1ncncc1CC(=O)O]

Step A: Methyl(4-methoxy-5-pyrimidinyl)acetate

To a solution of 0.250 g (1.25 mmol) of ethyl(4-chloro-5-pyrimidinyl)acetate (see i-20, Step A) in 10 mL of absolute methanol was dissolved 0.060 g (2.50 mmol) of sodium metal. The resulting solution was heated under microwave conditions at 120° C. for 10 min. All volatiles were removed in vacuo and the residue was diluted with saturated sodium bicarbonate and extracted with dichloromethane (3×10 mL). The combined organic layers were washed with brine, dried over magnesium sulfate, filtered and evaporated to dryness in vacuo to afford the title compound as a clear gum (0.21 g, 93%). ¹H-NMR (500 MHz, CD₃OD) δ: 8.72 (s, 1H), 8.35 (s, 1H), 3.96 (s, 2H), 4.01 (s, 3H), 3.70 (s, 3H), 3.57 (s,2H). LC-MS: m/z (E/S) 183 (MH)⁺.

Step B: 4-Methoxy-5-pyrimidinyl acetic acid

To a stirred solution of 0.21 g (1.14 mmol) of methyl(4-methoxy-5-pyrimidinyl)acetate from Step A in 0.5 mL of water and 1.5 mL of ethanol was added 81 mg (1.9 mmol) of lithium hydroxide hydrate. The reaction mixture was stirred at ambient temperature for 2 h then concentrated in vacuo to remove all volatiles. The residue was diluted with 3 mL of 2.0 N aqueous hydrogen chloride and then concentrated in vacuo to remove all volatiles to yield the title compound as an off white solid (191 mg, 90%). ¹H-NMR (500 MHz, CD₃OD) δ: 8.72 (s, 1H), 8.35 (s, 1H), 4.01 (s, 3H), 3.57 (s,2H). LC-MS: m/z (E/S) 169 (MH)⁺.

INTERMEDIATE 22

5-Hydroxy-1,3-dimethyl-1H-pyrazol-4-yl)acetic acid (i-22)

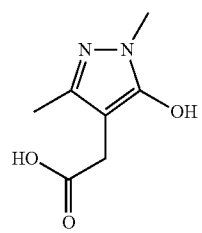

To a stirred solution of 2.0 g (10.0 mmol) of ethyl(5-hydroxy-1,3-dimethyl-1H-pyrazol-4-yl)acetate in 1.5 mL of water and 5 mL of ethanol was added 0.508 g (12.1 mmol) of lithium hydroxide hydrate. The reaction mixture was stirred at ambient temperature for 2 h then concentrated in vacuo to remove all volatiles. The residue was diluted with 7 mL of 2.0 N aqueous hydrogen chloride and then concentrated in vacuo to remove all volatiles to yield the title compound as an off white solid (1.7 g, 81%). ¹HNMR (500 MHz, CD₃OD) δ: 3.43 (s, 3H), 3.30 (s, 2H), 1.96 (s, 3H). LC-MS: m/z (E/S) 171 (MH)⁺.

INTERMEDIATE 23

2-(4-Methoxypyrimidin-5-yl)propanoic acid (i-23)

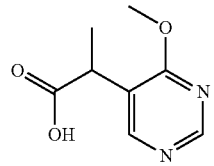

Step A: Ethyl 2-(4-chloropyrimidin-5-yl)propanoate

To a stirred, cooled (−78° C. solution of 5.8 g (29 mmol) of ethyl(4-chloro-5-pyrimidinyl)acetate (see Step A, i-20) in 75 mL of anhydrous THF under an atmosphere of nitrogen was added 15.2 mL (30.4 mmol) of a 2.0 M solution of lithium diisopropylamide in anhydrous THF. The resulting mixture was stirred for 15 min then 2.26 mL (36.1 mmol) of iodomethane was added over 5 min. The reaction mixture was stirred for 15 min, allowed to warm to −20° C. over 45 min, then warmed to 0° C. for 15 min. The reaction mixture was then quenched with a saturated ammonium chloride solution and extracted with 50 mL of dichloromethane. The organic layer was dried over magnesium sulfate, filtered, and evaporated in vacuo. The crude residue was purified by silica gel chromatography eluting with a 20% ethyl acetate in hexanes mixture afforded the title compound (1.9 g, 31%). ¹H-NMR (500 MHz, CD₃OD) δ: 8.88 (s 1H), 8.74 (s, 1H), 4.17 (m, 2H), 1.58 (d, J=7 Hz, 3H), 1.29 (t, J=7 Hz, 3H). LC-MS: m/z (E/S) 215 (MH)⁺.

Step B: Methyl 2-(4-methoxypyrimidin-5-yl)propanoate

To a solution of 0.250 g (1.17 mmol) of ethyl 2-(4-chloropyrimidin-5-yl)propanoate from step A in 5 mL of absolute methanol was dissolved 0.054 g (2.34 mmol) of sodium metal. The resulting solution was heated under microwave conditions at 120° C. for 10 min. All volatiles were removed in vacuo and the residue was diluted with saturated sodium bicarbonate and extracted with dichloromethane (3×10 mL). The combined organic layers were washed with brine, dried over magnesium sulfate, filtered and evaporated to dryness in vacuo to afford the title compound as a clear gum (0.21 g, 93%). ¹H-NMR (500 MHz, CD₃OD) δ: 8.65 (s 1H), 8.36 (s, 1H), 4.0 (s, 3H), 3.9 (q, J=7 Hz, 2H), 3.66 (s, 3H), 1.58 (d, J=7 Hz, 3H). LC-MS: m/z (E/S) 197 (MH)⁺.

Step C: 2-(4-Methoxypyrimidin-5-yl)propanoic acid

To a stirred solution of 0.21 g (1.06 mmol) of methyl 2-(4-methoxypyrimidin-5-yl)propanoate from Step B in 0.5 mL of water and 1.5 mL of ethanol was added 81 mg (1.9 mmol) of lithium hydroxide hydrate. The reaction mixture was stirred at ambient temperature for 2 h then concentrated in vacuo to remove all volatiles. The residue was diluted with 3 mL of 2.0 N aqueous hydrogen chloride and then concentrated in vacuo to remove all volatiles to yield the title compound as an off white solid (70 mg, 36%). $^1$H-NMR (500 MHz, CD$_3$OD) δ: 8.67 (s 1H), 8.4 (s, 1H), 4.07 (s, 3H), 3.9 (q, J=7 Hz, 2H), 1.58 (d, J=7 Hz, 3H). LC-MS: m/z (E/S) 183 (MH)$^+$.

INTERMEDIATE 24

2-Fluoro-2-pyridin-2-ylpropanoic acid (i-24)

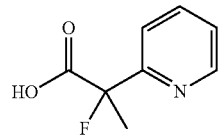

Step A: Methyl 2-fluoro-2-pyridin-2-ylpropanoate

To a stirred, cooled (−78° C.) solution of 5.00 mL (10.0 mmol) of a 2.0 M solution of lithium diisopropylamine in tetrahydrofuran under an atmosphere of nitrogen was added a solution of 1.5 g (9.1 mmol) of methyl 2-pyridin-2-yl-propanoate in 4.0 mL of anhydrous THF. The reaction mixture was allowed to stir for 10 min then warmed to 0° C. over 30 min. The mixture was then re-cooled to −78° C. and a solution of 3.70 g (11.8 mmol) of N-fluoro-N-(phenylsulfonyl)benzenesulfonamide in 4.0 mL THF was added. The resulting mixture was allowed to warm to ambient temperature and stir for 2 h. The reaction was quenched with 50 mL of a saturated ammonium chloride solution and then extracted with diethyl ether (3×50 mL). The combined organic layers were dried over magnesium sulfate, filtered and evaporated in vacuo. The crude residue was purified by silica gel chromatography eluting with a 0-40% ethyl acetate in hexanes gradient to afford the title compound as a dark oil (1.3 g, 78%). LC-MS: m/z (E/S) 184 (MH)$^+$.

Step B: 2-Fluoro-2-pyridin-2-ylpropanoic acid

To a solution of 0.89 g (4.9 mmol) of methyl 2-fluoro-2-pyridin-2-ylpropanoate from Step A in 2 mL of anhydrous THF was added 1.3 g (9.7 mmol) of potassium trimethylsilanolate. The mixture was allowed to stir for 3 h at ambient temperature then quenched with 1 mL of trifluoroacetic acid. The volatiles were evaporated in vacuo and the resulting residue was purified by reverse phase HPLC (YMC Pack Pro C18, 100×20 mm I.D. column, 0-60% 0.1% trifluoroacetic acid in acetonitrile/0.1% trifluoroacetic acid in water gradient) to afford the title compound as a light yellow oil (785 mg, 95%). LC-MS: m/z (E/S) 170 (MH)$^+$.

INTERMEDIATE 25

2-(2-Oxopyridin-1(2H)-yl)propanoic acid (i-25)

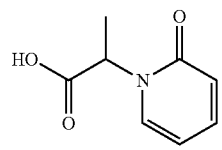

Step A: Tert-butyl 2-(2-oxopyridin-1(2H)-yl)propanoate

To a stirred solution 9.5 g (0.10 mol) of 2-hydroxypyridine in 250 mL of DMF was added 16.6 g (0.120 mol) of potassium carbonate followed by 25.0 g (0.120 mol) of 2-bromopropionic acid tert-butyl ester. The resulting mixture was stirred at ambient temperature for 7 h then diluted with 1 L of water. The aqueous phase was extracted with ethyl acetate (3×200 mL) and the combined organics were washed with water (2×100 mL), brine (100 mL), dried over magnesium sulfate, filtered and evaporated in vacuo. The crude residue was purified by silica gel chromatography eluting with 25% ethyl acetate in hexanes to afford the title compound as a clear gum 16 g (72%). LC-MS: m/z (ES) 224 (MH)$^+$ Step B: 2-(2-Oxopyridin-1(2H)-yl)propanoic acid To a stirred suspension of 16.6 g (74.4 mmol) of tert-butyl 2-(2-oxopyridin-1(2H)-yl)propanoate from step A in 10 mL of anhydrous 1,4-dioxane under an atmosphere of nitrogen was added 150 mL of a 4.0 M hydrogen chloride solution in 1,4-dioxane. The resulting solution was stirred overnight at ambient temperature then evaporated to dryness in vacuo to afford the title compound as a white solid (12.4 g, quantitative yield). LC-MS: m/z (ES) 168 (MH)$^+$

INTERMEDIATE 26

2-(2-Oxo-1,3-oxazolidin-3-yl)propanoic acid (i-26)

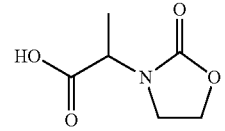

Step A: Benzyl(2-oxo-1,3-oxazolidin-3-yl)acetate

To a stirred solution of 1.0 g (6.9 mmol) of (2-oxo-1,3-oxazolidin-3-yl)acetic acid in 10 mL of anhydrous DMF was added 1.0 g (7.6 mmol) of potassium carbonate followed by 1.0 mL (8.3 mmol) of benzyl bromide. The reaction mixture was stirred for 3 h then quenched with water. The aqueous phase was extracted with ethyl acetate (3×25 mL) and the combined organics were washed with water (2×10 mL), brine (10 mL), dried over magnesium sulfate, filtered and evaporated in vacuo. The crude residue was purified by silica gel chromatography eluting with 50% ethyl acetate in hexanes to afford the title compound as a white solid 0.50 g (31%). LC-MS: m/z (ES) 236 (MH)$^+$.

Step B: Benzyl 2-(2-oxo-1,3-oxazolidin-3-yl)propanoate

To a stirred solution of 0.50 g (2.1 mmol) of benzyl(2-oxo-1,3-oxazolidin-3-yl)acetate from step A in 15 mL of anhydrous THF at −78° C. under an atmosphere of nitrogen was added 1.2 mL (2.4 mmol) of a 2.0 M solution of lithium diisopropylamide in anhydrous THF. The resulting yellow solution was stirred for 15 min at −78° C. and then 0.0360 g (2.55 mmol) of iodomethane was added. The resulting mixture was stirred for 2 h with gradual warming to ambient temperature then quenched with a saturated aqueous ammonium chloride solution. The aqueous phase was extracted with ethyl acetate (3×20 mL) and the combined organics were washed with brine, dried over magnesium sulfate, filtered and evaporated to dryness in vacuo. The crude residue was purified by silica gel chromatography eluting with 40% ethyl acetate in hexanes to afford the title compound as a clear gum 0.37 g (70%). LC-MS: m/z (ES) 250 (MH)+.

Step C: 2-(2-Oxo-1,3-oxazolidin-3-yl)propanoic acid

A 25 mL round bottom flask under an atmosphere of nitrogen was charged with 0.030 g (0.028 mmol) of 10 weight percent palladium on activated carbon and wet with 2 ml of ethanol. Next, a solution of 0.37 g (1.5 mmol) of benzyl 2-(2-oxo-1,3-oxazolidin-3-yl)propanoate from step B above in 10 mL of ethanol was added and the mixture placed under 1 atmosphere of hydrogen. The reaction was stirred for 3 h then filtered through a pad of Celite®. The pad was washed with 20 mL of ethanol and the filtrate was evaporated in vacuo to afford the title compound as a colorless solid (0.24 g, quantitative yield). $^1$H-NMR (500MHz, CD$_3$OD) δ: 4.60-4.30 (m, 3H), 3.80-3.60 (m, 2H), 1.45 (d, J=3.5, 3H). LC-MS: m/z (ES) 160 (MH)+.

INTERMEDIATE 27

2-(2H-1,2,3-Triazol-2-yl)propanoic acid (i-27)

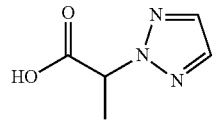

Intermediate 27 was prepared from 2H-1,2,3-triazol-2-ylacetic acid using a procedure analogous to that used to prepare Intermediate 26. LC-MS: m/z (ES) 142.2 (MH)+.

INTERMEDIATE 28

2-Bromo-5,6-dihydro-4H-cyclopenta[d][1,3]thiazole-4-carboxylic acid (i-28)

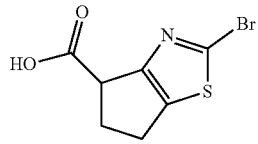 [SMILES: O=C(O)C1CCc2sc(Br)nc21]

Step A: Ethyl 2-bromo-5,6-dihydro-4H-cyclopenta[d][1,3]thiazole-4-carboxylate

To a solution of tert-butyl nitrite (4.2 ml, 35.3 mmol) and copper(II)bromide (6.3 g, 28 mmol) in acetonitrile (100 ml) was added portionwise ethyl 2-amino-5,6-dihydro-4H-cyclopenta[d][1,3]thiazole-4-carboxylate (5.0 g, 24 mmol), (see i-13, step A). Once the addition was complete the mixture stirred at room temperature for 3 h. The mixture was poured into 600 mL of a 2.0 N aqueous hydrogen chloride solution and extracted with ethyl acetate (3×200 ml). The combined organic layers were washed with 500 mL of a 1.0 N aqueous hydrogen chloride solution, water (250 ml), a sat. aq. sodium bicarbonate solution (200 ml) and brine (150 ml). The organic phase was then dried over magnesium sulfate, filtered and evaporated. The crude residue was purified by MPLC (Biotage Horizon: FLASH 40M) eluent: 100% Hexanes (100 ml), gradient rising from 100% Hexanes to 25% ethyl acetate in hexanes (750 ml), then 25% ethyl acetate in Hexanes (700 ml) to afford the title compound as a light orange oil (1.9 g, 29%). NMR (500 MHz CDCl$_3$) δ: 4.22 (q, J=7.1, 2H), 4.00 (m, 1H), 3.04-3.11 (m, 1H), 2.88-2.94 (m, 1H), 2.77 (q, J=7.3, 2H), 1.31 (t, J=7.1, 3H).

Step B: 2-Bromo-5,6-dihydro-4H-cyclopenta[d][1,3]thiazole-4-carboxylic acid

A solution of ethyl 2-bromo-5,6-dihydro-4H-cyclopenta[d][1,3]thiazole-4-carboxylate (4.92 g, 17.8 mmol) from step A was dissolved in 20 mL of methanol and added dropwise to a mixture of 4.25 mL (21.3 mmol) of a 5.0 N aqueous sodium hydroxide solution, 16 mL of water and 30 mL of methanol. After addition was complete the mixture was stirred for 2 h. The methanol was removed by evaporation and the pH of the remaining aqueous was adjusted to ~2.5 with con. HCl. The mixture was saturated with solid sodium chloride and extracted with ethyl acetate. The combined organic layers were washed with brine, dried over sodium sulfate and treated with activated charcoal overnight. The mixture was filtered and evaporated in vacuo. The residue was triturated with ethyl acetate and the solid filtered to afford the title compound (1.94 g). The mother liquor was evaporated and purified by MPLC using a gradient rising from 100% Hexanes to 100% ethyl acetate in Hexanes to afford an additional 0.82 g of the title compound as an off white solid (2.76 g in total, 62.0%). $^1$H NMR (500 MHz CDCl$_3$) δ: 4.04 (m, 1H), 3.02-3.08 (m, 1H), 2.88-2.94 (m, 1H), 2.78-2.83 (m, 2H).

INTERMEDIATE 29

2-Chloro-5,6-dihydro-4H-cyclopenta[d][1,3]thiazole-4-carboxylic acid (i-29)

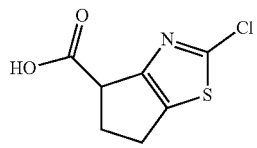 [SMILES: O=C(O)C1CCc2sc(Cl)nc21]

Intermediate 29 was prepared from tert-butyl nitrite, copper(II)chloride and ethyl 2-amino-5,6-dihydro-4H-cyclopenta[d][1,3]thiazole-4-carboxylate (see i-13, step A) using a procedure analogous to that used to prepare Intermediate 28.

INTERMEDIATE 30

2-Iodo-5,6-dihydro-4H-cyclopenta[d][1,3]thiazole-4-carboxylic acid (i-30)

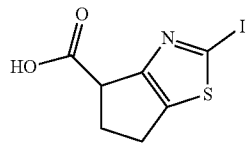 [SMILES: O=C(O)C1CCc2sc(I)nc21]

Intermediate 30 was prepared from tert-butyl nitrite, copper(II)iodide and ethyl 2-amino-5,6-dihydro-4H-cyclopenta[d][1,3]thiazole-4-carboxylate (see i-13, step A) using a procedure analogous to that used to prepare Intermediate 28.

INTERMEDIATE 31

2-Fluoro-5,6-dihydro-4H-cyclopenta[d][1,3]-thaizole-4-carboxylic acid (i-31)

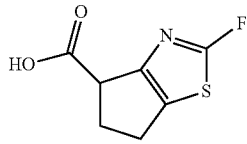 [SMILES: O=C(O)C1CCc2sc(F)nc21]

Step A: Ethyl 2-fluoro-5,6-dihydro-4H-cyclopenta[d]thiazole-4-carboxylate

Ethyl 2-amino-5,6-dihydro-4H-cyclopenta[d][1,3]thiazole-4-carboxylate (2.0 g, 9.4 mmol), (see i-13, step A) was dissolved in fluoroboric acid (5.17 g, 28.3 mmol) and the mixture cooled to the point just above it freezes (~5° C.). Nitrosonium tetrafluoroborate (1.1 g, 9.4 mmol) was added portionwise and mixture stirred at 0° C. for 20min. Diethyl ether (60 ml) added and mixture stirred at −50° C. for 30 min. Filtered and the solid washed with diethyl ether and air dried. The solid was taken up in toluene (70 ml) and warmed to 90° C. for 30 min. The mixture was cooled and evaporated, and the crude residue purified by MPLC (eluent: gradient rising from 100% Hexanes to 40% EtOAc in Hexanes) to give the title compound 390mg (19%) as a yellow oil. $^1$H NMR (500 MHz CDCl$_3$) δ; 4.22 (q, J=7.1, 2H), 3.93 (dd, J=7.0 and 5.0, 1H), 3.08 (m, 1H), 2.91 (m, 1H), 2.71 (m, 2H), 1.31 (t, J=7.1, 3H).

Step B: 2-Fluor-5,6-dihydro-4H-cyclopenta[d][1,3]-thaizole-4-carboxylic acid

To a solution of ethyl 2-fluoro-5,6-dihydro-4H-cyclopenta[d]thiazole-4-carboxylate (0.100 g, 0.456 mmol) from step A in a mixture of THF (1.5 ml) and methanol (0.5 ml) was added a solution of lithium hydroxide (0.558 ml of a 1M solution, 0.588 mmol) and the resulting mixture stirred at room temperature for 90 min. A 1.0 N aqueous HCl (0.558 ml, 0.558 mmol) was added and the mixture evaporated to dryness. The resulting crude product was used immediately without purification.

INTERMEDIATE 32

6,7-Dihydro-5H-pyrrolo[1,2-d]tetrazole-5-carboxylic acid (i-32)

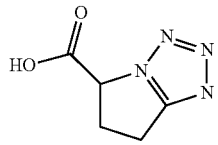

Step A: Methyl 5-methoxy-3,4-dihydro-2H-pyrrole-2-carboxylate

This intermediate was prepared according to the known experimental procedure found in: Wick, A., Bartlett, P. and Dolphin, D; *Helvetica Chimica*, 1971, 54, 1971.

Step B: Methyl 6,7-dihydro-5H-pyrrolo[1,2-d]tetrazole-5-carboxylate

To a solution of methyl 5-methoxy-3,4-dihydro-2H-pyrrole-2-carboxylate (900 mg, 6.04 mmol) from step A in 4 mL of acetic acid was added sodium azide (975 mg, 12.1 mmol) and the resulting suspension heat to 60° C. and stirred vigorously for 48 h. The solution was cooled to room temperature and diluted with 35 mL of ethyl ether. Solid potassium carbonate was added to the solution which was stirred at room temperature for 20 min. The solids were filtered off via fritted funnel, washed with cold ethyl ether and concentrated under vacuum. Solid precipitated during concentration and was filtered off after concentrating to one-fifth volume. The solids were washed once with cold ether (3 mL) and dried under high vacuum overnight to afford the title compound (308 mg, 31%). LC-MS: m/z (ES)=169 (MH)$^+$.

Step C: 6,7-Dihydro-5H-pyrrolo[1,2-d]tetrazole-5-carboxylic acid

To a solution of methyl 6,7-dihydro-5H-pyrrolo[1,2-d]tetrazole-5-carboxylate (300 mg, 1.78 mmol) from step B in THF/water/MeOH was added LiOH (214 mg, 8.92 mmol) and the resulting solution was heated via oil bath to 60° C. for 16 h. (Round bottom was equipped with a condenser.) The solution was cooled to room temperature and concentrated to remove organic solvents. The aqueous layer was then acidified to pH of ~5 using 2.0 N aqueous HCl. The mixture was concentrated to dryness under vacuum, azeotroping with toluene (2×20 mL) to make sure all water was removed. The material was used without further purification with lithium chloride as a by-product. LC-MS: m/z (ES)=155 (MH)$^+$.

INTERMEDIATE 33

3-Methyl-6,7-dihydro-5H-pyrrolo[2,1-c][1,2,4]triazole-7-carboxylic acid (i-33)

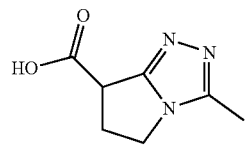

Step A: Ethyl 3-methyl-6,7-dihydro-5H-pyrrolo[2,1-c][1,2,4]-triazole-7-carboxylate This intermediate was prepared according to the known experimental procedure found in: Lawson, Edward C, e. al., *Tetrahedron Letters* 2000, 41, 4533.

Dissolved commercially available ethyl 2-oxopyrrolidine-3-carboxylate (2.50 g, 15.9 mmol) in 30 ml dichloromethane in 50 ml round bottom flask. To this solution was added trimethyloxonium tetrafluoroborate (2.59 g, 17.5 mmol) as a solid and rinsed in with 20 ml dichloromethane. The resulting mixture was stirred at room temperature for 2 h. Acetohydrazide (1.18 g, 15.9 mmol) was introduced as a solid to the mixture and the resulting solution was stirred at room temperature for 3 h. The solution was then concentrated under vacuum to remove all dichloromethane and the residue was then taken up in 100 ml n-butanol which was heated to reflux in an oil bath set at 120° C. overnight. The solution was cooled to room temperature and concentrated under vacuum. The residue was purified silica gel chromatography eluting with 10% dichloromethane: in methanol to afford the title compound (454 mg, 11%). $^1$H NMR (500 MHz DMSO-d6) δ; 4.16-4.06 (m, 1H), 4.00-3.88 (m, 1H), 2.85-2.78 (m, 1H), 2.29 (s, 3H), 1.55 (dt, J=6.7, 13.9 Hz, 2H), 1.32 (dt, J=6.7, 14.0 Hz, 2H), 0.88 (t, J=7.5 Hz, 3H). LC-MS: m/z (ES)=196 (MH)$^+$.

Step B: 3-Methyl-6,7-dihydro-5H-pyrrolo[2,1-c][1,2,4]triazole-7-carboxylic acid

To a solution of ethyl 3-methyl-6,7-dihydro-5H-pyrrolo[2,1-c][1,2,4]-triazole-7-carboxylate (400 mg, 2.05 mmol) from step A in THF/water/MeOH was added LiOH (250 mg, 10.3 mmol) and the resulting solution was heated to 60° C. for 16 h. The solution was cooled to room temperature and concentrated to remove organic solvents. The aqueous layer was then acidified to pH of ~5 using 2N HCl. The mixture was concentrated to dryness under vacuum, azeotroping with toluene (2×20 mL) to make sure all water was removed. The material was used without further purification with lithium chloride as a by-product. LC-MS: m/z (ES)=168 (MH)$^+$.

INTERMEDIATE 34

3-Methyl-6,7-dihydro-5H-pyrrolo[2,1-c][1,2,4]triazole-5-carboxylic acid (i-34)

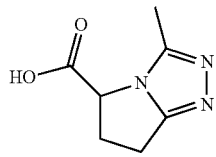

Intermediate 34 was prepared using procedures analogous to those for intermediate 33 replacing ethyl 2-oxopyrrolidine-3-carboxylate with methyl 5-oxopyrrolidine-2-carboxylate. LC-MS: m/z (ES)=168 (MH)$^+$.

INTERMEDIATE 35

2-(1H-Pyrazol-1-yl)butanoic acid (i-35)

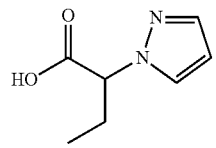

Intermediate 35 was prepared from commercially available 1H-pyrazol-1-ylacetic acid and ethyl iodide using a procedure analogous to that used to prepare i-26. LC/MS 155 (M+1)$^+$.

INTERMEDIATE 36

[6-Oxopyridazin-1(6H)-yl]acetic acid (i-30)

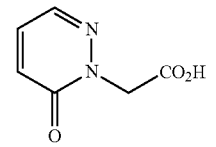 [SMILES: O=C(O)Cn1ncccc1=O]

To a solution of [3-chloro-6-oxopyridazin-1(6H)-yl]acetic acid (1.00 g, 5.30 mmol) in methanol (40 ml) was added 100 mg of 10% Pd/C. After the reaction mixture was stirred at ambient temperature under a hydrogen balloon for 1 h, the palladium was filtered off through Celite®. The filtrate was concentrated in vacuo and purified by reverse phase HPLC (TMC Pro-Pac C18; 0-40% 0.1% trifluoroacetic acid in acetonitrile/0.1% trifluoroacetic acid in water gradient). Removal of the volatiles in vacuo afforded the title compound as a white crystalline solid. $^1$H NMR (D$_2$O) δ: 8.06 (dd, J=3.9, 1.4 Hz, 1H), 7.56 (dd, J=9,4, 3.9 Hz, 1H), 7.12 (dd, J=9.4, 1.5 Hz, 1H), 4.95 (s, 2H). LC/MS 155.2 (M+1)$^+$.

INTERMEDIATE 37

[2-Oxopyrimidin-1(2H)-yl]acetic acid (i-37)

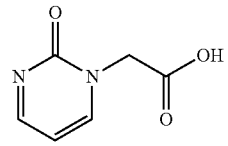 [SMILES: O=C(O)Cn1cccnc1=O]

To a mixture of 2-hydroxypyrimidine hydrochloride (1.00 g, 7.54 mmol) and chloroacetic acid (0.713 g, 7.54 mmol) was added 5 N sodium hydroxide solution (4.5 ml). The reaction mixture was heated at 105° C. for 2 h. After cooling to ambient temperature, the reaction was neutralized with 2 N hydrochloric acid (3.8 ml). The title compound was collected by crystallization and filtration as a pale yellow solid. $^1$H NMR (DMSO-d$_6$) δ: 13.2 (s, 1H), 8.59 (dd, J=3.9, 3.0 Hz, 1H), 8.16 (dd, J=6.4, 2.8 Hz, 1H), 6.46 (dd, J=6.4, 4.1 Hz, 1H), 4.58 (s, 2H). LC/MS 155.2 (M+1)$^+$.

INTERMEDIATE 38

2-[2-Oxopyrimidin-1(2H)-yl]propanoic acid (i-38)

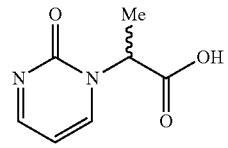

To 2-hydroxypyrimidine hydrochloride (1.27 g, 9.54 mmol) was added 5 N sodium hydroxide solution (5.7 ml) followed by (2S)-2-bromopropanoic acid (0.95 ml, 11 mmol). The reaction mixture was heated at 80° C. for 4 h. After cooling to ambient temperature, the reaction was neutralized with 2N hydrochloric acid (4.8 ml) and then directly purified by reverse phase HPLC (TMC Pro-Pac C18; 0-50% 0.1% trifluoroacetic acid in acetonitrile/0.1% trifluoroacetic acid in water gradient). Removal of the volatiles in vacuo afforded the title compound as a white solid. LC/MS 169.1 (M+1)$^+$.

INTERMEDIATE 39

[6-Oxopyrimidin-1(6H)-yl]acetic acid (i-39)

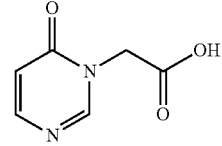 [SMILES: O=C(O)Cn1cnccc1=O]

To pyrimidin-4(3H)-one (0.608 g, 6.33 mmol) was added 5 N sodium hydroxide solution (2.5 ml) followed by chloroacetic acid (0.598 g, 6.33 mmol). The reaction mixture was heated at 105° C. for 2 h. After cooling to ambient temperature, the reaction was neutralized with 2 N hydrochloric acid (3.2 ml) and then directly purified by reverse phase HPLC (TMC Pro-Pac C18; 0-40% 0.1% trifluoroacetic acid in acetonitrile/0.1% trifluoroacetic acid in water gradient). Removal of the volatiles in vacuo afforded the title compound as a white solid. $^1$H NMR (DMSO-$d_6$): δ 13.2 (s, 1H), 8.43 (s, 1H), 7.94 (d, J 6.7 Hz, 1H), 6.43 (d, J=6.6 Hz, 1H), 4.63 (s, 2H). LC/MS 155.1 (M+1)$^+$.

INTERMEDIATE 40

2-[6-Oxopyrimidin-1(6H)-yl]propanoic acid (i-40)

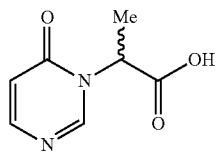 [SMILES: CC(C(=O)O)n1cnccc1=O]

To pyrimidin-4(3H)-one (0.908 g, 9.45 mmol) was added a 5 N sodium hydroxide solution (3.8 ml) followed by (2R)-2-bromopropanoic acid (0.95 ml, 11 mmol). The reaction mixture was heated at 85° C. for 1 h. After cooling to ambient temperature the reaction was neutralized with 2 N hydrochloric acid (5.2 ml) and then directly purified by reverse phase HPLC (TMC Pro-Pac C18; 0-40% 0.1% trifluoroacetic acid in acetonitrile/0.1% trifluoroacetic acid in water gradient). Removal of the volatiles in vacuo afforded the title compound as a white solid. $^1$H NMR (DMSO-$d_6$) δ: 8.48 (d, J=2.7 Hz, 1H), 7.88 (dd, J=7.8, 2.8 Hz, 1H), 6.12 (d, J=7.6 Hz, 1H), 5.04 (q, J=7.3 Hz, 1H), 1.64 (d, J=7.5 Hz, 3H). LC/MS 169.1 (M+1)$^+$.

INTERMEDIATE 41

2-[6-Oxopyridazin-1(6H)-yl]propanoic acid (i-41)

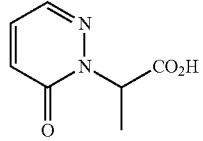

To 3(2H)-pyridazinone (1.19 g, 12.3 mmol) was added 5 N sodium hydroxide solution (4.9 ml) followed by (2S)-2-bromopropanoic acid (1.11 ml, 12.3 mmol). The reaction mixture was heated at 90° C. for 1 h. After cooled downed to ambient temperature, 2 N hydrochloric acid (6.2 ml) was added and the reaction mixture was directly purified by reverse phase HPLC (TMC Pro-Pac C18; 0-40% 0.1% trifluoroacetic acid in acetonitrile/0.1% trifluoroacetic acid in water gradient). The pure fractions were collected and the solvent was removed in vacuo to afford the title compound as pale yellow solid. 2-[6-Oxopyridazin-1(6H)-yl]propanoic acid: $^1$H NMR (D$_2$O): δ 8.07 (dd, J=4.1, 1.6 Hz, 1H), 7.53 (dd, 9.3, 3.9 Hz, 1H), 7.09 (dd, J=9.4, 1.6 Hz, 1H), 5.46 (m, 1H), 1.64 (d, J=7.3 Hz, 3H).

INTERMEDIATE 42

[2-oxopyrazin-1(2H)-yl]acetic acid (i-42)

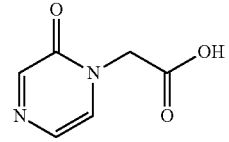 [SMILES: O=C(O)Cn1ccncc1=O]

To Pyrazin-2(1H)-one (0.333 g, 3.47 mmol) was added 5 N sodium hydroxide solution (2.1 ml) followed by chloroacetic acid (0.524 g, 5.54 mmol). The reaction mixture was heated at 100° C. for 2 h. After cooling to ambient temperature, 2 N hydrochloric acid (3.5 ml) was added and the reaction mixture was directly purified by reverse phase HPLC (TMC Pro-Pac C18; 0-40% 0.1% trifluoroacetic acid in acetonitrile/ 0.1% trifluoroacetic acid in water gradient). The pure fractions were lyophilized overnight to yield the title compound as a yellow solid. LC/MS 155.2 (M+1)$^+$.

INTERMEDIATE 43

[(6S)-4-Oxo-4,6,7,8-tetrahydropyrrolo[1,2-α]pyrimidine-6-carboxylic acid (i-43)

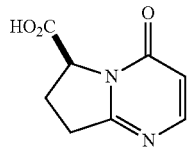 [SMILES: O=C(O)[C@@H]1CCc2nccc(=O)n21]

Step A: Methyl[6(S)-4-oxo-4,6,7,8-tetrahydropyrrolo[1,2-α]pyrimidine-6-carboxylate Methyl(2S)-5-methoxy-3,4-dihydro-2H-pyrrole-2-carboxylate (4.19 g, 26.6 mmol) and 3-azatricyclo[4.2.1.0.$^{2,5}$] non-7-en-4-one (2.4 g, 17.8 mmol) were heated at 110° C. overnight. Purification by silica gel chromatography eluting with a 0-100% ethyl acetate in hexanes gradient afforded the title compound methyl [6(S)-4-oxo-4,6,7,8-tetrahydropyrrolo[1,2-α]pyrimidine-6-carboxylate and the intermediate methyl(7S)-9-oxo-3,8-diazatetracyclo[9.2.1.0$^{2,10}$.0$^{4,8}$]tetradeca-3,12-diene-7-carboxylate. The intermediate was heated at 150° C. for 45 min to afford the title compound without further purification. LC/MS 195.2 (M+1)$^+$.

Step B: [(6S)-4-oxo-4,6,7,8-tetrahydropyrrolo[1,2-α]pyrimidine-6-carboxylic acid Methyl[6(S)-4-oxo-4,6,7,8-tetrahydropyrrolo[1,2-α]pyrimidine-6-carboxylate (9.95 g, 51.2 mmol) from step A in tetrahydrofuran (60 ml), methanol (40 ml) and a solution of lithium hydroxide (3.32 g, 77 mmol) in water (40 ml) was stirred at ambient temperature for 1 h. 2 N hydrochloric acid (38.5 ml) was added to neutralize the reaction mixture which was then directly purified by reverse phase HPLC (TMC Pro-Pac C18; 0-40% 0.1% trifluoroacetic acid in acetonitrile/ 0.1% trifluoroacetic acid in water gradient). The O-alkylation product was eluted fast. The pure fractions were collected and lyophilized overnight afforded the title compound as a pale yellow solid. $^1$H NMR (DMSO-$d_6$) δ: 7.89 (d, J=6.6 Hz, 1H), 6.24 (d, J=6.6 Hz, 1H), 4.92 (dd, J=10.0, 3.1 Hz, 1H), 3.12-2.99 (m, 2H), 2.52 (m, 1H), 2.11 (m, 1H). LC/MS 181.2 (M+1)$^+$.

INTERMEDIATE 44

Tert-butyl(2S,5R)-2-(4-amino-3-bromobenzyl)-5-[(R)-hydroxy(pyridin-3-yl)methyl]pyrrolidine-1-carboxylate (i-44)

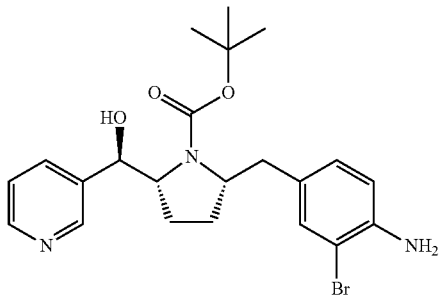 [SMILES: CC(C)(C)OC(=O)N1[C@H](Cc2ccc(N)c(Br)c2)CC[C@@H]1[C@H](O)c1cccnc1]

A solution of 0.089 g (0.501 mmol) of N-bromosuccinimide in 5 mL of anhydrous DMF was added in 15 portions over 2 min to a stirred solution of 0.192 g (0.501 mmol) of i-17 in 5 mL of anhydrous DMF under an atmosphere of nitrogen. The resulting slightly yellow reaction mixture was allowed to stir overnight at ambient temperature and then added to a mixture of water, ice and 1 mL of a 1.0 N aqueous sodium hydroxide solution. The aqueous phase was then extracted with dichloromethane (4×40 mL) and the combined organics were washed with brine, dried over sodium sulfate, filtered, and evaporated to dryness in vacuo. The crude residue was purified by silica gel chromatography eluting with a 0~100% EtOAc in hexanes gradient to afford the title compound as a white solid (0.197 g, 85.2%). $^1$H NMR (500 MHz, CDCl$_3$) δ: 8.53-8.54 (m, 2H), 7.73 (d, J=6.8 Hz, 1H), 7.25~7.29 (m, 2H), 6.93 (dd, J=1.9 & 8.0 Hz, 1H), 6.73 (d, J=8.0 Hz, 1H), 6.35 (br s, 1H), 4.44 (br s, 1H), 4.00~4.10 (m, 4H), 2.89~2.92 (m, 1H), 2.49 (dd, J=13.3 & 8.5 Hz, 1H), 1.67~1.75 (m, 1H), 1.59~1.67 (m, 1H), 1.51 (s, 9H), 1.37~1.57 (m, 2H). LC/MS: 462/464 (M+1)$^+$.

INTERMEDIATE 45

Tert-butyl(2R,5S)-2-[(R)-{[tert-butyl(dimethyl)silyl]oxy}(5-fluoropyridin-3-yl)methyl]-5-(4-nitrobenzyl)pyrrolidine-1-carboxylate (i-45)

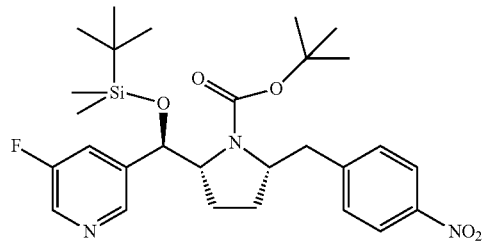

Intermediate 45 was prepared according to the procedures outlined for the synthesis of i-2 starting from (4S)-4-benzyl-3-hex-5-ynyl-1,3-oxazolidin-2-one (see i-1, Step A) and commercially available 5-fluoronicotinaldehyde.

Step A: (4S)-4-Benzyl-3-{(2R)-2-[(S)-(5-fluoropyridin-3-yl)(hydroxy)methyl]hex-5-ynoyl}-1,3-oxazolidin-2-one

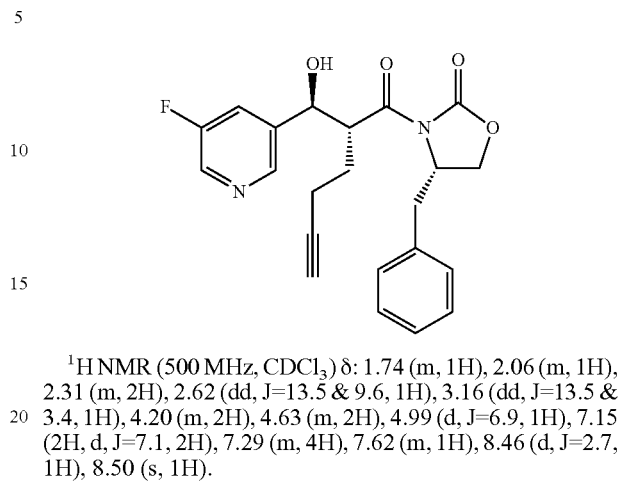

$^1$H NMR (500 MHz, CDCl$_3$) δ: 1.74 (m, 1H), 2.06 (m, 1H), 2.31 (m, 2H), 2.62 (dd, J=13.5 & 9.6, 1H), 3.16 (dd, J=13.5 & 3.4, 1H), 4.20 (m, 2H), 4.63 (m, 2H), 4.99 (d, J=6.9, 1H), 7.15 (2H, d, J=7.1, 2H), 7.29 (m, 4H), 7.62 (m, 1H), 8.46 (d, J=2.7, 1H), 8.50 (s, 1H).

Step B: (4S)-4-Benzyl-3-{(2R)-2-[(S)-{[tert-butyl(dimethyl)silyl]oxy}(5-fluoropyridin-3-yl)methyl]hex-5-ynoyl}-1,3-oxazolidin-2-one

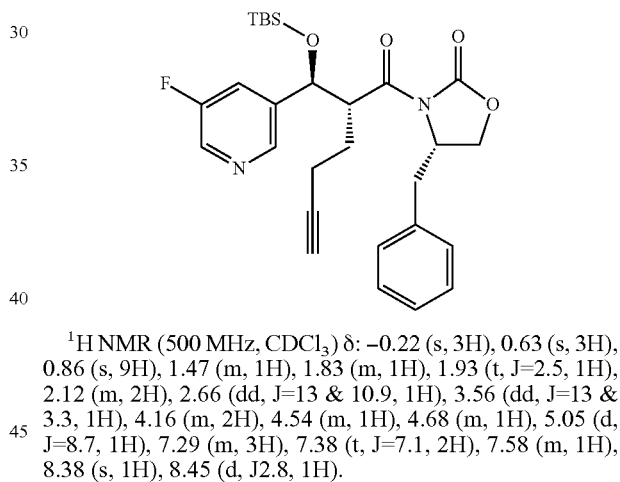

$^1$H NMR (500 MHz, CDCl$_3$) δ: −0.22 (s, 3H), 0.63 (s, 3H), 0.86 (s, 9H), 1.47 (m, 1H), 1.83 (m, 1H), 1.93 (t, J=2.5, 1H), 2.12 (m, 2H), 2.66 (dd, J=13 & 10.9, 1H), 3.56 (dd, J=13 & 3.3, 1H), 4.16 (m, 2H), 4.54 (m, 1H), 4.68 (m, 1H), 5.05 (d, J=8.7, 1H), 7.29 (m, 3H), 7.38 (t, J=7.1, 2H), 7.58 (m, 1H), 8.38 (s, 1H), 8.45 (d, J2.8, 1H).

Step C: (2R)-2-[(S)-{[Tert-butyl(dimethyl)silyl]oxy}(5-fluoropyridin-3-yl)methyl]hex-5-ynoic acid

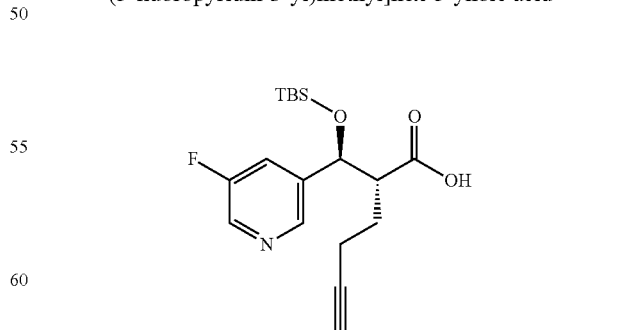

$^1$H NMR (500 MHz, CDCl$_3$) δ: −0.15 (s, 3H), 0.95 (s, 3H), 0.87 (s, 9H), 1.47 (m, 1H), 1.73 (m, 1H), 1.96 (d, J=2.5, 1H), 2.17 (m, 1H), 2.27 (m, 1H), 2.98 (m, 1H), 5.06 (d, J=7.8, 1H), 7.54 (dd, J=8.9 & 1.6, 1H), 8.39 (s, 1H), 8.45 (d, J=2.7, 1H), 11.50 (br s, 1H).

Step D: 4-Methoxybenzyl{(1R)-1-[(R)-{[tert-butyl(dimethyl)silyl]oxy}(5-fluoropyridin-3-yl)methyl]pent-4-yn-1-yl}carbamate

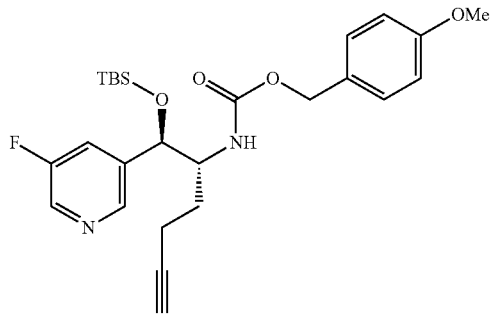

¹H NMR (500 MHz, CDCl₃) δ: −0.08 (s, 3H), 0.13 (s, 3H), 0.93 (s, 9H), 1.55 (m, 1H), 1.89 (m, 1H), 2.09 (s, 1H), 2.32 (m, 2H), 3.83 (s, 3H), 3.91 (m, 1H), 4.82-4.92 (m, 2H), 4.96 (d, J=5.1, 2H), 6.91 (d, J=8.4, 2H), 7.26 (d, J=8.4, 2H), 7.36 (m, 1H), 8.36 (s, 1H), 8.38 (d, J=2.3, 1H).

Step E: 4-Methoxybenzyl[(1R)-1-[(R)-{[tert-butyl(dimethyl)silyl]oxy}(5-fluoropyridin-3-yl)methyl]-5-(4-nitrophenyl)pent-4-yn-1-yl]carbamate

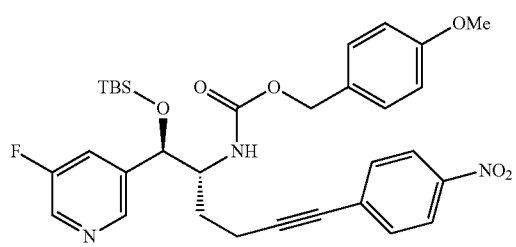

¹H NMR (500 MHz, CDCl₃) δ: −0.06 (s, 3H), 0.14 (s, 3H), 0.93 (s, 9H), 1.58 (m, 1H), 2.01 (m, 1H), 2.57 (m, 2H), 3.83 (s, 3H), 4.00 (m, 1H), 4.87-5.00 (m, 4H), 6.89 (d, J=8.6, 2H), 7.25 (d, J=8.6, 2H), 7.38 (d, J=9.1, 1H), 7.51 (d, J=8.5, 2H), 8.13 (d, J=8.5, 2H), 8.38 (m, 2H).

Step F: 4-Methoxybenzyl[(1R)-1-[(R)-{[tert-butyl(dimethyl)silyl]oxy}(5-fluoropyridin-3-yl)methyl]-5-(4-nitrophenyl)-4-oxopentyl]carbamate

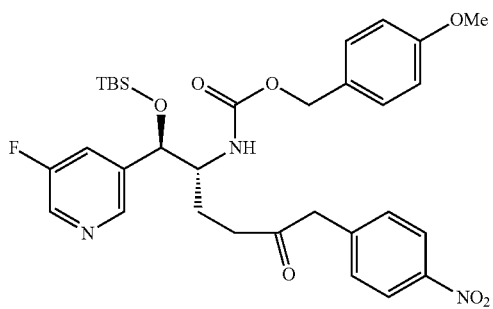

¹H NMR (500 MHz, CDCl₃) δ: −0.10 (s, 3H), 0.10 (s, 3H), 0.92 (s, 9H), 0.94 (m, 2H), 1.96 (m, 1H), 2.55 (m, 1H), 2.63 (m, 1H), 3.73 (m, 3H), 3.82 (s, 3H), 4.82 (s, 2H), 4.89 (d, J=11.9, 1H), 4.97 (d, J=11.9), 6.90 (d, J=8.5, 2H), 7.25 (d, J=8.5, 2H), 7.29 (m, 4H), 8.17 (d, J=8.7, 2H), 8.35 (s, 1H), 8.38 (s, 1H).

Step G: 3-{(R)-{[Tert-butyl(dimethyl)silyl]oxy}[(2R,5S)-5-(4-nitrobenzyl)pyrrolidin-2-yl]methyl}-5-fluoropyridine

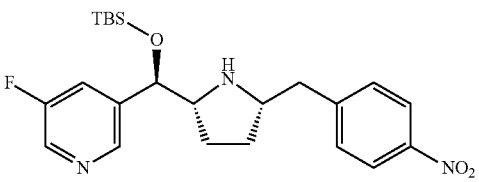

¹H NMR (500 MHz, CDCl₃) δ: −0.12 (s, 3H), 0.06 (s, 3H), 0.86 (s, 9H), 1.32 (m, 1H), 1.45 (m, 2H), 1.80 (m, 1H), 2.75 (dd, J=13.1 & 8.0, 1H), 2.86 (dd, J=13.1 & 5.0), 3.22 (q, J=7.6, 1H), 4.52 (d, J=6.6, 1H), 7.38 (m, 3H), 8.17 (d, J=8.7, 1H), 8.39 (m, 2H).

Step H: Tert-butyl(2R,5S)-2-[(R)-{[tert-butyl(dimethyl)silyl]oxy}(5-fluoropyridin-3-yl)methyl]-5-(4-nitrobenzyl)pyrrolidine-1-carboxylate

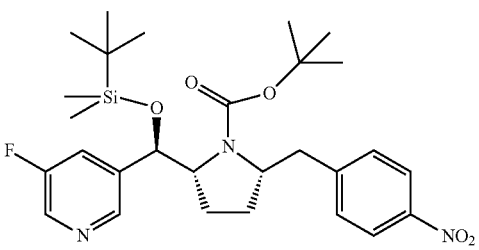

¹H NMR (500 MHz, CDCl₃) δ: 0.12 (s, 3H), 0.16 (s, 3H), 0.96 (s, 9H), 1.32 (br m, 1H), 1.59 (m, 11H), 1.80~2.05 (br m 2H), 2.69 & 3.09 (br m, 1H), 3.89 (br m, 2H), 5.38 & 5.62 (br m, 1H), 7.10 (br m, 2H), 7.48 (d, J=9.4, 1H), 8.09 (d, J=8.2, 2H), 8.41 (m, 2H).

INTERMEDIATE 46

Tert-butyl(2S,5R)-2-(4-aminobenzyl)-5-[(R)-(5-fluoropyridin-3-yl)(hydroxy)methyl]pyrrolidine-1-carboxylate (i-46)

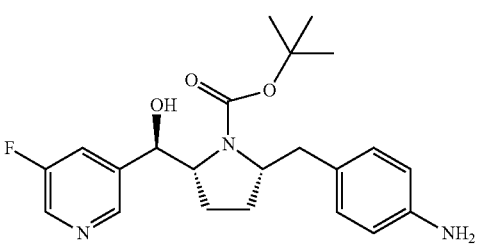 [SMILES: CC(C)(C)OC(=O)N1[C@H](Cc2ccc(N)cc2)CC[C@@H]1[C@H](O)c1cncc(F)c1]

To a solution of 5.54 g (10.2 mmol) of i-45 in a mixture of 100 mL of EtOH, 20 mL of water and 23 mL of acetic acid at 80° C. was added 3.97 g (71.1 mmol) of iron powder and the resulting mixture was stirred at 80° C. for 1.5 h. The reaction mixture was then cooled and filtered through Celite®. The filtrate was diluted with 150 mL of ethyl acetate and washed with water (200 ml), a saturated aqueous sodium bicarbonate solution and brine (50 ml), then dried over magnesium sulfate. The mixture was then filtered and evaporated to dryness. The residue was next dissolved in 100 mL of THF and 20 mL (20 mmol) of a 1.0 M solution of TBAF in tetrahydrofuran was added and the mixture heated at 50° C. for 2 h. The reaction mixture was cooled and diluted with 200 mL of ethyl acetate and washed with water (200 ml), brine (50 ml), then dried over magnesium sulfate. The mixture was then filtered and evaporated to dryness. The residue was purified by MPLC (Biotage Horizon: Flash 40+M) eluent: 100% Hexanes (200 ml), gradient rising from 100% Hexanes to 60% EtOAc in Hexanes (800 ml) then 60% EtOAc in Hexanes (700 ml) to affod the title compound as a clear foam (3.0 g, 74%). $^1$H NMR (500 MHz, CDCl$_3$) δ: 1.35-1.58 (m, 11H), 1.65-1.77 (m, 2H), 2.56 (dd, J=13.5 & 8.5, 1H), 2.90 (dd, J=13.5 & 4.0, 1H), 3.67 (br s, 2H), 4.03 (q, J=8.0, 1H), 4.11 (m, 1H), 4.45 (m, 1H), 6.58 (br s, 1H), 6.68 (d, J=8.3, 2H), 6.98 (d, J=8.3, 2H), 7.49 (d, J=8.7, 1H), 8.32 (s, 1H), 8.39 (d, J=2.7, 1H).

INTERMEDIATE 47

2-(1,3-Thiazol-4-yl)propanoic acid (i-47)

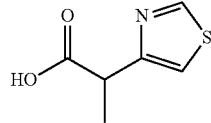

Step A: Ethyl 2-(1,3-thiazol-4-yl)propanoate

To a cooled (0° C.) solution of 43.3 g (300 mmol) of ethyl 2-methylacetoaceate in 270 mL of chloroform was added a solution of 15.5 mL (300 mmol) of bromine in 30 mL of chloroform dropwise over 30 min. After complete addition the mixture was allowed to warm to room temperature and stirred overnight. Air was bubbled through the reaction mixture for 70 min, then the solution was dried over sodium sulfate, filtered and evaporated to give 66.0 g (99.0%) of a pale orange oil. To a cooled (0° C.) mixture of 40.0 g (180 mmol) of this intermediate and 10.7 mL (269 mmol) of formamide in 400 mL of anhydrous 1,4-dioxane was added 15.0 g (67.2 mmol) of phosphorous pentasulfide. The mixture was warmed to room temperature and stirred for 1.5 h, then heated to 93° C. for 2.5 h. After cooling to ambient temperature overnight all volatiles were removed in vacuo and the residue was basified by the addition of a saturated aqueous sodium bicarbonate solution. The aqueous phase was extracted with dichloromethane (3×300 ml) and the combined organic layers were washed with a saturated aqueous sodium bicarbonate solution, water, brine and then dried over magnesium sulfate. The mixture was filtered, evaporated and the residue purified by MPLC (Biotage Horizon 2× FLASH 65i) eluent: 100% Hexanes (450 ml), then a gradient rising from 100% Hexanes to 25% EtOAc in Hexanes (2400 ml), then 25% EtOAc in Hexanes (1200 ml) to yield the title compound as an orange oil (20.0 g, 60.0%), $^1$H NMR (500 MHz, CDCl$_3$) δ: 1.24 (t, J=7.1, 3H), 1.58 (d, J=7.3, 3H), 4.05 (q, J=7.3, 1H), 4.17 (m, 2H), 7.18 (d, J=1.3, 1H), 8.76 (d, J=1.6, 1H).

Step B: 2-(1,3-Thiazol-4-yl)propanoic acid

A solution of 5.0 g (27 mmol) of ethyl 2-(1,3-thiazol-4-yl)proparioate from step A in 25 mL of methanol was added dropwise to a mixture of 6.6 mL (33 mmol) of a 5 N aq. NaOH solution, water (16ml) and methanol (30 ml). After addition was complete the mixture was stirred for 2 h. The methanol was removed by evaporation and the pH of the remaining aqueous was adjusted to ~2.5 with a concentrated hydrogen chloride solution. The mixture was saturated with solid sodium chloride and extracted with EtOAc (3×100 mL)). The combined organic layers were washed with brine, dried over sodium sulfate and treated with activated charcoal overnight. The mixture was filtered and evaporated to afford the title compound as an off-white solid 4.0 g (95%). $^1$H NMR (500 MHz, CDCl$_3$) δ: 1.63 (d, J=7.3, 3H), 4.11 (q, J=7.3), 7.25 (d, J=1.8, 1H), 8.88 (d, J=1.8, 1H), 10.25 (br s, 1H).

INTERMEDIATES 48 AND 49

(4S)-5,6-dihydro-4H-cyclopenta[d][1,3]thiazole-4-carboxylic acid (i-48) and (4R)-5,6-Dihydro-4H-cyclopenta[d][1,3]thiazole-4-carboxylic acid (i-49)

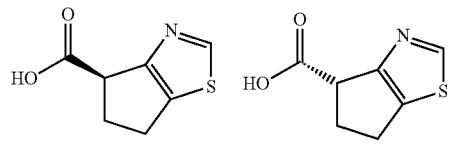

Intermediates 48 and 49 were prepared from ethyl 2-oxo-cyclopentane carboxylate using a procedure analogous to that used to prepare i-47. The two enantiomers were separated by SFC CO$_2$ S using an AD-H column 10©% MeOH/90% CO$_2$, 2.1 ml/min 100 bar 40° C. The first eluting enantiomer, (4S)-5,6-dihydro-4H-cyclopenta[d][1,3]thiazole-4-carboxylic acid, was designated as i-48 and the second eluting enantiomer, (4R)-5,6-Dihydro-4H-cyclopenta[d][1,3]thiazole-4-carboxylic acid, was designated as i-49. $^1$H NMR (500 MHz, CDCl$_3$) δ: 2.59-2.68 (m, 1H), 2.71-2.79 (m, 1H), 2.83-2.90 (m, 1H), 2.92-3.00 (m, 1H), 3.86 (m, 1H), 8.82 (s, 1H), 12.45 (s, 1H).

INTERMEDIATE 50

2-(1,3-Thiazol-4-yl)butanoic acid (i-50)

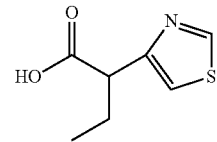

Intermediate 50 was prepared from commercially available 1,3-thiazol-4-ylacetic acid and ethyl iodide using a procedure analogous to that used to prepare i-26. $^1$H NMR (500 MHz, CDCl$_3$) δ: 0.95 (t, J=7.3, 3H), 1.25 (t, J=7.3, 3H), 1.95-2.05 (m, 1H), 2.08-2.17 (m, 1H), 3.88 (t, J=7.6, 1H), 4.15-4.23 (m, 2H), 7.22 (d, J=1.8, 1H), 8.77 (d, J=1.8, 1H).

INTERMEDIATE 51

4-Methyl-1H-1,2,3,-triazole-1-yl acetic acid (i-51)

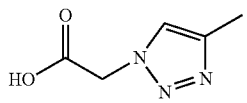

Step A: Ethyl[4-methyl-5-trimethylsilyl)-1H-1,2,3-triazole-1-yl]acetate

To a solution of 2.0 g (18 mmol) of 1-(trimethylsilyl)-1-proyne in toluene (20 mL) was added 2.3 g (18 mmol) of ethyl azido-acetate. The reaction mixture was heated at 120° C. overnight then cooled to ambient temperature. All volatiles were removed under reduced pressure and the residue was purified by column chromatography on silica gel eluting with a 5-25% acetone in hexanes gradient to yield the title compound as a colorless oil (0.77 g, 18%). $^1$HNMR (500 MHz, CDCl$_3$): δ 5.01 (s, 2H), 4.2 (m, 2H), 2.25 (s, 3H), 1.22 (m, 3H), 0.295 (s, 9H).

Step B: Ethyl[4-methyl-1H-1,2,3-triazole-1-yl]acetate

To a solution of 0.77 g (3.2 mmol) of ethyl[4-methyl-5-(trimethylsilyl)-1H-1,2,3-triazole-1-yl]acetate from step A in 2 mL of THF was added 1.3 mL (32 mmol) of a solution of 50% hydrofluoric acid in water. The resulting mixture was stirred at room temperature for 3 h and then evaporated to dryness in vacuo. Next, 5 mL of a 2.0 N ammonia in methanol solution was added and then the mixture was again evaporated to dryness in vacuo. The mixture was dissolved in dichloromethane, filtered and then evaporated in vacuo to afford the title compound as a clear gum (0.51 g. 93%). $^1$HNMR (500 MHz, CDCl$_3$) δ: 7.5 (s, 1H), 5.05 (s, 2H), 4.23 (m, 2H), 2.30 (s, 3H), 1.30 (m, 3H).

Step C: [4-Methyl-1H-1,2,3-triazole-1-yl]acetic acid

To a solution of 0.51 g (3.0 mmol) of ethyl[4-methyl-1H-1,2,3-triazole-1-yl]acetate_from step B in tetrahydrofuran (10 ml), methanol (6 ml) was added 6 mL (6 mmol) of an aqueous 1.0 M lithium hydroxide solution. The resulting mixture was stirred at ambient temperature for 1 h. The reaction mixture was neutralized with 8 mL of a 2 N hydrochloric acid solution which was then evaporated to remove all volatiles. The aqueous phase was extracted with ethyl acetate and the combined organics were washed with brine, dried over magnesium sulfate, filtered and evaporated to dryness to afford the title compound as a white solid (0.40 g, 95%). LC/MS 142 (M+1).

INTERMEDIATE 52: 2-[4-(Methoxycarbonyl)-1H-1,2,3-triazol-1-yl]propanoic acid (i-52) and INTERMEDIATE 53: 2-[5-(methoxycarbonyl)-1H-1,2,3-triazol-1-yl]propanoic acid (i-53)

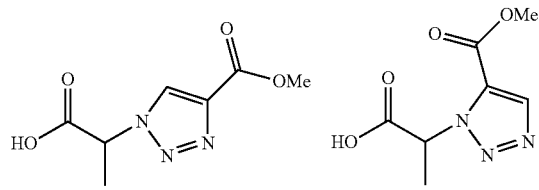

Step A: Methyl 1-(2-tert-butoxy-1-methyl-2-oxoethyl)-1H-1,2,3-triazole-4-carboxylate and methyl 1-(2-tert-butoxy-1-methyl-2-oxoethyl)-1H-1,2,3-triazole-5-carboxylate To a solution of 1.87 g (22.3 mmol) of methyl prop-2-ynoate in 40 mL of toluene was added 1.9 g (11 mmol) of tert-butyl 2-azidopropanate. The reaction mixture was heated at 100° C. for 3 h then cooled to ambient temperature. All volatiles were removed under reduced pressure and the crude residue purified by column chromatography on silica gel eluting with a 5 to 25% acetone in hexanes gradient to afford the title compounds.

Methyl 1-(2-tert-butoxy-1-methyl-2-oxoethyl)-1H-1,2,3-triazole-4-carboxylate (lower Rf) (1.4 g, 50%). $^1$HNMR (500 MHz, CDCl$_3$) δ: 8.30 (s, 1H), 5.46-5.41 (m, 1H), 4.11 (s, 3H), 1.83 (d, 3H), 1.47 (s, 9H). LC-MS: m/z (ES) 256 (MH)$^+$.

Methyl 1-(2-tert-butoxy-1-methyl-2-oxoethyl)-1H-1,2,3-triazole-5-carboxylate (higher Rf) (0.45 g, 16%). $^1$HNMR (500 MHz, CDCl$_3$) δ: 8.15 (s, 1H), 5.77-5.72 (m, 1H), 3.90 (s, 3H), 1.95 (d, J=7.3 Hz, 3H), 1.41 (s, 9H). LC-MS: m/z (ES) 256 (MH)$^+$.

Step B (i-52): 2-[4-(Methoxycarbonyl)-1H-1,2,3-triazol-1-yl]propanoic acid (i-52)

To a stirred solution of 0.55 g (2.2 mmol) of methyl 1-(2-tert-butoxy-1-methyl-2-oxoethyl)-1H-1,2,3-triazole-4-carboxylate from step A in 3 mL of anhydrous 1,4-dioxane was added 2.7 mL (11 mmol) of a 4.0 M hydrogen chloride solution in 1,4-dioxane. The resulting mixture was stirred for 1 h and then evaporated to dryness to afford the title compound as an off-white solid (0.40 g, 93%). $^1$HNMR (500 MHz, CD$_3$OD) δ: 8.67 (s, 1H), 5.60 (q, J=7.3 Hz, 1H), 3.90 (s, 3H), 1.88 (d, J=7.3 Hz, 3H). LC-MS: m/z (ES) 200 (MH)$^+$.

Step B (i-53) 2-[5-(Methoxycarbonyl)-1H-1,2,3-triazol-1-yl]propanoic acid (i-53)

To a stirred solution of 0.40 g (1.6 mmol) of methyl 1-(2-test-butoxy-1-methyl-2-oxoethyl)-1H-1,2,3-triazole-5-carboxylate from step A in 3 mL of anhydrous 1,4-dioxane was added 2.7 mL (11 mmol) of a 4.0 M hydrogen chloride solution in 1,4-dioxane. The resulting mixture was stirred for 1 h and then evaporated to dryness to afford the title compound as an off-white solid (0.27 g, 87%). LC-MS: m/z (ES) 200 (MH)$^+$.

INTERMEDIATE 54

2-[4-(Aminocarbonyl)-1H-1,2,3-triazol-1-yl]propanoic acid (i-54)

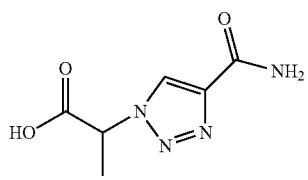

Intermediate 54 was prepared from commercially available propiolamide and tert-butyl 2-azidopropanate using a procedure analogous to that used to prepare i-52. $^1$HNMR (500

MHz, CD₃OD) δ: 8.48 (s, 1H), 5.50 (q, J=7.3 Hz, 1H), 1.85 (d, J=7.3 Hz, 3H). LC-MS: m/z (ES) 185 (MH)⁺.

INTERMEDIATES 55 AND 56

2-(4-Methyl-1H-1,2,3-triazol-1-yl)propanoic acid (i-55) and 2-(5-methyl-1H-1,2,3-triazol-1-yl)propanoic acid (i-56)

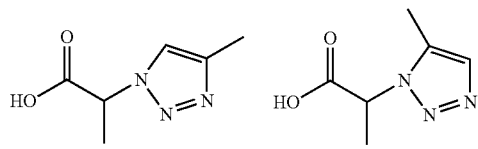

Step A: Methyl 2-[4-methyl-5-(trimethylsilyl)-1H-1,2,3-triazol-1-yl]propanoate and methyl 2-[5-methyl-4-(trimethylsilyl)-1H-1,2,3-triazol-1-yl]propanoate To a solution of 1.9 g (17 mmol) of trimethyl(prop-1-yn-1-yl)silane in 20 mL of toluene was added 2.3 g (18 mmol) of methyl 2-azidopropanoate. The reaction mixture was heated at 120° C. for 3 h. The mixture was cooled and the solvent was evaporated under reduced pressure. The residue was purified by column chromatography on silica gel eluting with a 5-25% acetone in hexanes gradient to yield the title compounds as ~6:1 mixture of methyl 2-[4-methyl-5-(trimethylsilyl)-1H-1,2,3-triazol-1-yl]propanoate to methyl 2-[5-methyl-4-(trimethylsilyl)-1H-1,2,3-triazol-1-yl]propanoate and is a colorless oil (3.0 g, 80%). LC-MS: m/z (ES) 242 (MH)⁺.

Step B: Methyl 2-(4-methyl-1H-1,2,3-triazol-1-yl)propanoate and methyl 2-(5-methyl-1H-1,2,3-triazol-1-yl)propanoate To a solution of 1.3 g (5.4 mmol) of methyl 2-[4-methyl-5-(trimethylsilyl)-1H-1,2,3-triazol-1-yl]propanoate and methyl 2-[5-methyl-4-(trimethylsilyl)-1H-1,2,3-triazol-1-yl]propanoate from step A in 2 mL of THF was added 2.2 mL (54 mmol) of a solution of 50% hydrofluoric acid in water. The resulting mixture was stirred at room temperature for 15 min and then evaporated to dryness in vacuo. Next, 8 mL of a 2.0 N ammonia in methanol solution was added and then the mixture was again evaporated to dryness in vacuo. The mixture was dissolved in dichloromethane, filtered and then evaporated in vacuo to afford the title compounds as a ~8:1 mixture of methyl 2-(4-methyl-1H-1,2,3-triazol-1-yl)propanoate to methyl 2-(5-methyl-1H-1,2,3-triazol-1-yl)propanoate. The mixture is a clear gum (0.67 g, 73%). LC-MS: m/z (ES) 170 (MH)⁺.

Step C: 2-(4-Methyl-1H-1,2,3-triazol-1-yl)propanoic acid and 2-(5-methyl-1H-1,2,3-triazol-1-yl)propanoic acid To a solution of 0.76 g (4.5 mmol) of methyl 2-(4-methyl-1H-1,2,3-triazol-1-yl)propanoate and methyl 2-(5-methyl-1H-1,2,3-triazol-1-yl)propanoate from step B above in 12 mL of ethanol was added 13.5 mL (13.5 mmol) of an aqueous 1.0 M lithium hydroxide solution. The resulting mixture was stirred at ambient temperature for 1 h. The reaction mixture was acidified with a 2 N hydrochloric acid solution until a pH of 4 was achieved and then evaporated to remove all volatiles. The aqueous phase was extracted with ethyl acetate and the combined organics were washed with brine, dried over magnesium sulfate, filtered and evaporated to dryness to afford the title compounds as an ~8:1 mixture of 2-(4-methyl-1H-1,2,3-triazol-1-yl)propanoic acid and 2-(5-methyl-1H-1,2,3-triazol-1-yl)propanoic acid. The mixture is an off-white solid (0.50 g, 58%). LC-MS: m/z (ES) 156 (MH)⁺.

INTERMEDIATE 57

2-(1-Methyl-1H-pyrazol-3-yl)propanoic acid (i-57)

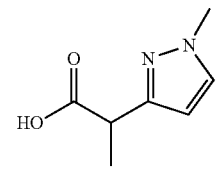

Step A: Benzyl propiolate

To a solution of 17.0 g (233 mmol) of propiolic acid in 600 mL of anhydrous DMF was added 39.9 g (233 mmol) of benzyl bromide followed by portionwise addition of 76.0 g (233 mmol) of Cs₂CO₃. After stirring at room temperature for 24 h, the reaction was quenched with a saturated aqueous ammonium chloride solution and extracted with EtOAc (3×200 mL). The combined extracts were washed with water then brine and dried over anhydrous sodium sulfate. The mixture was then filtered through a silica gel pad washing with hexanes, and the filtrate was evaporated under reduced pressure to afford a crude oil. The crude product was purified by silica gel chromatography eluting with a 0-20% ethyl acetate in hexane gradient to afford the title compound as a colorless oil (13.8 g, 35%). ¹H NMR (CDCl₃, 500 MHz) δ 7.41 (m, 5H), 5.25 (s, 2H), 2.92 (s, 1H).

Step B: Benzyl 2-(tributylstannyl)acrylate

To a solution of 6.42 g (40.1 mmol) of benzyl propiolate from step A in 25 ml of anhydrous TI-IF was added 0.93 g (0.80 mmol) of tetrakis(triphenylphosphine)palladium(0) followed by a solution of 12.6 g (42.1 mmol) of tributyltin hydride in 25 mL of anhydrous THF over 15 min. After stirring at room temperature overnight the solvent was removed under reduced pressure. The residue was filtered through a pad of Celite® which was then washed with hexanes. The filtrate was concentrated in vacuo and the crude product was purified by silica gel chromatography eluting with a 0-15% ethyl acetate in hexane gradient to afford the title compound as a colorless oil (13 g, 73%). ¹H NMR (CDCl₃, 500 MHz) δ 7.39 (m, 5H), 6.99 (d, J=2.7 Hz, 1H), 5.98 (d, J=2.7 Hz, 1H), 5.20 (s, 2H), 1.47 (m, 6H), 1.30 (m, 6H), 0.96 (m, 6H), 0.89 (t, J=7.4 Hz, 9H).

Step C: Benzyl 2-(1-methyl-1H-pyrazol-3-yl)acrylate

To a solution of 0.30 g (1.4 mmol) of 3-iodo-1-methyl-1H-pyrazole in 3 mL of anhydrous THF was added a solution of 0.82 g (1.8 mmol) of benzyl 2-(tributylstannyl)acrylate from step B above in 1 mL of anhydrous THF, 0.18 g (0.15 mmol) of tetrakis(triphenylphosphine)palladium(0) and 0.14 g (1.4 mmol) of copper(I)chloride. The reaction mixture was heated to 55° C. for 12 h, cooled and evaporated to dryness under reduced pressure. The residue was dissolved in 10 mL of a 1:1 mixture of hexane and EtOAc then filtered through a pad of Celite®. The pad was washed with 15 mL of a 1:1 mixture of hexane and EtOAc and the combined filtrates were evaporated to dryness. The crude residue was purified by silica gel chromatography eluting with a 0-80% EtOAc in hexanes gradient to afford the title compound as a colorless oil (0.23 g, 66%). LC-MS: m/z (ES) 265 (M+Na)⁺.

Step D: 2-(1-Methyl-1H-pyrazol-3-yl)propanoic acid

To 0.10 mg (0.093 mmol) of 10% palladium on carbon was added a solution of (0.23 g, 0.93 mmol) of benzyl 2-(1-methyl-1H-pyrazol-3-yl)acrylate prepared in step C above in 6 mL of methanol. The resulting suspension was stirred under an atmosphere of hydrogen (1 atmosphere) overnight. The residue was filtered through a pad of Celite® and the pad was washed cold methanol. The combined filtrates were evaporated under reduced pressure to give yield the title compound as an off-white gum (0.11 g, 76%). LC-MS: m/z (ES) 155 (MH)⁺.

INTERMEDIATE 58

2-(1,3-Thiazol-2-yl)propanoic acid (i-58)

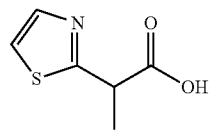

Step A: Ethyl 2-(1,3-thiazol-2-yl)propanoate

Prepared according to the procedures outlined in: Dondoni, A.; Dall'Occo, T.; Giancarlo, F.; Fogagnolo, M.; Medici, A. *Tetrahedron Letters*, 1984, 25, 3633-3636.

Step B: 2-(1,3-Thiazol-2-yl)propanoic acid

To a solution of 0.26 g (1.5 mmol) of ethyl 2-(1,3-thiazol-2-yl)propanoate from step A in 15 mL of methanol was added 3.0 mL (15 mmol) of an aqueous 5.0 M sodium hydroxide solution. The resulting mixture was stirred at ambient temperature overnight. The reaction mixture evaporated in vacuo to remove the methanol and the aqueous phase was acidified with a 2 N hydrochloric acid solution until a pH of 4 was achieved. The aqueous solution was purified by reverse phase HPLC (TMC Pro-Pac C18; 0-25% 0.1% trifluoroacetic acid in acetonitrile/0.1% trifluoroacetic acid in water gradient). The pure fractions were lyophilized overnight to afford the title compound as a white solid (0.17 g, 71%). LC-MS: m/z (ES) 158 (MH)⁺.

INTERMEDIATE 59

2-(3-Methyl-1H-pyrazol-5-yl)propanoic acid (i-59)

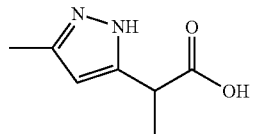

Step A: Ethyl 2-methyl-3,5-dioxohexanoate

Prepared according to the procedure outlined in: Solladie, G.; Gehrold, N.; Maignan, J. *Eur. J. Org. Chem.*, 1999, 2309-2314.

Step B: Ethyl 2-(3-methyl-1H-pyrazol-5-yl)propanoate

To a solution of 18.6 g (100. mmol) of ethyl 2-methyl-3,5-dioxohexanoate from step A in 200 mL of THF and 50 mL of water was added 3.45 mL (110 mmol) of anhydrous hydrazine. The biphasic reaction mixture was stirred at ambient temperature overnight then evaporated to dryness in vacuo. The crude yellow residue was dissolved in an ethyl acetate and water mixture and flushed through a 50 g silica gel plug. The filtrate was then evaporated to dryness in vacuo and the residue purified by silica gel chromatography eluting with a 0-100% ethyl acetate in hexanes gradient to afford the title compound as a yellow oil (1.89 g, 10%). ¹H NMR (CDCl₃, 500 MHz) δ 7.26 (s, 1H), 5.98 (s, 1H), 4.20-4.12 (m, 2H), 3.81 (q, J=7.3 Hz, 1H), 2.28 (s, 3H), 1.51 (d, J=7.3 Hz, 3H), 1.25 (t, J=7.1 Hz, 3H). LC-MS: m/z (ES) 183 (MH)⁺.

Step C: 2-(3-Methyl-1H-pyrazol-5-yl)propanoic acid

To a solution of 1.24 g (6.8 mmol) of ethyl 2-(3-methyl-1H-pyrazol-5-yl)propanoate from step B in 20 mL of methanol and 5 mL of water was added 1.5 mL (7.5 mmol) of an aq. 5.0 M sodium hydroxide solution. The resulting mixture was stirred at ambient temperature for 2.5 h and then evaporated in vacuo to remove the methanol. The aqueous phase was extracted with ethyl acetate (2×75 mL) then acidified with a 2 N hydrochloric acid solution until a pH of 4 was achieved. The aqueous solution was extracted with ethyl acetate (5×50 mL) and the combined organic layers were dried over anhydrous sodium sulfate, filtered and evaporated to yield the title compound as a yellow gum (0.80 g, 76%). ¹H NMR (CDCl₃, 500 MHz) δ 10.23 (br s, 1H), 7.26 (s, 1H), 5.97 (s, 1H), 3.87 (q, J=7.3 Hz, 1H), 2.26 (s, 3H), 1.59 (d, J=7.3 Hz, 3H). LC-MS: m/z (ES) 155 (MH)⁺.

INTERMEDIATE 60

2-(1H-Pyrazol-5-yl)propanoic acid (i-60)

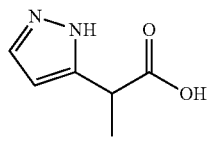

Intermediate 60 was prepared from commercially available ethyl formate and ethyl 2-methyl-3-oxobutanoate using a procedure analogous to that used to prepare i-59. ¹H NMR (CDCl₃, 500 MHz) δ 7.50 (s, 1H), 7.13 (br s, 1H), 6.22 (s, 1H), 3.95 (q, J=7.3 Hz, 1H), 1.63 (d, J=7.3 Hz, 3H). LC-MS: m/z (ES) 141 (MH)⁺.

INTERMEDIATE 61

(2-Oxo-1,3-oxazinan-3-yl)acetic acid (i-61)

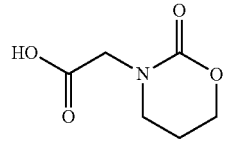

Step A: 1,3-Oxazinan-2-one

To a solution of 4.75 g (29.3 mmol) of 1,1'-carbonyldiimidazole in 260 mL of anhydrous dichloromethane was added 4.6 mL (27 mmol) of DIEA followed by 2.00 g (27 mmol) of 3-aminopropan-1-ol. The resulting mixture was stirred at ambient temperature overnight and then quenched with a saturated aqueous ammonium chloride solution. The layers were separated and the organic phase extracted with dichloromethane (2×30 mL). The combined organic layers were washed with brine, dried over anhydrous sodium sulfate, filtered and evaporated in vacuo. The crude residue was purified by silica gel chromatography eluting with a 5-15% methanol in ethyl acetate gradient to afford the title compound as a clear gum (0.20 g, 7.6%). $^1$HNMR (500 MHz, CDCl$_3$) δ: 6.12 (br s, 1H), 4.29 (t, J=5.4 Hz, 2H), 3.36 (td, J=6.2, 2.3 Hz, 2H), 2.00-1.95 (m, 2H).

Step B: Methyl(2-oxo-1,3-oxazinan-3-yl)acetate

A solution of 0.20 g (2.0 mmol) of 1,3-oxazinan-2-one from step A in 2 mL of anhydrous DMF was added to a 10 mL round bottom flask containing 0.13 g (3.2 mmol) of a 60% sodium hydride suspension in mineral oil under an atmosphere of nitrogen. After stirring for 10 min 0.37 g (2.4 mmol) of methyl bromoacetate was added in one portion and the reaction mixture was allowed to stir overnight. The reaction mixture was then quenched with 5 mL of a saturated aqueous ammonium chloride solution and then diluted with 20 mL of water. The resulting suspension was extracted with ethyl acetate (3×10 mL) and the combined organics were washed with water (2×3 mL), brine (1×3 mL) and dried over magnesium sulfate. The mixture was filtered, evaporated and purified by silica gel chromatography eluting with a 5% methanol in ethyl acetate mixture to afford the title compound as a clear oil (0.068 g, 20%). $^1$HNMR (500 MHz, CDCl$_3$) δ: 4.28 (t, J=5.4 Hz, 2H), 4.03 (s, 2H), 3.70 (s, 3H), 3.36 (t, J=6.2 Hz, 2H), 2.08-2.04 (m, 2H). LC-MS: m/z (ES) 174 (MH)$^+$.

Step C: (2-Oxo-1,3-oxazinan-3-yl)acetic acid

To a solution of 0.068 g (0.39 mmol) of methyl(2-oxo-1,3-oxazinan-3-yl)acetate from step B in 6 mL of THF and 2 mL of water and 2 mL of methanol was added 0.60 mL (1.2 mmol) of an aqueous 2.0 M sodium hydroxide solution. The resulting mixture was stirred at ambient temperature for 3 h and then evaporated in vacuo to remove the methanol and THF. The aqueous phase was acidified with a 2 N hydrochloric acid solution until a pH of 2 was achieved and then extracted with a 30% isopropyl alcohol in chloroform mixture (3×10 mL). The combined organic layers were dried over anhydrous sodium sulfate, filtered and evaporated to yield the title compound as an off-white solid (0.06 g, 99%). $^1$H NMR (CD$_3$OD, 500 MHz) δ: 4.32 (t, J=5.4 Hz, 2H), 4.03 (s, 2H), 3.41 (t, J=6.2 Hz, 2H), 2.10-2.05 (m, 2H). LC-MS: m/z (ES) 160 (MH)$^+$.

INTERMEDIATE 62

(3-Methyl-2-oxotetrahydropyrimidin-1(2H)-yl)acetic acid (i-62)

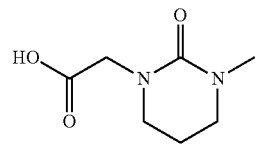

Step A: 1-Methyltetrahydropyrimidin-2(1H)-one

To a solution of 10.1 g (62.4 mmol) of 1,1'-carbonyldiimidazole in 113 mL of anhydrous dichloromethane was added 10.0 mL (56.7 mmol) of DIEA followed by 5.00 g (56.7 mmol) of N-methylpropane-1,3-diamine. The resulting mixture was stirred at ambient temperature overnight and then quenched with a saturated aqueous ammonium chloride solution. The layers were separated and the organic phase extracted with dichloromethane (2×50 mL). The combined organic layers were washed with brine, dried over anhydrous sodium sulfate, filtered and evaporated in vacuo. The crude residue was purified by silica gel chromatography eluting with a 5-15% methanol in ethyl acetate gradient to afford the title compound as a clear gum (0.700 g, 10.0%). $^1$HNMR (500 MHz, CDCl$_3$) δ: 4.69 (br s, 1H), 3.30-3.27 (m, 2H), 3.24 (t, J=6.0 Hz, 2H), 2.92 (s, 3H), 1.96-1.92 (m, 2H).

Step B: Tert-butyl(3-methyl-2-oxotetrahydropyrimidin-1(2H)-yl)acetate

A solution of 0.30 g (2.6 mmol) of 1-methyltetrahydropyrimidin-2(1H)-one from step A in 5 mL of anhydrous DMF was added to a 10 mL round bottom flask containing 0.16 g (4.2 mmol) of a 60% sodium hydride suspension in mineral oil under an atmosphere of nitrogen. After stirring for 10 min 0.62 g (3.2 mmol) of tert-butyl bromoacetate was added in one portion and the reaction mixture was allowed to stir overnight. The reaction mixture was then quenched with 5 mL of a saturated aqueous ammonium chloride solution and then diluted with 20 mL of water. The resulting suspension was extracted with ethyl acetate (3×10 mL) and the combined organics were washed with water (2×3 mL), brine (1×3 mL) and dried over magnesium sulfate. The mixture was filtered, evaporated and purified by silica gel chromatography eluting with a 0-5% methanol in ethyl acetate gradient to afford the title compound as a clear oil (0.090 g, 15%). $^1$HNMR (500 MHz, CDCl$_3$) δ: 3.88 (s, 2H), 3.23 (t, J=6 Hz, 2H), 3.20 (t, J=6 Hz, 2H), 2.84 (s, 3H), 1.94-1.89 (m, 2H), 1.37 (s, 9H). LC-MS: m/z (ES) 229 (MH)$^+$.

Step C: (3-Methyl-2-oxotetrahydropyrimidin-1(2H)-yl)acetic acid

To a solution of 0.090 g (0.39 mmol) of tert-butyl(3-methyl-2-oxotetrahydropyrimidin-1(2H)-yl)acetate from step B in 4 mL of anhydrous dichloromethane was added 1 mL of

INTERMEDIATE 63

(3-Methyl-2-oxoimidazolidin-1-yl)acetic acid (i-63)

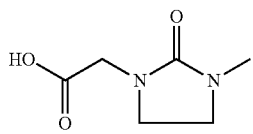

Intermediate 63 was prepared from commercially available N-methylethane-1,2-diamine using a procedure analogous to that used to prepare 1-62. $^1$HNMR (500 MHz, CDCl$_3$) δ: 7.21 (br s, 1H), 3.96 (s, 2H), 3.48-3.42 (m, 2H), 3.39-3.59 (m, 2H), 2.80 (s, 3H), LC-MS: m/z (ES) 159 (MH)$^+$.

INTERMEDIATE 64

2-(3-Methyl[1,2,4]triazolo[4,3-a]pyridin-8-yl)propanoic acid (i-64)

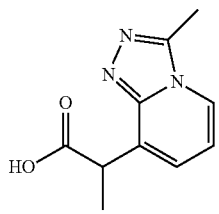

Step A: N'-(3-bromopyridin-2-yl)acetohydrazide

To a solution of 0.800 g (3.38 mmol) of 2,3-dibromopyridine in 10 mL of anhydrous 1,4-dioxane was added 0.325 g (10.1 mmol) of anhydrous hydrazine and the resulting mixture was heated to 85° C. for 8 h. The reaction mixture was cooled to ambient temperature then evaporated to dryness in vacuo. The crude residue was dissolved in anhydrous dichloromethane and cooled to −78° C. in a dry ice acetone bath under an atmosphere of nitrogen. Next, 1.0 mL (6.8 mmol) of triethylamine was added followed by 0.210 g (2.72 mmol) of acetyl chloride. The resulting mixture was allowed to warm to ambient temperature over 20 min then all volatiles were removed in vacuo. The residue was suspended in 20 mL of water and extracted with ethyl acetate (3×10 mL). The combined extracts were washed with brine, dried over magnesium sulfate, filtered and evaporated to afford the title compound (0.18 g, 23%). LC-MS: m/z (ES) 230, 232 (MH)$^+$ and 188, 190 (MH−COCH$_3$)$^+$.

Step B: 8-Bromo-3-methyl[1,2,4]triazolo[4,3-a]pyridine

To a solution of 0.17 g (0.74 mmol) of N'-(3-bromopyridin-2-yl)acetohydrazicle from step A in 40 mL of anhydrous toluene was added 3 mL of glacial acetic acid and the resulting mixture was heated to reflux for 20 h employing a Dean-Stark trap. The reaction mixture was cooled to ambient temperature then evaporated to dryness in vacuo to afford the title compound (0.13 g, 84%) LC-MS: m/z (ES) 212, 214 (MH)$^+$.

Step C: Benzyl 2-(3-methyl[1,2,4]triazolo[4,3-a]pyridin-8-yl)acrylate

To a solution of 0.13 g (0.61 mmol) of 8-bromo-3-methyl [1,2,4]triazolo[4,3-a]pyridine from Step B in 4 mL of anhydrous THF was added a solution of 0.36 g (0.80 mmol) of benzyl 2-(tributylstannyl)acrylate (see Intermediate 62, Step B) in 1 mL of anhydrous THF, 0.11 g (0.09 mmol) of tetrakis (triphenylphosphine)palladium(0) and 0.067 g (0.67 mmol) of copper(I)chloride. The reaction mixture was heated to 60° C. for 6 h, cooled and filtered through a pad of Celite®. The pad was washed with 15 mL of a dichloromethane and the combined filtrates were evaporated to dryness. The crude residue was purified by silica gel chromatography eluting with a 0-6% methanol in ethyl acetate gradient to afford the title compound (0.13 g, 73%). LC-MS: m/z (ES) 294 (MH)$^+$.

Step D: 2-(3-Methyl[1,2,4]triazolo[4,3-a]pyridin-8-yl)propanoic acid

To 0.040 mg (0.038 mmol) of 10% palladium on carbon was added a solution of (0.080 g, 0.27 mmol) of benzyl 2-(3-methyl[1,2,4]triazolo[4,3-a]pyridin-8-yl)acrylate prepared in Step C above in 4 mL of methanol. The resulting suspension was stirred under an atmosphere of hydrogen (1 atmosphere) for 6 h. The residue was filtered through a pad of Celite® and the pad was washed cold methanol. The combined filtrates were evaporated under reduced pressure to give yield the title compound (0.043 g, 77%). LC-MS: iniz (ES) 206 (MH)$^+$.

INTERMEDIATE 65

4-Methoxy-2-(1H-pyrazol-1-yl)butanoic acid (i-65)

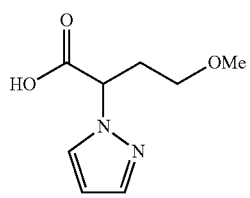 [SMILES: COCCC(C(=O)O)n1cccn1]

Step A: Methyl 4-methoxy-2-(1H-pyrazol-1-yl)butanoate

To a stirred, cooled (−78° C.) solution of 1.32 g (10.0 mmol) of methyl 4-methoxybutanoate in 15 mL of anhydrous THF under an atmosphere of nitrogen was added 10.5 mL (10.5 mmol) of a 1.0 M solution of LiHMDS in tetrahydrofuran. The resulting mixture was stirred for 1 h, then 1.09 g (10 mmol) of chlorotrimethylsilane was added. After stirring for 20 min, 1.78 g (10.0 mmol) of solid N-bromosuccinimide was added and the mixture was stirred for 2 h at −78° C., then slowly warmed to ambient temperature over 40 min. The reaction was quenched with a saturated aqueous ammonium chloride solution and then the aqueous phase was extracted with ethyl acetate (2×20 mL). The combined organic layers were washed with brine, dried over sodium sulfate, filtered and evaporated to dryness in vacuo. The crude residue was dissolved in 15 mL of DMF and 5.5 g (40 mmol) of potassium carbonate followed by 3.4 g (50 mmol) of 1H-pyrazole were added. The resulting mixture was heated to 80° C. for 40 min, then cooled to ambient temperature. The reaction was diluted with 75 mL of water and extracted with ethyl acetate (3×50 mL). The combined extracts were washed with brine, dried over magnesium sulfate, filtered and evaporated to dryness in vacuo. The crude residue was purified by reverse phase HPLC (TMC Pro-Pac C18; 0-75% 0.1% trifluoroacetic acid in acetonitrile/0.1% trifluoroacetic acid in water gradient) to yield the title compound (0.26 g, 13%). LC-MS: m/z (ES) 199 (MH)+.

Step B: 4-Methoxy-2-(1H-pyrazol-1-yl)butanoic acid

To a stirred solution of 0.045 g (0.23 mmol) of methyl 4-methoxy-2-(1H-pyrazol-1-yl)butanoate from step A in 2 mL of methanol was added a solution of 0.032 g (0.57 mmol) of potassium hydroxide in 0.5 mL of water. The mixture was stirred at ambient temperature for 1.5 h then acidified with a 2 N hydrochloric acid solution until a pH of 4 was achieved. The mixture was evaporated to remove all volatiles then extracted with ethyl acetate. The combined extracts were washed with brine, dried over magnesium sulfate, filtered and evaporated to dryness to afford the title compound (0.040 g, 95%). LC-MS: m/z (ES) 185 (MH)+.

INTERMEDIATE 66

(5S)-6,7-Dihydro-5H-pyrrolo[1,2-b][1,2,4]triazole-5-carboxylic acid (i-66)

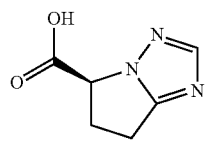 [SMILES: O=C(O)[C@@H]1CCc2ncnn21]

Step A:
(5S)-1-Amino-5-[(trityloxy)methyl]pyrrolidin-2-one

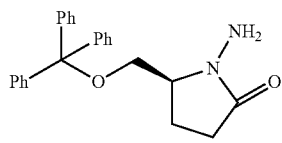 [SMILES: NN1C(=O)CC[C@H]1COC(c1ccccc1)(c1ccccc1)c1ccccc1]

To a cooled (0° C.) solution of 0.550 g (1.54 mmol) of (S)-tritylhydroxymethylpyrrolidinone in 10 mL of 1,2-dimethoxyethane under an atmosphere of nitrogen was added 0.123 g (3.08 mmol) of a 60% sodium hydride suspension in mineral oil. After stirring for 30 min, a solution of 0.828 g (3.85 mmoL) of 2-[(aminooxy)sulfonyl]-1,3,5-trimethylbenzene in 5 mL of diethyl ether was added in small portions over 30 min. The reaction mixture was allowed to warm to ambient temperature overnight then filtered. The filtrand was washed with diethyl ether and the filtrate was washed successively with a saturated aqueous sodium bicarbonate solution and brine. The organic layer was then dried over magnesium sulfate, filtered and evaporated in vacuo to afford the title compound as a colorless solid. The solid is contaminated with mineral oil form the sodium hydride and weighed 0.6 g (quantitative yield). LC-MS: m/z (ES) 395 (M+Na)+.

Step B: (5S)-5-[(Trityloxy)methyl]-6,7-dihydro-5H-pyrrolo[1,2-b][1,2,4]triazole

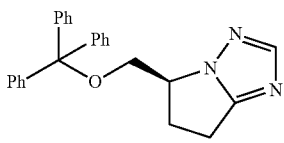 [SMILES: c1ccc(C(OC[C@@H]2CCc3ncnn32)(c2ccccc2)c2ccccc2)cc1]

To a stirred solution of 0.540 g (1.45 mmol) of (5S)-1-amino-5-[(trityloxy)methyl]pyrrolidin-2-one from step A in 5 mL of anhydrous DMF was added 0.327 g (7.25 mmol) of formamide followed by 0.050 g (036 mmol) of zinc(II)chloride. The resulting mixture was heated to 160° C. for 48 h, cooled to ambient temperature and diluted with 25 mL of ethyl acetate. The solution was washed sequentially with an aqueous sodium bicarbonate solution, water and then brine and the organic layer dried over magnesium sulfate. The mixture was then filtered, evaporated to dryness in vacuo and purified by silica gel chromatography eluting with a 0-100% ethyl acetatae in hexanes gradient to afford the title compound (0.27 g, 49%). LC-MS: m/z (ES) 382 (MH)+.

Step C: (5S)-6,7-Dihydro-5H-pyrrolo[1,2-b][1,2,4]triazol-5-ylmethanol

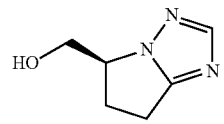

The product form step 13 above, 0.27 g (0.71 mmol) of (5S)-5-[(trityloxy)methyl]-6,7-dihydro-5H-pyrrolo[1,2-b][1,2,4]triazole, was dissolved in 35 mL of a 4.0 M solution of hydrogen chloride in anhydrous 1,4-dioxane. The reaction mixture was stirred for 10 min, quenched with 20 mL of methanol, then evaporated to dryness in vacuo. The residue was purified by reverse phase HPLC (TMC Pro-Pac C18; 0-90% 0.1% trifluoroacetic acid in acetonitrile/0.1% trifluoroacetic acid in water gradient) to yield the title compound (0.050 g, 50%). LC-MS: m/z (ES) 140 (MH)+.

Step D: ((5S)-6,7-Dihydro-5H-pyrrolo[1,2-b][1,2,4]triazole-5-carboxylic acid

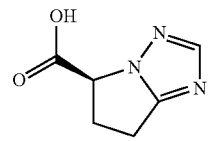 [SMILES: O=C(O)[C@@H]1CCc2ncnn21]

To a stirred solution of 0.025 g (0.18 mmol) of (5S)-6,7-dihydro-5H-pyrrolo[1,2-b][1,2,4]triazol-5-ylmethanol from step C in 1 mL of a pH 6.7 aqueous phosphate buffer and 1 mL of acetonitrile was added 0.0020 g (0.013 mmol) of 2,2,6,6-tetramethylpiperidine 1-oxyl, 0.033 g (0.36 mmol) of sodium chlorite (33 mg, 0.36 mmol) and 0.0044 mL (0.0036 mmol) of sodium hypochlorite. The resulting mixture was stirred at 35° C. for 72 h, then concentrated to dryness in vacuo. The residue was dissolved in 1 mL (4 mmol) of a 4.0 M solution of hydrogen chloride in anhydrous 1,4-dioxane and concentrated in vacuo. The crude residue was purified by reverse phase HPLC (TMC Pro-Pac C18; 0-70% 0.1% trifluoroacetic acid in acetonitrile/0.1% trifluoroacetic acid in water gradient) to yield the title compound as the TFA salt. The product was then dissolved in 1 mL (4 mmol) of a 4.0 M solution of hydrogen chloride in anhydrous 1,4-dioxane and concentrated in vacuo to afford the title compound as the hydrogen chloride salt. LC-MS: m/z (ES) 154 (MH)$^+$.

INTERMEDIATE 67

Tert-butyl(2S,5R)-2-(4-{[(2S)-2-aminopropanoyl] amino}benzyl)-5-[(R)-hydroxy(pyridin-3-yl)methyl] pyrrolidine-1-carboxylate (i-67)

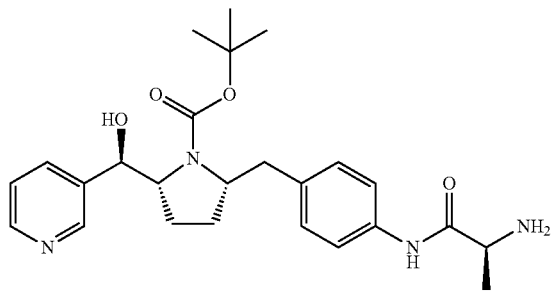 [SMILES: C[C@H](N)C(=O)Nc1ccc(C[C@@H]2CC[C@H]([C@H](O)c3cccnc3)N2C(=O)OC(C)(C)C)cc1]

Step A: Tert-butyl(2S,5R)-2-{4-[((2S)-2-{[(9H-fluoren-9-yloxy)carbonyl]amino}propanoyl)amino]benzyl}-5-[(R)-hydroxy(pyridin-3-yl)methyl]pyrrolidine-1-carboxylate To a solution of 1.85 g (4.82 mmol) of intermediate 17 in 20 mL of dichloromethane was added 1.0 mL (7.24 mmol) of triethylamine followed by 1.67 g (5.07 mmol) of commercially available 9H-fluoren-9-yl[(1S)-2-chloro-1-methyl-2-oxoethyl]carbamate. The resulting mixture was stirred for 1.5 h then all volatiles were removed in vacuo. The residue was diluted with water and then extracted with ethyl acetate. The combined organic layers were washed with brine, dried over magnesium sulfate, filtered and evaporated to afford the crude title compound which was used without further purification (3.2 g). LC-MS: m/z (ES) 677 (MH)$^+$.

Step B: Tert-butyl(2S,5R)-2-(4-{[(2S)-2-aminopropanoyl]amino}benzyl)-5-[(R)-hydroxy(pyridin-3-yl) methyl]pyrrolidine-1-carboxylate To a stirred solution of 3.15 g (4.65 mmol) of tert-butyl(2S, 5R)-2-{4-[((2S)-2-{[(9H-fluoren-9-yloxy)carbonyl] amino}propanoyl)amino]benzyl}-5-[(R)-hydroxy(pyridin-3-ylmethyl]pyrrolidine-1-carboxylate from step A in 3 mL of anhydrous THF was added 0.396 g (4.65 mmol) of piperidine. The resulting mixture was heated to 35° C. under an atmosphere of nitrogen for 2 h then all volatiles were removed in vacuo to afford the crude title compound which was used without further purification. LC-MS: m/z (ES) 455 (MH)$^+$.

INTERMEDIATE 68

Tert-butyl(2R,5S)-2-[(R)-hydroxy(pyridin-3-yl)methyl]-5-(4-{[(2S)-2-(methylamino)propanoyl] amino}benzyl)pyrrolidine-1-carboxylate (i-68)

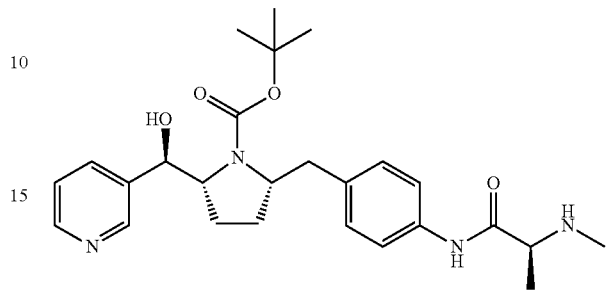

Step A: Tert-butyl(2S,5R)-2-[4-({(2S)-2-[[(9H-fluoren-9-yloxy)carbonyl](methyl)amino] propanoyl}amino)benzyl]-5-[(R)-hydroxy(pyridin-3-yl)methyl]pyrrolidine-1-carboxylate To a stirred solution of 0.192 g (0.5 mmol) of intermediate 17 in 4 mL of dichloromethane under an atmosphere of nitrogen was added 0.203 g (0.625 mmol) of commercially available (2S)-2-[[(9H-fluoren-9-yloxy)carbonyl](methyl) amino]propanoic acid followed by 0.014 g (0.10 mmol) of 1-hydroxy-7-azabenzotriazole and 0.144 g (0.750 mmol) of 1-(3-dimethylaminopropyl)-3-ethylcarbodiimide hydrochloride. The resulting suspension was stirred at ambient temperature for 24 h. The crude reaction mixture was diluted with 25 mL of dichloromethane, washed with water then dried over magnesium sulfate. The mixture was filtered and evaporated to dryness in vacuo to afford the crude title compound which was used without further purification. LC-MS: m/z (ES) 691 (MH)$^+$.

Step B: Tert-butyl(2R,5S)-2-[(R)-hydroxy(pyridin-3-yl)methyl]-5-(4-{[(2S)-2-(methylamino)propanoyl] amino}benzyl)pyrrolidine-1-carboxylate To a solution of 0.410 g (0.593 mmol) of tert-butyl(2S,5R)-2-[4-({(2S)-2-[[(9H-fluoren-9-yloxy)carbonyl](methyl) amino]propanoyl}amino)benzyl]-5-[(R)-hydroxy(pyridin-3-yl)methyl]pyrrolidine-1-carboxylate from step A in 3 mL of anhydrous THF was 0.152 g (1.78 mmol) of piperidine. The resulting mixture was stirred at ambient temperature for 24 h and then was diluted with 25 mL of dichloromethane. The mixture was washed with water then dried over magnesium sulfate. The mixture was filtered and evaporated to dryness in vacuo to afford the crude title compound which was used without further purification. LC-MS: m/z (ES) 469 (MH)$^+$.

INTERMEDIATE 69

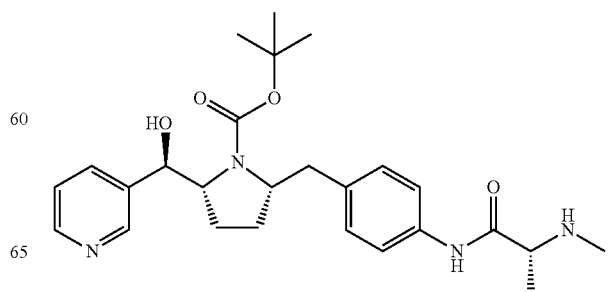

Intermediate 69 (i-69) was prepared from i-17 and commercially available (2R)-2-[[(9H-fluoren-9-yloxy)carbonyl](methyl)amino]propanoic acid following the procedure outlined for the synthesis of i-68, LC-MS: m/z (ES) 469 (MH)+.

Biological Assays:

The following in vitro assays are suitable for screening compounds that have selective β3 agonist activity:

Functional Assay: cAMP production in response to ligand is measured according to Barton, et al. (1991, Agonist-induced desensitization of D2 dopamine receptors in human Y-79 retinoblastoma cells. Mol. Pharmacol. v3229:650-658) modified as follows, cAMP production is measured using a homogenous time-resolved fluorescence resonance energy transfer immunoassay (LANCE™, Perkin Elmer) according to the manufacture's instructions. Chinese hamster ovary (CHO) cells, stably transfected with the cloned β-adrenergic receptor (β1, β2 or β3) are harvested after 3 days of subculturing. Harvesting of cells is done with Enzyme-free Dissociation Media (Specialty Media). Cells are then counted and resuspended in assay buffer (Hank's Balanced salt solution supplemented with 5 mM HEPES, 01% BSA) containing a phosphodiesterase inhibitor (IBMX, 0.6 mM). The reaction is initiated by mixing 6,000 cells in 6 μL with 6 μL Alexa Fluor labeled cAMP antibody (LANCE™ kit) which is then added to an assay well containing 12 μL of compound (diluted in assay buffer to 2× final concentration). The reaction proceeds for 30 min at room temperature and is terminated by the addition of 24 ul detection buffer (LANCE™ kit). The assay plate is then incubated for 1 h at room temperature and time-resolved fluorescence measured on a Perkin Elmer Envision reader or equivalent. The unknown cAMP level is determined by comparing fluorescence levels to a cAMP standard curve.

The non-selective, full agonist β-adrenergic ligand isoproterenol is used at all three receptors to determine maximal stimulation. The human β3 adrenergic receptor (AR) selective ligand (S)-N-[4-[2-[[2-hydroxy-3-(4-hydroxyphenoxy)propyl]amino]ethyl]-phenyl]-4-iodobenzenesulfonamide is used as a control in all assays. Isoproterenol is titrated at a final concentration in the assay of 10-10 M to 10-5 and the selective ligand (S)-N-[4-[2-[[2-hydroxy-3-(4-hydroxyphenoxy)propyl]amino]ethyl]phenyl]-4-iodobenzenesulfonamide is titrated at the β3 receptor at concentration of 10-10 M to 10-5 M. Unknown ligands are titrated at all 3 β-adrenergic receptor subtypes at a final concentration in the assay of 10-10 M to 10-5 M to determine the $EC_{50}$. The $EC_{50}$ is defined as the concentration of compound that gives 50% activation of its own maximum. Data are analyzed using Microsoft Excel and Graphpad Prism or an internally developed data analysis software package.

Binding Assay: Compounds are also assayed at the β1 and β2 receptors to determine selectivity. All binding assays are run using membranes prepared from CHO cells recombinantly expressing β1 or β2 receptors. Cells are grown for 3-4 days post splitting; the attached cells are washed with PBS and then lysed in 1 mM Tris, pH 7.2 for 10 min on ice. The flasks are scraped to remove the cells and the cells then homogenized using a Teflon/glass homogenizer. Membranes are collected by centrifuging at 38,000×g for 15 min at 4° C. The pelleted membranes are resuspended in TME buffer (50 mM Tris, pH 7.4, 5 mM $MgCl_2$, 2 mM EDTA) at a concentration of 1 mg protein/ml. Large batches of membranes can be prepared, aliquoted and stored at −70° C. for up to a year without loss of potency. The binding assay is performed by incubating together membranes (2-5 μg of protein), the radiolabelled tracer $^{125}$I-cyanopindolol ($^{125}$I-CYP, 45 pM), 200 μg of WGA-PVT SPA beads (GE Healthcare) and the test compounds at final concentrations ranging from 10-10 M to 10-5 M in a final volume of 200 μL of TME buffer containing 0.1% BSA. The assay plate is incubated for 1 h with shaking at room temperature and then placed in a Perkin Elmer Trilux scintillation counter. The plates are allowed to rest in the Trilux counter for approximately 10 h in the dark prior to counting. Data are analyzed using a standard 4-parameter non-linear regression analysis using either Graphpad Prism software or an internally developed data analysis package. The $IC_{50}$ is defined as the concentration of the compound capable of inhibiting 50% of the binding of the radiolabelled tracer ($^{125}$I-CYP). A compound's selectivity for the β3 receptor may be determined by calculating the ratio ($IC_{50}$ β1 AR, β2 AR)/($EC_{50}$ β3 AR).

EXAMPLE 1

2-2-Amino-1,3-thiazol-4-yl)-N-[4-({(2S,5R)-5-[(R)-hydroxy(pyridin-3-yl)methyl]pyrrolidin-2-yl}methyl)phenyl]acetamide, trfluoroacetic acid salt

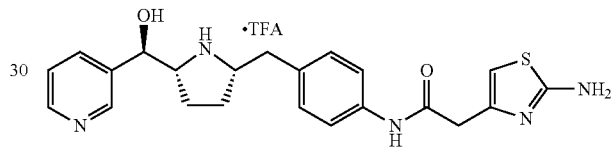

Step A: Tert-butyl(2S,5R)-2-{4-[({2-[(tert-butoxycarbonyl)amino]-1,3-thiazol-4-yl}acetyl)amino]benzyl}-5-[(R)-{[tert-butyl(dimethyl)silyl]oxy}(pyridin-3-yl)methyl]pyrrolidine-1-carboxylate, trifluoroacetic acid salt

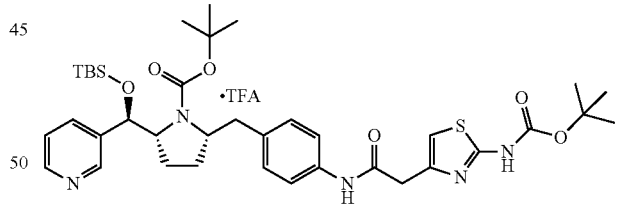

To a solution of 0.030 g (0.060 mmol) of Intermediate 4 and 0.017 g (0.066 mmol) of ({2-[(tert-butoxycarbonyl)amino]-1,3-thiazol-4-yl}acetic acid in 1 mL of anhydrous N,N-dimethylformamide under an atmosphere of nitrogen was added 0.030 mL (0.18 mmol) of diisopropylethylamine, 0.12 mL (0.072 mmol) of a 0.6 M solution of 1-hydroxy-7-azabenzotriazole in N,N-dimethylformamide and 0.014 g (0.072 mmol) of 1-(3-dimethylaminopropyl)-3-ethylcarbodiimide hydrochloride. The resulting suspension was stirred at ambient temperature for 24 h. The crude reaction mixture was purified by reverse phase HPLC (TMC Pro-Pac C18; 10-100% 0.1% trifluoroacetic acid in acetonitrile/0.1% trifluoroacetic acid in water gradient) to give the title compound as a yellow solid. LC-MS: m/z (ES) 738.2 (MH)+.

Step B: 2-(2-Amino-1,3-thiazol-4-yl)-N-[4-({(2S,5R)-5-[(R)-hydroxy(pyridin-3-yl)methyl]pyrrolidin-2-yl}methyl)phenyl]acetamide, trifluoroacetic acid salt

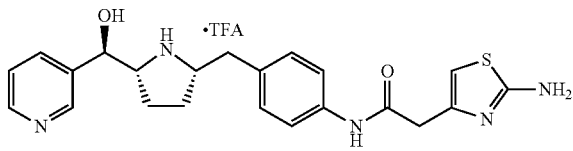 [SMILES: Nc1nc(CC(=O)Nc2ccc(C[C@@H]3CC[C@H]([C@H](O)c4cccnc4)N3)cc2)cs1]

A solution of 0.040 g (0.047 mmol) of tert-butyl(2S,5R)-2-{4-[({2-[(tert-butoxycarbonyl)amino]-1,3-thiazol-4-yl}acetyl)amino]benzyl}-5-[(R)-{[tert-butyl(dimethyl)silyl]oxy}(pyridin-3-yl)methyl]pyrrolidine-1-carboxylate, trifluoroacetic acid salt from step A in 2 mL of a 3:3:1 mixture of acetonitrile:trifluoroacetic acid:water was heated to 55° C. for 2 h. The crude reaction mixture was purified by reverse phase HPLC (TMC Pro-Pac C18; 0-60% 0.1% trifluoroacetic acid in acetonitrile/ 0.1% trifluoroacetic acid in water gradient). The pure fractions were lyophilized overnight to give the title compound as a white solid. LC-MS: m/z (ES) 424.3 (MH)⁺.

Using the Beta-3 agonist in vitro functional assay described above the human Beta-3 agonist functional activity of Example 1 was determined to be less than 10 nM.

EXAMPLE 2

N-[4-({(2S,5R)-5-[(R)-Hydroxy(pyridin-3-yl)methyl]pyrrolidin-2-yl}methyl)phenyl]-2-(2-oxopyrrolidin-1-yl)acetamide, trfluoroacetic acid salt

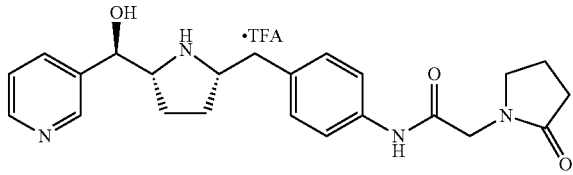 [SMILES: O=C(CN1CCCC1=O)Nc1ccc(C[C@@H]2CC[C@H]([C@H](O)c3cccnc3)N2)cc1]

Step A: Tert-butyl(2R,5S)-2-[(R)-hydroxy(pyridin-3-yl)methyl]-5-(4-{[(2-oxopyrrolidin-1-yl)acetyl]amino}benzyl)pyrrolidine-1-carboxylate, trifluoroacetic acid salt

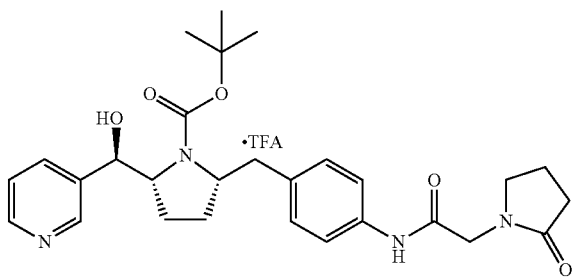 [SMILES: CC(C)(C)OC(=O)N1[C@H](Cc2ccc(NC(=O)CN3CCCC3=O)cc2)CC[C@@H]1[C@H](O)c1cccnc1]

To a solution of 0.050 g (0.130 mmol) of Intermediate 17 and 0.028 g (0.196 mmol) of (2-oxopyrrolidin-1-yl)acetic acid in 1 mL of anhydrous N,N-dimethylformamide under an atmosphere of nitrogen was added 0.021 mg (0.156 mmol) of 1-hydroxy-7-azabenzotriazole and 0.030 g (0.156 mmol) of 1-(3-dimethylaminopropyl)-3-ethylcarbodiimide hydrochloride. The resulting suspension was stirred at ambient temperature for 24 h. The crude reaction mixture was purified by reverse phase HPLC (TMC Pro-Pac C18; 10-100% 0.1% trifluoroacetic acid in acetonitrile/0.1% trifluoroacetic acid in water gradient) to give the title compound as a white solid 0.061 g, 75%). LC-MS: m/z (ES) 509.2 (MH)⁺.

Step B: N-[4-({(2S,5R)-5-[(R)-Hydroxy(pyridin-3-yl)methyl]pyrrolidin-2-yl}methyl)phenyl]-2-(2-oxopyrrolidin-1-yl)acetamide, trfluoroacetic acid salt

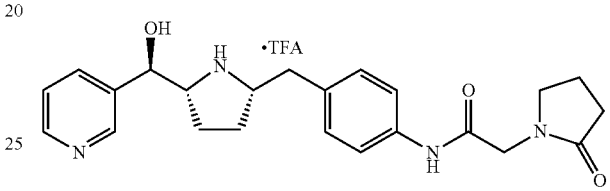

To a solution of 0.050 g (0.080 mmol) of tert-butyl(2R,5S)-2-[(R)-hydroxy(pyridin-3-yl)methyl]-5-(4-{[(2-oxopyrrolidin-1-yl)acetyl]amino}benzyl)pyrrolidine-1-carboxylate, trifluoroacetic acid salt from step A in 0.5 mL of isopropanol under an atmosphere of nitrogen was added 2.0 mL of a 4.0 M solution of anhydrous hydrogen chloride in 1,4-dioxane. The reaction mixture was stirred for 1 h and then evaporated to dryness in vacuo. The crude reaction mixture was purified by reverse phase HPLC (TMC Pro-Pac C18; 0-75% 0.1% trifluoroacetic acid in acetonitrile/0.1% trifluoroacetic acid in water gradient) to yield the title compound as a white solid. The pure fractions were lyophilized overnight to give the title compound as a white solid (0.035 g, 85%). ¹H-NMR (500 MHz, CD₃OD) δ 9.05 (s, 1H), 8.88 (d, J=5.5 Hz, 1H), 8.80 (d, J=8.2 Hz, 1H), 8.18-8.15 (m, 1H), 7.54 (d, J=8.5 Hz, 2H), 7.27 (d, J=8.5 Hz, 2H), 5.23 (d, J=6.9 Hz, 1H), 4.13 (s, 3H), 3.98-3.93 (m, 1H), 3.83-3.75 (m, 1H), 3.57-3.53 (m, 2H), 3.19 (dd, J=13.8, 6.2 Hz, 1H), 2.99 (dd, J=13.6, 8.8 Hz, 1H), 2.45 (t, J=8.1 Hz, 1H), 2.15-1.90 (m, 6H). LC-MS: m/z (ES) 409.3 (MH)⁺.

Using the Biological Assays (β₃AR-cAMP) described above, the human Beta-3 agonist functional activity of Example 2 was determined to be less than 100 nM.

EXAMPLES 3-90

Following similar procedures outlined in the examples above, the examples in the following table were prepared.

Using the Biological Assays described above, the human β3 functional activity of each compound was determined and shown in the following table as the following ranges:

less than 1 nM (+);

1-10 nM (++);

11-100 nM (+++);

101-1000 nM (++++); and greater than 1000 nM but less than 3000 nM (+++++).

TABLE 2

| Example | *Diastereomer | R | MW | MS (MH)+ | Human β3 functional |
|---|---|---|---|---|---|
| 3 | R | thiazole-2-amine | 423.2 | 424.3 | ++ |
| 4 | S | 5-phenyl-1H-1,2,4-triazole | 468.6 | 469.4 | ++ |
| 5 | S | 1H-indazol-1-yl | 441.5 | 442.4 | +++ |
| 6 | S | 2H-indazol-2-yl | 441.5 | 442.4 | +++ |
| 7 | S | 2H-benzotriazol-2-yl | 442.5 | 443.4 | +++ |
| 8 | S | 4-Bn-1-oxo-phthalazin-2-yl | 559.7 | 560.5 | ++ |
| 9 | S | 4-Me-1-oxo-phthalazin-2-yl | 483.6 | 484.4 | ++ |
| 10 | S | 2,5-diMe-thiazol-4-yl | 436.6 | 437.3 | +++ |
| 11 | S | 2-Me-4-oxo-quinazolin-3-yl | 483.6 | 484.4 | ++ |

TABLE 2-continued

| Example | *Diastereomer | R | MW | MS (MH)+ | Human β3 functional |
|---|---|---|---|---|---|
| 12 | S | (3-oxo-quinazolin-3-yl-methyl) | 469.5 | 470.4 | ++ |
| 13 | S | (2-oxo-quinazolin-1-yl-methyl) | 469.5 | 470.4 | ++ |
| 14 | S | (pyridin-2-yl-methyl) | 402.5 | 403.1 | +++ |
| 15 | S | (2-methyl-thiazol-4-yl-methyl) | 422.5 | 423.2 | +++ |
| 16 | S | (2-phenyl-1H-indol-3-yl-methyl) | 516.6 | 517.4 | +++ |
| 17 | S | (1H-benzimidazol-2-yl-methyl) | 441.2 | 442.4 | +++ |
| 18 | S | (2-phenyl-benzimidazol-1-yl-methyl) | 517.3 | 518.5 | +++ |
| 19 | S | (1H-indol-3-yl-methyl) | 440.2 | 441.5 | ++ |
| 20 | S | (3-amino-1,2,4-triazol-1-yl-methyl) | 407.2 | 408.4 | ++ |

TABLE 2-continued

| Example | *Diastereomer | R | MW | MS (MH)+ | Human β3 functional |
|---|---|---|---|---|---|
| 21 | S | thieno[2,3-d]pyrimidinone with 5,6-diMe | 503.2 | 504.5 | ++ |
| 22 | S | CH2-pyrimidin-2-yl | 403.2 | 404.4 | +++ |
| 23 | S | CH2-(5-Me-1,2,4-triazol-3-yl) | 406.2 | 407.5 | ++++ |
| 24 | S | CH2-(5-(4-Cl-phenyl)-1,2,4-triazol-3-yl) | 502.1 | 503.1 | +++ |
| 25 | S | CH2-(5-(pyridin-4-yl)-1,2,4-triazol-3-yl) | 469.2 | 470.4 | +++ |
| 26 | S | CH2-(5-Bn-1,2,4-triazol-3-yl) | 482.2 | 483.4 | +++ |
| 27 | S | CH2-(5-(thiazol-4-yl)-1,2,4-triazol-3-yl) | 475.2 | 476 | ++ |
| 28 | S | CH2-(6-Me-pyridin-2-yl) | 416.2 | 417.4 | ++++ |
| 29 | S | CH2-(2-CF3-thiazol-4-yl) | 476.2 | 477 | +++ |
| 30 | S | 1-(thiazol-2-yl)pyrrolidin-2-yl | 463.6 | 464.2 | ++ |

TABLE 2-continued

| Example | *Diastereomer | R | MW | MS (MH)+ | Human β3 functional |
|---|---|---|---|---|---|
| 31 | S | 3-methoxyphenyl-pyrrolidin-2-yl | 486.6 | 487.3 | ++ |
| 32 | S | 2-benzylphenyl | 491.6 | 492.1 | +++ |
| 33 | S | 2-(1H-imidazol-2-yl)phenyl | 453.5 | 454.1 | +++ |
| 34 | S | 2-(benzothiazol-2-yl)phenyl | 520.6 | 521.3 | +++ |
| 35 | S | 2-(2H-1,2,3-triazol-2-yl)phenyl | 454.5 | 455.1 | +++ |
| 36 | S | 2-cyclohexylphenyl (with α-methyl) | 469.6 | 470.4 | ++++ |
| 37 | S | 2-(pyrrolidin-1-yl)phenyl | 456.3 | 457.5 | ++++ |
| 38 | S | (1H-1,2,4-triazol-1-yl)methyl | 392 | 393 | +++ |

TABLE 2-continued

Structure: 3-pyridyl-CH(OH)-[pyrrolidine with NH·TFA]-CH2-C6H4-NH-C(O)-R

| Example | *Diastereomer | R | MW | MS (MH)+ | Human β3 functional |
|---------|---------------|---|-----|----------|---------------------|
| 39 | S | -CH2-(2H-1,2,3-triazol-2-yl) | 392 | 393 | +++ |
| 40 | S | -CH2-(2-oxopyridin-1-yl) | 418.5 | 419.0 | ++ |
| 41 | S | -CH2-(pyrazin-2-yl) | 403.5 | 404.1 | +++ |
| 42 | S | -CH2-(2-oxopiperidin-1-yl) | 422.5 | 423.1 | +++ |
| 43 | S | -CH2-(2,5-dioxopyrrolidin-1-yl) | 422.5 | 423.1 | +++ |
| 44 | S | -CH2-(2-oxooxazolidin-3-yl) | 410.5 | 411.0 | +++ |
| 45 | S | -CH2-(2-oxothiazolidin-3-yl) | 426.5 | 427.1 | ++ |
| 46 | S | -CH2-(4-methyl-1H-1,2,3-triazol-1-yl) | 406 | 407 | +++ |
| 47 | S | -CH2-(4-hydroxypyrimidin-5-yl) | 419 | 420 | +++ |
| 48 | S | -CH2-(4-methoxypyrimidin-5-yl) | 433 | 434 | +++ |

TABLE 2-continued
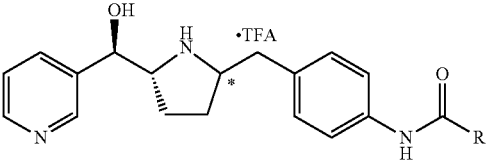
| Example | *Diastereomer | R | MW | MS (MH)+ | Human β3 functional |
|---|---|---|---|---|---|
| 49 | S | 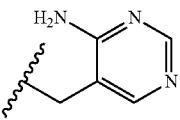 | 418 | 419 | +++ |
| 50 | S | 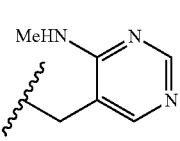 | 432 | 433 | ++++ |
| 51 | S | 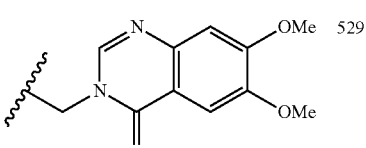 | 529 | 530 | ++ |
| 52 | S | 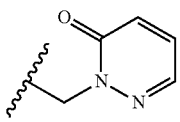 | 419 | 420 | ++ |
| 53 | S | 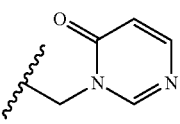 [SMILES: *Cn1cnccc1=O] | 419 | 420 | ++ |
| 54 | S | 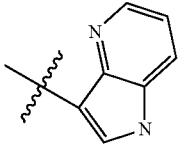 [SMILES: *c1c[nH]c2cccnc12] | 427 | 428 | ++++ |
| 55 | S | 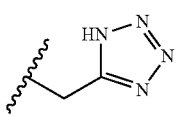 | 393 | 394 | +++ |
| 56 | S | 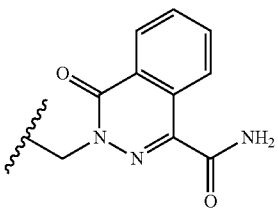 [SMILES: *Cn1nc(C(N)=O)c2ccccc2c1=O] | 512 | 513 | ++ |

TABLE 2-continued

| Example | *Diastereomer | R | MW | MS (MH)+ | Human β3 functional |
|---|---|---|---|---|---|
| 57 | S | (benzo-fused dihydropyrimidine-2,4-dione, N-CH2-) | 485 | 486 | ++ |
| 58 | S | (quinoxalin-2(1H)-one, N-CH2-) | 469 | 470 | ++ |
| 59 | S | (8-methylquinazolin-4(3H)-one, N-CH2-) | 483 | 484 | ++ |
| 60 | S | (pyrimidin-2(1H)-one, N-CH2-) | 419 | 420 | ++ |
| 61 | S | (uracil, N-CH2-) | 435 | 436 | ++ |
| 62 | S | (thymine, N-CH2-) | 449 | 450 | +++ |
| 63 | S | (pyrazin-2(1H)-one, N-CH2-) | 419 | 420 | +++ |

TABLE 2-continued

| Example | *Diastereomer | R | MW | MS (MH)+ | Human β3 functional |
|---|---|---|---|---|---|
| 64 | S | (4-oxo-quinazolin-3-yl-methyl) | 469 | 470 | ++ |
| 65 | S | (2,4-dioxo-quinazolin-3-yl-methyl) | 485 | 486 | ++ |
| 66 | S | (6-chloro-3-oxo-pyridazin-2-yl-methyl) | 453 | 453 (M)+ 455 (M + 2)+ | +++ |
| 67 | S | (1,4-dioxo-phthalazin-2-yl-methyl) | 485 | 486 | +++ |
| 68 | S | (4-methyl-furazan-3-yl-methyl) | 407 | 408 | +++ |
| 69 | S | (3,4-dimethyl-5-oxo-pyrazolin-1-yl-methyl) | 435 | 436 | +++ |
| 70 | S | (3-methyl-5-oxo-pyrazolin-1-yl-methyl) | 421 | 422 | +++ |
| 71 | S | (2,5-dioxo-imidazolidin-4-yl-methyl) | 423 | 424 | ++++ |

TABLE 2-continued

| Example | *Diastereomer | R | MW | MS (MH)+ | Human β3 functional |
|---|---|---|---|---|---|
| 72 | S | (2-thioxo-3-phenyl-imidazolidinone) | 515 | 516 | +++ |
| 73 | S | (3-oxo-1,2,4-triazole) | 408 | 409 | +++ |
| 74 | S | (2-thioxo-thiazole) | 440 | 441 | +++ |
| 75 | S | (thieno-pyrimidinone) | 475 | 476 | ++ |
| 76 | S | (1-methyl-pyrazolo-pyrimidinone) | 473 | 474 | ++ |
| 77 | S | (2-fluorophenyl-methyl) | 419 | 420 | +++ |
| 78 | S | (2,6-difluorophenyl-methyl) | 437 | 438 | ++ |
| 79 | S | (2,3-difluorophenyl-methyl) | 437 | 438 | +++ |

TABLE 2-continued

| Example | *Diastereomer | R | MW | MS (MH)+ | Human β3 functional |
|---|---|---|---|---|---|
| 80 | S | 5-methyl-1,2,4-oxadiazol-3-yl | 407 | 408 | +++ |
| 81 | S | 2-(pyridin-2-yl)thiazol-4-yl | 485 | 486 | +++ |
| 82 | S | 2-(pyridin-3-yl)thiazol-4-yl | 485 | 486 | ++ |
| 83 | S | -CH2CH2C(O)OMe | 397 | 398 | ++++ |
| 84 | S | -CH2CH2C(O)OH | 383 | 384 | ++++ |
| 85 | S | 2-oxo-1,3-oxazinan-3-ylmethyl | 424 | 425 | +++ |
| 86 | S | 3-methyl-2-oxoimidazolidin-1-ylmethyl | 423 | 424 | ++++ |
| 87 | S | 3-methyl-2-oxotetrahydropyrimidin-1-ylmethyl | 437 | 438 | ++++ |
| 88 | S | 5-hydroxy-1,3-dimethyl-1H-pyrazol-4-ylmethyl | 435 | 436 | ++++ |

TABLE 2-continued

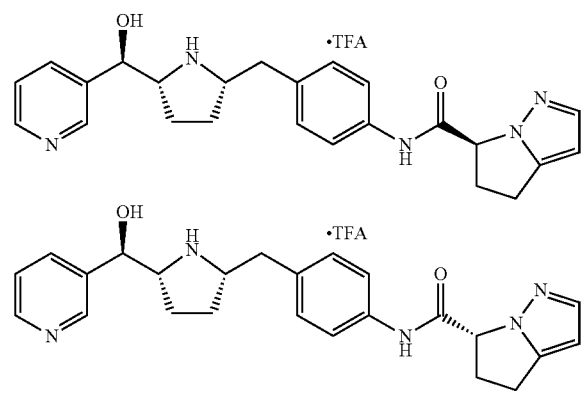

| Example | *Diastereomer | R | MW | MS (MH)+ | Human β3 functional |
|---|---|---|---|---|---|
| 89 | S | <image showing pyrazole carboxamide NH2> | 434 | 435 | +++ |
| 90 | S | <image showing pyrazole carboxamide NH2> | 434 | 435 | +++ |

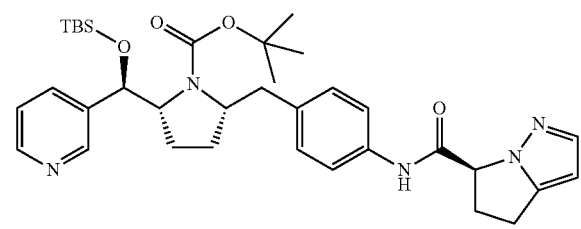

EXAMPLES 91 AND 92

(6S)-N-[4-({(2S,5R)-5-[(R)-Hydroxy(phenyl)methyl]pyrrolidin-2-yl}methyl)phenyl]-5,6-dihydro-4H-pyrrolo[1,2-b]pyrazole-6-carboxamide, trifluoroacetic acid salt and (6R)—N-[4-({(2S,5R)-5-[(R)-Hydroxy(phenyl)methyl]pyrrolidin-2-yl}methyl)phenyl]-5,6-dihydro-4H-pyrrolo[1,2-b]pyrazole-6-carboxamide, trifluoroacetic acid salt Step A: Tert-butyl(2R,5S)-2-[(R)-{[tert-butyl(dimethyl)silyl]oxy}(phenyl)methyl]-5-(4-{[(6S)-5,6-dihydro-4H-pyrrolo[1,2-b]pyrazol-6-ylcarbonyl]amino}benzyl)pyrrolidine-1-carboxylate and tert-butyl(2R,5S)-2-[(R)-{[tert-butyl(dimethyl)silyl]oxy}(phenyl)methyl]-5-(4-{[(6R)-5,6-dihydro-4H-pyrrolo[1,2-b]pyrazol-6-ylcarbonyl]amino}benzyl)pyrrolidine-1-carboxylate

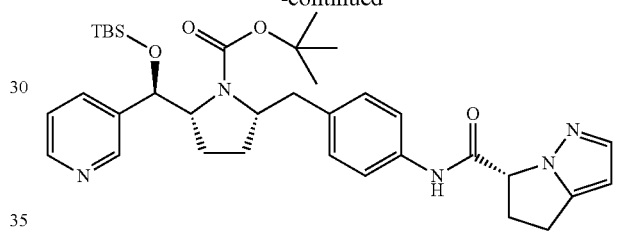

To a solution of 0.22 g (0.44 mmol) of i-4 and 0.100 g (0.64 mmol) of i-18 in 2 mL of anhydrous N,N-dimethylformamide under an atmosphere of nitrogen was added 0.12 mL (0.88 mmol) of N,N-diisopropylethylamine, 0.080 g (0.57 mmol) of 1-hydroxy-7-azabenzotriazole and 0.102 g (0.53 mmol) of 1-(3-dimethylaminopropyl)-3-ethylcarbodiimide hydrochloride. The resulting suspension was stirred at ambient temperature for 24 h. The crude reaction mixture was quenched with a sat. aq. sodium bicarbonate solution and then extracted with ethyl acetate (3×10 mL). The combined organic layers were washed with brine, dried over magnesium sulfate, filtered and evaporated in vacuo. The crude residue was purified by silica gel chromatography eluting with 45% ethyl acetate in hexanes to afford the title compounds as a mixture of diastereomers as a colorless gum. The two diastereomers were separated by chiral HPLC employing a Daicel CHIRALPAK® AD® column (eluent:17% IPA in Heptane). The first eluting diastereomer was designated as isomer 1 and is a colorless gum (0.10 g, 36%): LC-MS: m/z (ES) 632.2 (MH)+. The second eluting diastereomer was designated as isomer 2 and is a colorless foam (0.095 g, 34%). LC-MS: m/z (ES) 632.2 (MH)+.

Step B: (6S and 6R)—N-[4-({(2S,5R)-5-[(R)-Hydroxy(phenyl)methyl]pyrrolidin-2-yl}methyl)phenyl]-5,6-dihydro-4H-pyrrolo[1,2-b]pyrazole-6-carboxamide, trifluoroacetic acid salt

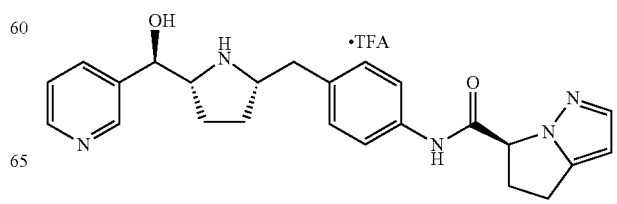

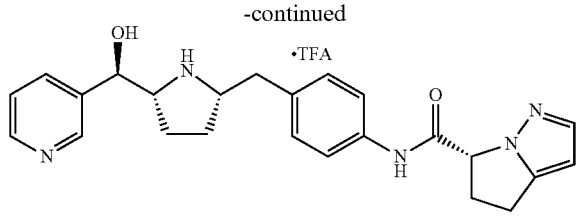

Step B (Isomer 1): (6S)-N-[4-({(2S,5R)-5-[(R)-Hydroxy(phenyl)methyl]pyrrolidin-2-yl}methyl)phenyl]-5,6-dihydro-4H-pyrrolo[1,2-b]pyrazole-6-carboxamide, trifluoroacetic acid salt To a solution of 0.100 g (0.15 mmol) of isomer 1 from step A above in 2 mL of a 3 to 3 to 1 mixture of acetonitrile to trifluoroacetic acid to water was heated to 55° C. for 2 h. The crude reaction mixture was purified by reverse phase HPLC (TMC Pro-Pac C18; 0-50% 0.1% trifluoroacetic acid in acetonitrile/0.1% trifluoroacetic acid in water gradient). The pure fractions were lyophilized overnight to afford a single diastereomer, designated as Example 91, of the title compound as a white solid. $^1$H-NMR (500 MHz, CD$_3$OD) δ 8.76 (s, 1H), 8.63 (d, J=5.3 Hz, 1H), 8.22 (d, J=8.0 Hz, 1H), 7.71 (dd, J=8.1, 5.2 Hz, 1H), 7.58 (d, J=8.5 Hz, 2H), 7.53 (d, J=1.8 Hz, 1H), 7.26 (d, J=8.5 Hz, 2H), 6.06 (s, 1H), 5.02-5.00 (m, 1H), 4.94 (d, J=8.0 Hz, 1H), 3.86 (q, J=8.3 Hz, 1H), 3.80-3.74 (m, 1H), 3.14 (dd, J=13.6, 6.2, Hz, 1H), 3.07-2.90 (m, 4H), 2.77-2.70 (m, 1H), 2.12-2.06 (m, 1H), 1.94-1.80 (m, 3H). LC-MS: m/z (ES) 418.4 (MH)$^+$.

Using the Biological Assays described above, the human Beta-3 agonist functional activity of Example 91 was determined to be less than 10 nM.

Step B (Isomer 2): (6R)—N-[4-({(2S,5R)-5-[(R)-Hydroxy(phenyl)methyl]pyrrolidin-2-yl}methyl)phenyl]-5,6-dihydro-4H-pyrrolo[1,2-b]pyrazole-6-carboxamide, trifluoroacetic acid salt The same procedure was employed for the deprotection of isomer 2 from step A above to afford a single diastereomer, designated as Example 92, of the title compound as a white solid. LC-MS: m/z (ES) 418.4 (MH)$^+$.

Using the Biological Assays described above, the human Beta-3 agonist functional activity of Example 92 was determined to be less than 100 nM.

EXAMPLES 93 AND 94

(2S)-N-[4-({(2S,5R)-5-[(R)-hydroxy(pyridin-3-yl)methyl]pyrrolidin-2-yl}methyl)phenyl]-2-pyridin-2-ylpropanamide and (2R)—N-[4-({(2S,5R)-5-[(R)-hydroxy(pyridin-3-yl)methyl]pyrrolidin-2-yl}methyl)phenyl]-2-pyridin-2-ylpropanamide, trifluoroacetic acid salt

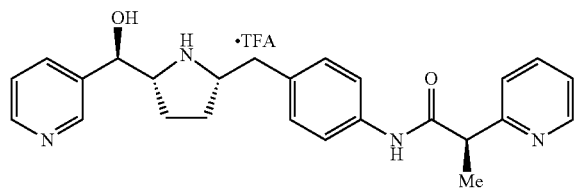

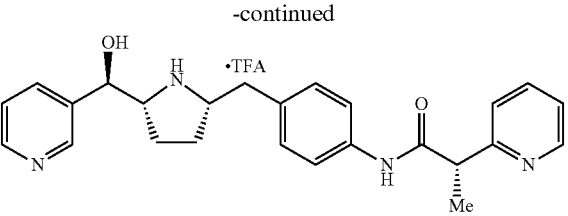

Step A: Tert-butyl(2R,5S)-2-[(R)-{[tert-butyl(dimethyl)silyl]oxy}(pyridin-3-yl)methyl]-5-(4-{[(2R)-2-pyridin-2-ylpropanoyl]amino}benzyl)pyrrolidine-1-carboxylate and tert-butyl(2R,5S)-2-[(R)-{[tert-butyl(dimethyl)silyl]oxy}(pyridin-3-yl)methyl]-5-(4-{[(2S)-2-ylpropanoyl]amino}benzyl)pyrrolidine-1-carboxylate

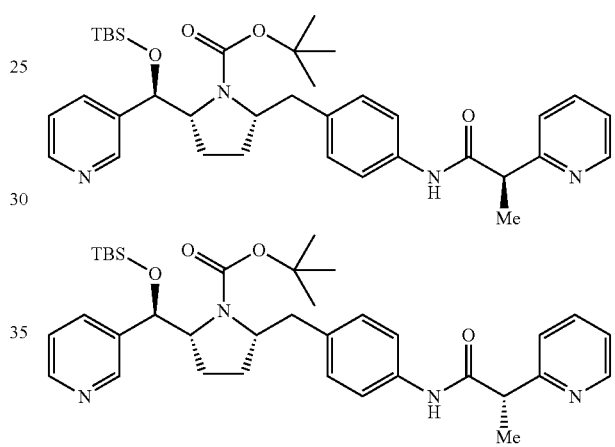

To a solution of 0.060 g (0.12 mmol) of i-4 and 0.022 g (0.14 mmol) of 2-pyridin-2-yl-propanoic acid in 5 mL of anhydrous N,N-dimethylformamide under an atmosphere of nitrogen was added 0.060 mL (0.36 mmol) of diisopropylethylamine, 0.24 mL (0.15 mmol) of a 0.6 M solution of 1-hydroxy-7-azabenzotriazole in N,N-dimethylformamide and 0.028 g (0.15 mmol) of 1-(3-dimethylaminopropyl)-3-ethylcarbodiimide hydrochloride. The resulting suspension was stirred at ambient temperature for 24 h. The crude reaction mixture was quenched with a saturated aqueous sodium bicarbonate solution and then extracted with ethyl acetate (3×10 mL). The combined organic layers were washed with brine, dried over magnesium sulfate, filtered and evaporated in vacuo. The crude residue was purified by silica gel chromatography eluting with 45% ethyl acetate in hexanes to afford the title compound as a mixture of diastereomers as a colorless gum (0.070 g, 92%). The two diastereoisomers were separated by chiral HPLC employing a Daicel CHIRALPAK® AD® column (eluent:15% IPA in Heptane). The first eluting diastereomer was designated as isomer 1 and is a colorless gum: LC-MS: m/z (ES) 631.7 (MH)$^+$. The second eluting diastereomer was designated as isomer 2 and is a colorless foam. LC-MS: m/z (ES) 631.7 (MH)$^+$.

Step B: (2R and 2S)-N-[4-({(2S,5R)-5-[(R)-hydroxy(pyridin-3-yl)methyl]pyrrolidin-2-yl}methyl)phenyl]-2-pyridin-2-ylpropanamide, trifluoroacetic acid salt

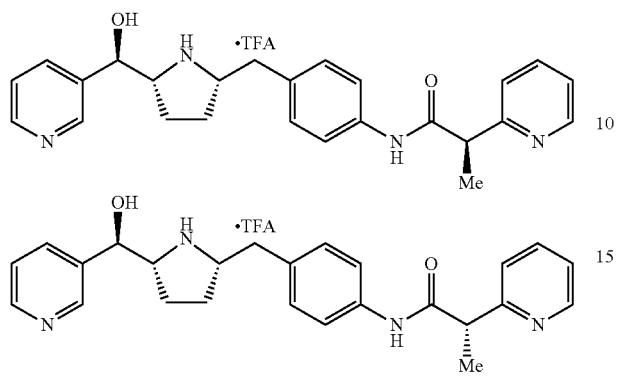

Step B (Isomer 1): (2S)-N-[4-({(2S,5R)-5-[(R)-hydroxy(pyridin-3-yl)methyl]pyrrolidin-2-yl}methyl)phenyl]-2-pyridin-2-ylpropanamide, trifluoroacetic acid salt A solution of 0.030 g (0.047 mmol) of isomer 1 from step A in 2 mL of a 3:3:1 mixture of acetonitrile:trifluoroacetic acid:water was heated to 55° C. for 2 h. The crude reaction mixture was purified by reverse phase HPLC (TMC Pro-Pac C18; 0-50% 0.1% trifluoroacetic acid in acetonitrile/0.1% trifluoroacetic acid in water gradient). The pure fractions were lyophilized overnight to afford a single diastereomer, designated as Example 93, of the title compound as a white solid. LC-MS: m/z (ES) 417.5 (MH)+.

Using the Biological Assays described above, the human Beta-3 agonist functional activity of Example 93 was determined to be less than 100 nM.

Step B (Isomer 2): (2)-N-[4-({(2S,5R)-5-[(R)-hydroxy(pyridin-3-yl)methyl]pyrrolidin-2-yl}methyl)phenyl]-2-pyridin-2-ylpropanamide, trifluoroacetic acid salt The same procedure was employed for the deprotection of isomer 2 from step A to afford a single diastereomer, designated as Example 94, of the title compound as a white solid. LC-MS: m/z (ES) 417.5 (MH)+.

Using the Biological Assays described above, the human Beta-3 agonist functional activity of Example 94 was determined to be less than 100 nM.

EXAMPLES 95 AND 96

(2S)-N-[4-({(2S,5R)-5-[(R)-hydroxy(pyridin-3-yl)methyl]pyrrolidin-2-yl}methyl)phenyl]-2-(2-oxopyridin-1(2H)-yl)propanamide and (2R)—N-[4-({(2S,5R)-5-[(R)-hydroxy(pyridin-3-yl)methyl]pyrrolidin-2-yl}methyl)phenyl]-2-(2-oxopyridin-1(2H)-yl)propanamide, trifluoroacetic acid salt

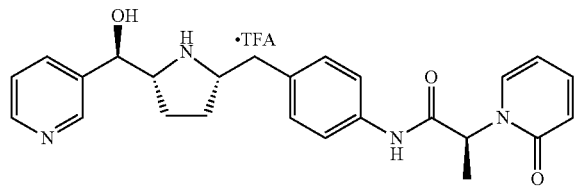

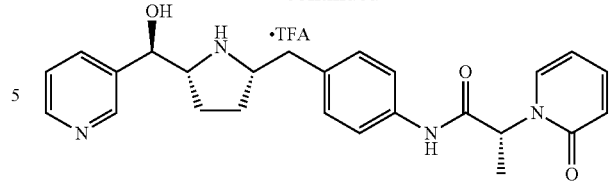

-continued

Step A: Tert-butyl(2R,5S)-2-[(R)-hydroxy(pyridin-3-yl)methyl]-5-(4-{[(2S)-2-(2-oxopyridin-1(2H)-yl)propanoyl]amino}benzyl)pyrrolidine-1-carboxylate and tert-butyl(2R,5S)-2-[(R)-hydroxy(pyridin-3-yl)methyl]-5-(4-{[(2R)-2-(2-oxopyridin-1(2H)-yl)propanoyl]amino}benzyl)pyrrolidine-1-carboxylate

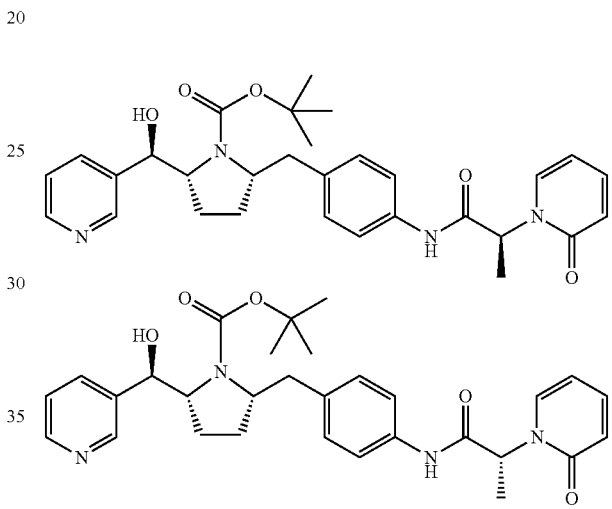

To a solution of 0.050 g (0.13 mmol) of i-17 and 0.039 g (0.23 mmol) of 2-(2-oxopyridin-1(2H)-yl)propanoic acid in 1 mL of anhydrous N,N-dimethylformamide under an atmosphere of nitrogen was added 0.021 mg (0.15 mmol) of 1-hydroxy-7-azabenzotriazole and 0.030 g (0.15 mmol) of 1-(3-dimethylaminopropyl)-3-ethylcarbodiimide hydrochloride. The resulting suspension was stirred at ambient temperature for 24 h. The crude reaction mixture was quenched with a saturated aqueous sodium bicarbonate solution and then extracted with ethyl acetate (3×10 mL). The combined organic layers were washed with brine, dried over magnesium sulfate, filtered and evaporated in vacuo. The crude residue was purified by silica gel chromatography eluting with 80% ethyl acetate in hexanes to afford the title compound as a mixture of diastereomers as a colorless gum. The two diastereoisomers were separated by chiral HPLC employing a Daicel CHIRALCEL® OJ® column (eluent:17% IPA in Heptane). The first eluting diastereomer was designated as isomer 1 and is a colorless gum (22 mg, 39%): LC-MS: m/z (ES) 533.2 (MH)+. The second eluting diastereomer was designated as isomer 2 and is a colorless foam (20 mg, 35%). LC-MS: m/z (ES) 533.2 (MH)+.

Step B: (2R and 2S)-N-[4-({(2S,5R)-5-[(R)-hydroxy(pyridin-3-yl)methyl]pyrrolidin-2-yl}methyl)phenyl]-2-pyridin-2-ylpropanamide, trifluoroacetic acid salt

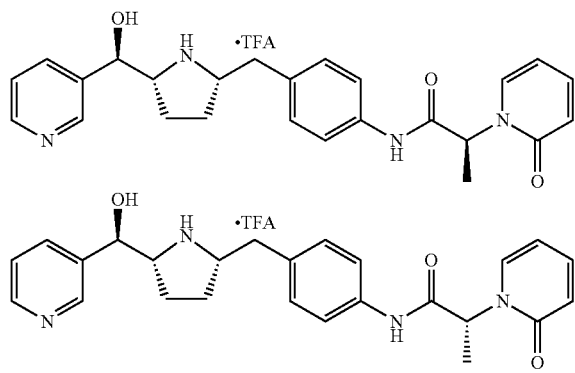

Step B (Isomer 1): (2S)-N-[4-({(2S,5R)-5-[(R)-hydroxy(pyridin-3-yl)methyl]pyrrolidin-2-yl}methyl)phenyl]-2-pyridin-2-ylpropanamide, trifluoroacetic acid salt A solution of 0.022 g (0.041 mmol) of isomer 1 from step A above was dissolved in 2 mL of 4.0 M solution of anhydrous hydrogen chloride in 1,4-dioxane. The reaction mixture was stirred for 1 h and then evaporated to dryness in vacuo. The crude reaction mixture was purified by reverse phase HPLC (TMC Pro-Pac C18; 0-75% 0.1% trifluoroacetic acid in acetonitrile/0.1% trifluoroacetic acid in water gradient) to yield the title compound as a white solid. The pure fractions were lyophilized overnight to afford a single diastereomer, designated as Example 95, of the title compound as a white solid (0.019 g, 85%). $^1$H-NMR (500 MHz, CD$_3$OD) δ 8.74 (s, 1H), 8.63 (d, J=5.0 Hz, 1H), 8.17 (d, J=7.8 Hz, 1H), 7.78 (d, J=6.9 Hz, 1H), 7.69-7.66 (m, 1H), 7.55-7.54 (m, 1H), 7.54 (d, J=8.4 Hz, 2H), 7.24 (d, J=8.4 Hz, 2H), 6.55 (d, J=9.1 Hz, 1H), 6.48-6.44 (m, 1H), 5.57 (q, J=7.3 Hz, 1H), 4.92 (d, J=8.0 Hz, 1H), 3.88-3.82 (m, 1H), 3.78-3.75 (m, 1H), 3.17-3.13 (m, 1H), 2.98-2.94 (m, 1H), 2.20-2.05 (m, 1H), 1.93-1.87 (m, 3H), 1.71 (d, J=7.3 Hz, 3H), LC-MS: m/z (ES) 433.0 (MH)$^+$.

Using the Biological Assays described above, the human Beta-3 agonist functional activity of Example 95 was determined to be less than 10 nM.

Step B (Isomer 2): (2R)—N-[4-({(2S,5R)-5-[(R)-hydroxy(pyridin-3-yl)methyl]pyrrolidin-2-yl}methyl)phenyl]-2-pyridin-2-ylpropanamide, trifluoroacetic acid salt The same procedure was employed for the deprotection of isomer 2 from step A above to afford a single diastereomer, designated as Example 96, of the title compound as a white solid (15 mg, 80%). LC-MS: m/z (ES) 433.0 (MH)$^+$.

Using the Biological Assays described above, the human β3 functional activity of Example 96 was determined to be less than 10 nM.

EXAMPLES 97-221

Following similar procedures outlined in the examples above, the examples in the following table were prepared.

The conditions for the separation of the diastereomers are designated as follows:

Separation Method A: Daicel CHIRALPAK® AD® column eluting with an IPA in Heptane mixture.
Separation Method B: Daicel CHIRALCEL® OD© column eluting with an IPA in Heptane mixture.
Separation Method C: Pirkle (R,R)-Whelk-O® column eluting with an IPA in Heptane mixture.
Separation Method D: Daicel CHIRALCEL® OJ® column eluting with either an IPA in Heptane mixture or EtOH in Hexanes mixture.
Separation Method E: Daicel CHIRALPAK® AS® column eluting with either an IPA in Heptane mixture or EtOH in Hexanes mixture.
Separation Method F: Single enantiomers of the carboxylic acids were used in the preparation of these derivatives.

Using the Biological Assays described above, the human β3 functional activity of each compound was determined and shown in the following table as the following ranges:
less than 1 nM (+);
1-10 nM (++);
11-100 nM (+++);
101-1000 nM (++++); and
greater than 1000 nM but less than 3000 nM (+++++).

TABLE 3

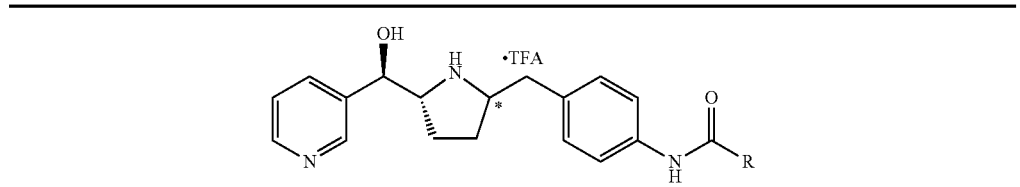

| Example | *Diastereomer | Separation Method | Isomer | R | MW | MS (MH)$^+$ | Human β3 functional |
|---|---|---|---|---|---|---|---|
| 97 | S | A | 1 | 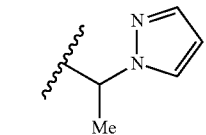 | 405.2 | 406.4 | +++ |

TABLE 3-continued

| Example | *Diastereomer | Separation Method | Isomer | R | MW | MS (MH)+ | Human β3 functional |
|---|---|---|---|---|---|---|---|
| 98 | S | A | 2 | pyrazol-1-yl-CH(Me)- | 405.2 | 406.4 | +++ |
| 99 | S | A | 1 | (3-Me-pyrazol-1-yl)-CH(Me)- | 419.2 | 420.2 | +++ |
| 100 | S | A | 2 | (3-Me-pyrazol-1-yl)-CH(Me)- | 419.2 | 420.2 | +++++ |
| 101 | S | B | 1 | (2-Me-thiazol-4-yl)-CH(Me)- | 436.2 | 437.5 | ++ |
| 102 | S | B | 2 | (2-Me-thiazol-4-yl)-CH(Me)- | 436.2 | 437.5 | ++++ |
| 103 | S | A | 1 | (2,5-diMe-thiazol-4-yl)-CH(Me)- | 450.2 | 451.2 | ++++ |
| 104 | S | A | 2 | (2,5-diMe-thiazol-4-yl)-CH(Me)- | 450.2 | 451.2 | +++++ |
| 105 | S | A | 1 | (2-NH2-thiazol-4-yl)-CH(Me)- | 437.2 | 438.5 | ++ |

TABLE 3-continued
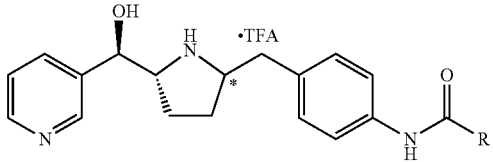
| Example | *Diastereomer | Separation Method | Isomer | R | MW | MS (MH)+ | Human β3 functional |
|---|---|---|---|---|---|---|---|
| 106 | S | A | 2 | 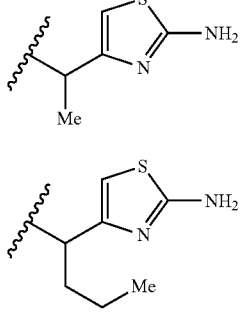 | 437.2 | 438.5 | ++ |
| 107 | S | A | 1 | 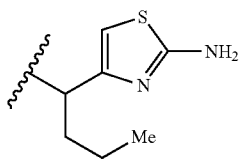 [SMILES: *C(CCC)c1csc(N)n1] | 465.2 | 466.3 | +++ |
| 108 | S | A | 2 | 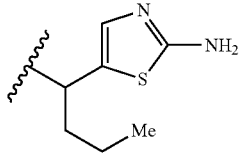 [SMILES: *C(CCC)c1cnc(N)s1] | 465.2 | 466.4 | ++ |
| 109 | S | None | 1 and 2 | 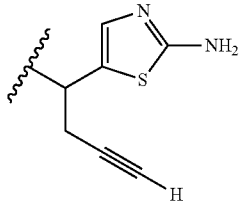 [SMILES: *C(CC#C)c1cnc(N)s1] | 465.2 | 466.5 | ++ |
| 110 | S | None | 1 and 2 | 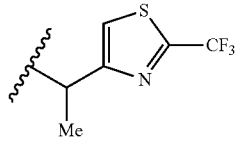 [SMILES: *C(C)c1csc(C(F)(F)F)n1] | 461.2 | 462.5 | ++ |
| 111 | S | C | 1 | 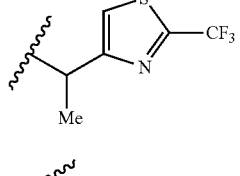 | 490.2 | 491 | +++ |
| 112 | S | C | 2 | 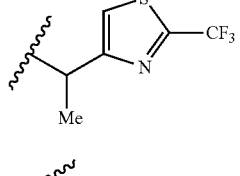 | 490.2 | 491 | ++++ |
| 113 | S | C | 1 | 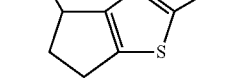 | 449.2 | 450 | + |

TABLE 3-continued
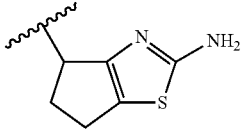 [SMILES: *C1CCc2sc(N)nc21]
| Example | *Diastereomer | Separation Method | Isomer | R | MW | MS (MH)+ | Human β3 functional |
|---|---|---|---|---|---|---|---|
| 114 | S | C | 2 | 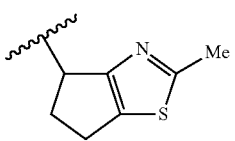 [SMILES: *C1CCc2sc(C)nc21] | 449.2 | 450 | +++ |
| 115 | S | C | 1 | 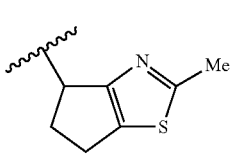 [SMILES: *C1CCc2sc(C)nc21] | 448.2 | 449 | ++ |
| 116 | S | C | 2 | 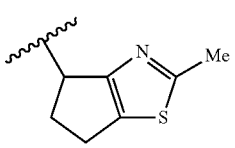 | 448.2 | 449 | ++++ |
| 117 | R | C | 1 | 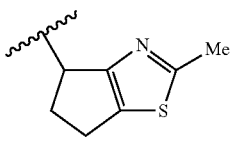 [SMILES: *C1CCc2sc(C)nc21] | 448.2 | 449 | +++ |
| 118 | R | C | 2 | 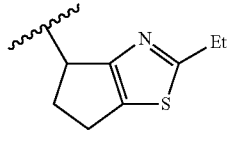 | 448.2 | 449 | ++++ |
| 119 | S | C | 1 | 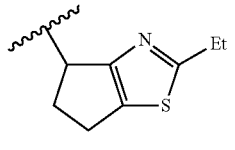 [SMILES: *C1CCc2sc(CC)nc21] | 462.2 | 463 | ++++ |
| 120 | S | C | 2 | 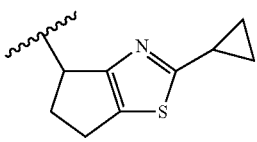 [SMILES: *C1CCc2sc(C3CC3)nc21] | 462.2 | 463 | +++ |
| 121 | S | C | 1 | 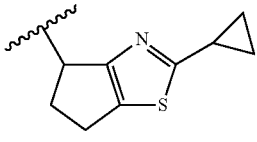 [SMILES: *C1CCc2sc(C3CC3)nc21] | 474.2 | 475 | +++ |
| 122 | S | C | 2 |  | 474.2 | 475 | ++++ |

TABLE 3-continued

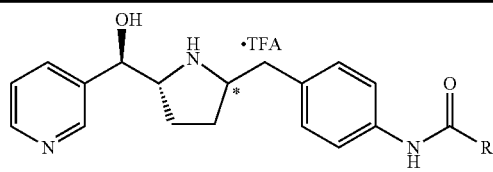

| Example | *Diastereomer | Separation Method | Isomer | R | MW | MS (MH)+ | Human β3 functional |
|---|---|---|---|---|---|---|---|
| 123 | S | C | 1 | (2-isopropyl-cyclopenta-thiazole) | 476.2 | 477 | ++++ |
| 124 | S | C | 2 | (2-isopropyl-cyclopenta-thiazole) | 476.2 | 477 | +++ |
| 125 | S | C | 1 | (2-methoxymethyl-cyclopenta-thiazole) | 478.2 | 479 | +++ |
| 126 | S | C | 2 | (2-methoxymethyl-cyclopenta-thiazole) | 428.2 | 479 | ++++ |
| 127 | S | A | 1 | (cyclopenta-pyridine) | 428.2 | 429.4 | ++ |
| 128 | S | A | 2 | (cyclopenta-pyridine) | 462.2 | 429.2 | ++ |
| 129 | S | C | 1 | (2,4-dimethyl-4-Me-cyclopenta-thiazole) | 462.2 | 463 | +++++ |
| 130 | S | C | 2 | (2,4-dimethyl-4-Me-cyclopenta-thiazole) | 462.2 | 463 | ++++ |
| 131 | S | C | 1 | (2-methyl-tetrahydrobenzo-thiazole) | 462.2 | 463 | ++ |

US 8,501,786 B2
TABLE 3-continued
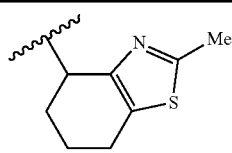
| Example | *Diastereomer | Separation Method | Isomer | R | MW | MS (MH)+ | Human β3 functional |
|---|---|---|---|---|---|---|---|
| 132 | S | C | 2 | 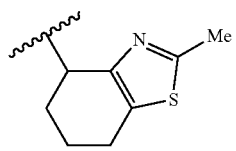 [SMILES: *C1CCCc2sc(C)nc21] | 462.2 | 463 | ++++ |
| 133 | R | C | 1 | 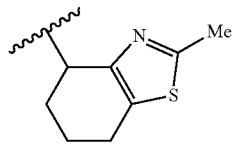 [SMILES: *C1CCCc2sc(C)nc21] | 462.2 | 463 | +++ |
| 134 | R | C | 2 | 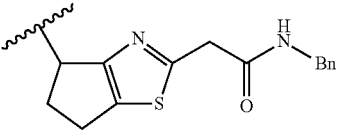 [SMILES: *C1CCc2sc(CC(=O)NCc3ccccc3)nc21] | 462.2 | 463 | +++ |
| 135 | S | C | 1 | 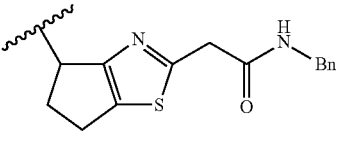 [SMILES: *C1CCc2sc(CC(=O)NCc3ccccc3)nc21] | 581 | 582 | +++ |
| 136 | S | C | 2 | 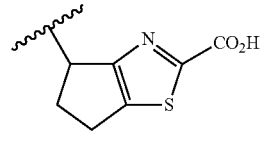 [SMILES: *C1CCc2sc(C(=O)O)nc21] | 581 | 582 | ++ |
| 137 | S | C | 1 | 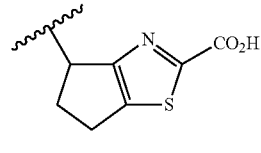 [SMILES: *C1CCc2sc(C(=O)O)nc21] | 478 | 479 | ++ |
| 138 | S | C: | 2 | 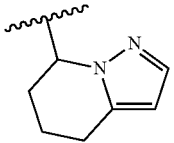 [SMILES: *C1CCCc2ccnn21] | 478 | 479 | +++ |
| 139 | S | A | 1 | 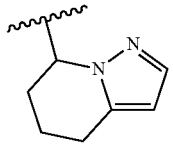 [SMILES: *C1CCCc2ccnn21] | 431 | 432 | ++++ |
| 140 | S | A | 2 | 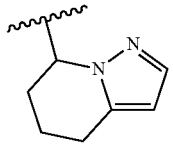 [SMILES: *C1CCCc2ccnn21] | 431 | 432 | +++ |

TABLE 3-continued
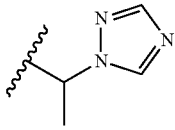 [SMILES: *C(C)n1cncn1]
| Example | *Diastereomer | Separation Method | Isomer | R | MW | MS (MH)+ | Human β3 functional |
|---|---|---|---|---|---|---|---|
| 141 | S | A | 1 | 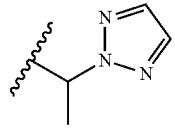 [SMILES: *C(C)n1nccn1] | 406 | 407 | ++ |
| 142 | S | A | 1 | 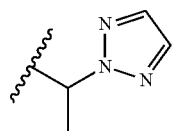 [SMILES: *C(C)n1nccn1] | 406 | 407 | ++ |
| 143 | S | A | 2 | 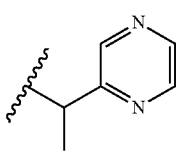 [SMILES: *C(C)c1cnccn1] | 406 | 407 | ++ |
| 144 | S | A | 1 | 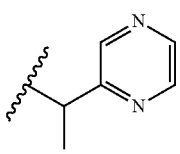 [SMILES: *C(C)c1cnccn1] | 417.5 | 418.0 | ++ |
| 145 | S | A | 2 | 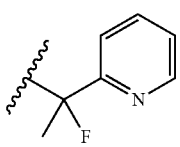 [SMILES: *C(C)(F)c1ccccn1] | 417.5 | 418.0 | ++ |
| 146 | S | A | 1 | 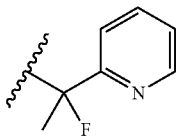 [SMILES: *C(C)(F)c1ccccn1] | 434.5 | 435.0 | +++ |
| 147 | S | A | 2 | 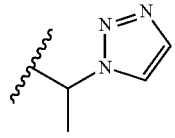 [SMILES: *C(C)n1ccnn1] | 434.5 | 435.0 | ++++ |
| 148 | S | A | 1 | 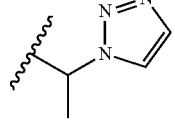 | 406 | 407 | ++ |
| 149 | S | A | 2 | 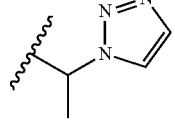 | 406 | 407 | ++ |

TABLE 3-continued
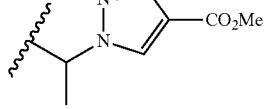
| Example | *Diastereomer | Separation Method | Isomer | R | MW | MS (MH)+ | Human β3 functional |
|---|---|---|---|---|---|---|---|
| 150 | S | A | 1 | 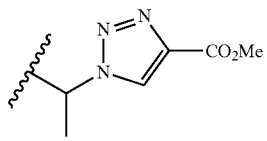 [SMILES: *C(C)n1cc(C(=O)OC)nn1] | 464 | 465 | ++ |
| 151 | S | A | 2 | 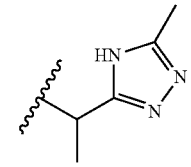 | 464 | 465 | +++ |
| 152 | S | C | 1 | 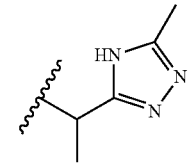 [SMILES: *C(C)c1nnc(C)[nH]1] | 420 | 421 | ++ |
| 153 | S | C | 2 | 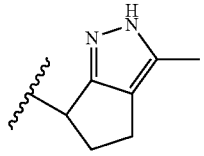 [SMILES: *C1CCc2c1n[nH]c2C] | 420 | 421 | +++ |
| 154 | S | C | 1 | 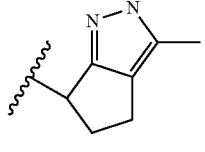 | 431 | 432 | ++ |
| 155 | S | C | 2 | 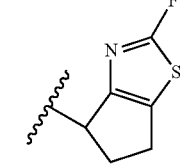 | 431 | 432 | +++ |
| 156 | S | C | 1 | 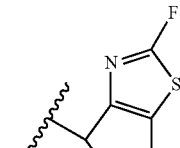 | 452 | 453 | ++ |
| 157 | S | C | 2 | | 452 | 453 | ++ |

TABLE 3-continued

| Example | *Diastereomer | Separation Method | Isomer | R | MW | MS (MH)+ | Human β3 functional |
|---|---|---|---|---|---|---|---|
| 158 | S | C | 1 | 2-bromo-5,6-dihydro-4H-cyclopenta[d]thiazol-5-yl | 513 | 513 (M)+<br>515 (M + 2)+ | + |
| 159 | S | C | 2 | 2-bromo-5,6-dihydro-4H-cyclopenta[d]thiazol-5-yl | 513 | 513 (M)+<br>515 (M + 2)+ | +++ |
| 160 | S | D | 1 | 4-oxo-6,7-dihydro-4H-pyrrolo[1,2-a]pyrimidin-6-yl | 445 | 446 | ++ |
| 161 | S | D | 2 | 4-oxo-6,7-dihydro-4H-pyrrolo[1,2-a]pyrimidin-6-yl | 445 | 446 | ++ |
| 162 | S | D | 1 | 1-(6-oxopyridazin-1(6H)-yl)ethyl | 433 | 434 | ++ |
| 163 | S | D | 2 | 1-(6-oxopyridazin-1(6H)-yl)ethyl | 433 | 4346 | ++ |
| 164 | S | E | 1 | 1-(6-oxopyrimidin-1(6H)-yl)ethyl | 433 | 434 | ++ |
| 165 | S | E | 2 | 1-(6-oxopyrimidin-1(6H)-yl)ethyl | 433 | 434 | ++ |

TABLE 3-continued

| Example | *Diastereomer | Separation Method | Isomer | R | MW | MS (MH)+ | Human β3 functional |
|---|---|---|---|---|---|---|---|
| 166 | S | F | 1 | (1-methyl-2-oxo-pyrimidin-1-yl)ethyl | 433 | 434 | ++ |
| 167 | S | F | 2 | (1-methyl-2-oxo-pyrimidin-1-yl)ethyl | 433 | 4346 | ++ |
| 168 | S | B | 1 | 3-methyl-cyclopenta[d]isoxazol-6-yl | 432 | 433 | ++ |
| 169 | S | B | 2 | 3-methyl-cyclopenta[d]isoxazol-6-yl | 432 | 433 | +++ |
| 170 | S | E | 1 | 3-methyl-pyrrolo[2,1-c][1,2,4]triazol-7-yl | 432 | 433 | +++ |
| 171 | S | E | 2 | 3-methyl-pyrrolo[2,1-c][1,2,4]triazol-7-yl | 432 | 433 | +++ |
| 172 | S | F | n/a | pyrrolo-tetrazolyl | 419 | 420 | ++ |
| 173 | S | F | n/a | pyrrolo-tetrazolyl | 419 | 420 | ++ |

TABLE 3-continued

| Example | *Diastereomer | Separation Method | Isomer | R | MW | MS (MH)+ | Human β3 functional |
|---|---|---|---|---|---|---|---|
| 174 | S | B | 1 | thiadiazole-CH(CH3)- | 422 | 423 | ++ |
| 175 | S | B | 2 | thiadiazole-CH(CH3)- | 422 | 423 | ++ |
| 176 | S | C | 1 | 3-methylpyrazole-CH(CH3)- | 419 | 420 | +++ |
| 177 | S | C | 2 | 3-methylpyrazole-CH(CH3)- | 419 | 420 | ++++ |
| 178 | S | C | 1 | pyrazole-CH(CH3)- | 405 | 406 | ++ |
| 179 | S | C | 2 | pyrazole-CH(CH3)- | 405 | 406 | +++ |
| 180 | S | B | 1 | N-methyltetrazole-CH(CH3)- | 421 | 422 | +++ |
| 181 | S | B | 2 | N-methyltetrazole-CH(CH3)- | 421 | 422 | +++ |
| 182 | S | B | 1 | tetrazole-CH(CH3)- | 407 | 408 | +++ |

TABLE 3-continued
| Example | *Diastereomer | Separation Method | Isomer | R | MW | MS (MH)+ | Human β3 functional |
|---|---|---|---|---|---|---|---|
| 183 | S | B | 2 | 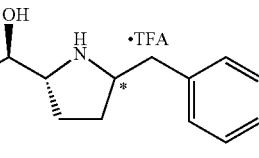 | 407 | 408 | ++ |
| 184 | S | A | 1 | 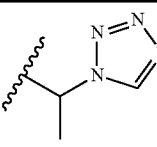 | 419 | 420 | ++ |
| 185 | S | A | 2 | 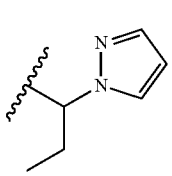 [SMILES: *C(CC)n1cccn1] | 419 | 420 | ++ |
| 186 | S | C | 1 | 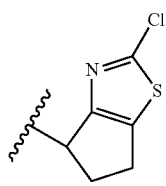 [SMILES: *C1CCc2sc(Cl)nc21] | 468 | 469 | + |
| 187 | S | C | 2 | 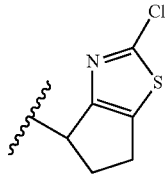 [SMILES: *C1CCc2sc(Cl)nc21] | 468 | 469 | +++ |
| 188 | S | C | 1 | 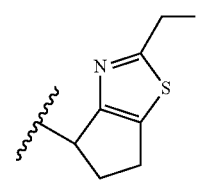 | 464 | 465 | ++ |
| 189 | S | C | 2 | 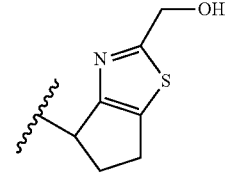 [SMILES: *C1CCc2sc(CO)nc21] | 464 | 465 | +++ |
| 190 | S | C | 1 | 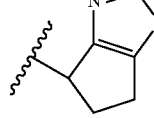 | 434 | 435 | + |

TABLE 3-continued

| Example | *Diastereomer | Separation Method | Isomer | R | MW | MS (MH)+ | Human β3 functional |
|---|---|---|---|---|---|---|---|
| 191 | S | C | 2 | (thiazole-fused cyclopentane) | 434 | 435 | +++ |
| 192 | S | B | 1 | (pyrrolo-quinazolinone) | 495 | 496 | +++ |
| 193 | S | B | 2 | (pyrrolo-quinazolinone) | 495 | 496 | ++ |
| 194 | S | F | 1 | (pyrrolo-triazole) | 418 | 419 | +++ |
| 195 | S | C | 1 | (thiazole with Me) | 422 | 423 | + |
| 196 | S | C | 2 | (thiazole with Me) | 422 | 423 | +++ |
| 197 | S | F | 1 | (pyrrolidinone) | 394 | 395 | ++++ |
| 198 | S | A | 1 | (triazole carboxylic acid with Me) | 450 | 451 | +++ |

TABLE 3-continued
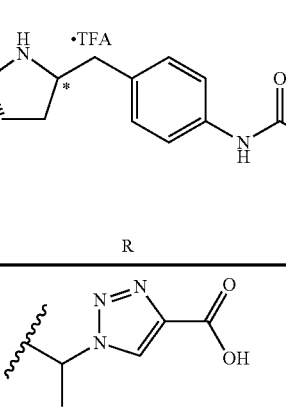
| Example | *Diastereomer | Separation Method | Isomer | R | MW | MS (MH)+ | Human β3 functional |
|---|---|---|---|---|---|---|---|
| 199 | S | A | 2 | 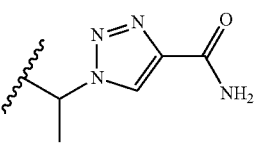 [SMILES: *C(C)n1cc(C(N)=O)nn1] | 450 | 451 | +++ |
| 200 | S | A | 1 | 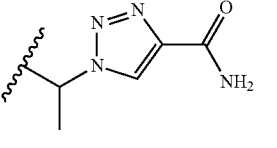 [SMILES: *C(C)n1cc(C(N)=O)nn1] | 449 | 450 | +++ |
| 201 | S | A | 2 | 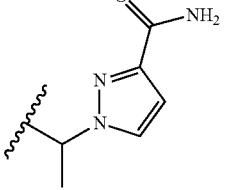 | 449 | 450 | ++ |
| 202 | S | A | 1 | 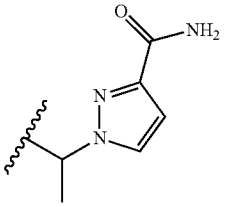 [SMILES: *C(C)n1ccc(C(N)=O)n1] | 448 | 449 | ++ |
| 203 | S | A | 2 | 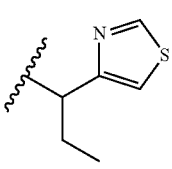 [SMILES: *C(CC)c1cscn1] | 448 | 449 | ++++ |
| 204 | S | C | 1 | 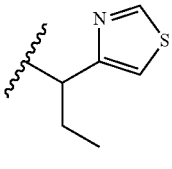 [SMILES: *C(CC)c1cscn1] | 436 | 437 | ++ |
| 205 | S | C | 2 | 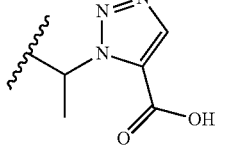 | 436 | 437 | +++ |
| 206 | S | C | 1 |  | 450 | 451 | ++ |

TABLE 3-continued
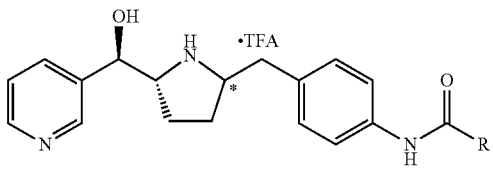
| Example | *Diastereomer | Separation Method | Isomer | R | MW | MS (MH)+ | Human β3 functional |
|---|---|---|---|---|---|---|---|
| 207 | S | C | 2 | 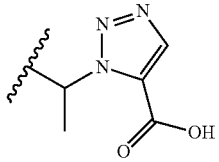 [SMILES: *C(C)n1nncc1C(=O)O] | 450 | 451 | +++ |
| 208 | S | C | 1 | 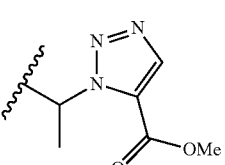 | 464 | 465 | ++ |
| 209 | S | C | 2 | 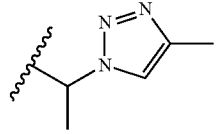 | 464 | 465 | ++++ |
| 210 | S | B | 1 | 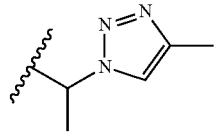 | 420 | 421 | +++ |
| 211 | S | B | 2 | 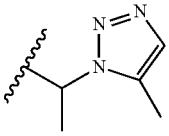 [SMILES: *C(C)n1nncc1C] | 420 | 421 | +++ |
| 212 | S | C | 1 | 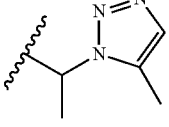 | 420 | 421 | ++++ |
| 213 | S | C | 2 | 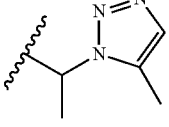 | 420 | 421 | ++ |
| 214 | S | C | 1 | 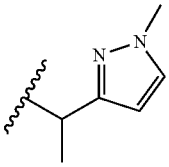 [SMILES: *C(C)c1ccn(C)n1] | 419 | 420 | +++ |

TABLE 3-continued

| Example | *Diastereomer | Separation Method | Isomer | R | MW | MS (MH)+ | Human β3 functional |
|---|---|---|---|---|---|---|---|
| 215 | S | C | 2 | (1-methylpyrazol-3-yl)ethyl | 419 | 420 | ++++ |
| 216 | S | A | 1 | (3-methyl-[1,2,4]triazolo[4,3-a]pyridin-8-yl)ethyl | 470 | 471 | +++ |
| 217 | S | A | 2 | (3-methyl-[1,2,4]triazolo[4,3-a]pyridin-8-yl)ethyl | 470 | 471 | +++ |
| 218 | S | None | 1 and 2 | (4-oxoquinazolin-3-yl)isopropyl | 483 | 484 | ++ |
| 219 | S | A | 1 | 1-(4-carbamoylpyrazol-1-yl)ethyl | 448 | 449 | ++ |
| 220 | S | C | 1 | 1-(pyrazol-1-yl)-3-methoxypropyl | 449 | 450 | ++ |
| 221 | S | C | 2 | 1-(pyrazol-1-yl)-3-methoxypropyl | 449 | 450 | ++ |

EXAMPLE 222

N-[4-({(2S,5R)-5-[(R)-hydroxy(pyridin-3-yl)methyl]pyrrolidin-2-yl}methyl)phenyl]-4-{4-[4-(trifluoromethyl)phenyl]-1,3-thiazol-2-yl}benzenesulfonamide, trifluoroacetic acid salt

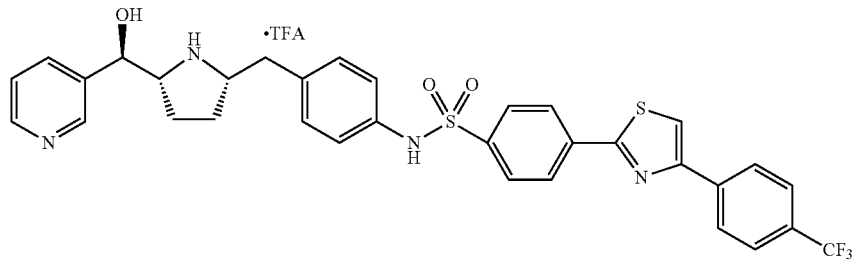 [SMILES: O=S(=O)(Nc1ccc(C[C@@H]2CC[C@H]([C@H](O)c3cccnc3)N2)cc1)c1ccc(-c2nc(-c3ccc(C(F)(F)F)cc3)cs2)cc1]

Step A: Tert-butyl(2R,5S)-2-[(R)-{[tert-butyl(dimethyl)silyl]oxy}(pyridin-3-yl)methyl]-5-(4-{[(4-{4-[4-(trifluoromethyl)phenyl]-1,3-thiazol-2-yl}phenyl)sulfonyl]amino}benzyl)pyrrolidine-1-carboxylate, trifluoroacetic acid salt

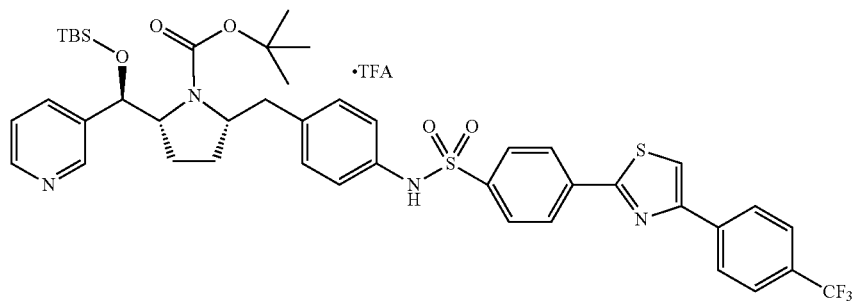

To a solution of 0.030 g (0.060 mmol) of i-4 in 1 mL of anhydrous N,N-dimethylacetamide under an atmosphere of nitrogen was added 0.012 mL (0.072 mmol) of N,N-diisopropylethylamine followed by 0.030 g (0.072 mmol) of i-16. The resulting suspension was stirred at ambient temperature for 24 h. The crude reaction mixture was purified by reverse phase HPLC (TMC Pro-Pac C18; 10-100% 0.1% trifluoroacetic acid in acetonitrile/0.1% trifluoroacetic acid in water gradient) to afford the title compound as a colorless solid. LC-MS: m/z (ES) 865.2 (MH)$^+$.

Step B: N-[4-({(2S,5R)-5-[(R)-hydroxy(pyridin-3-yl)methyl]pyrrolidin-2-yl}methyl)phenyl]-4-{4-[4-(trifluoromethyl)phenyl]-1,3-thiazol-2-yl}benzenesulfonamide, trifluoroacetic acid salt

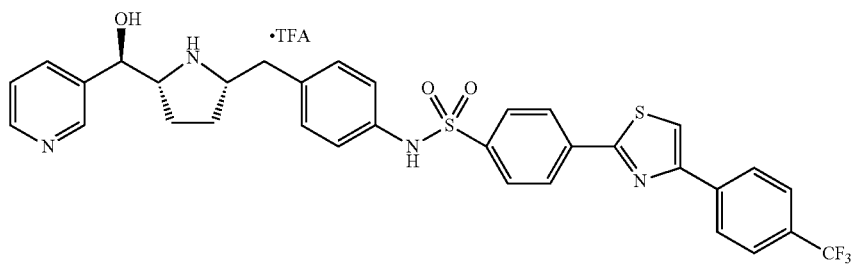 [SMILES: O=S(=O)(Nc1ccc(C[C@@H]2CC[C@H]([C@H](O)c3cccnc3)N2)cc1)c1ccc(-c2nc(-c3ccc(C(F)(F)F)cc3)cs2)cc1]

A solution of 0.050 g (0.051 mmol) of tert-butyl(2R,5S)-2-[(R)-{[tert-butyl(dimethyl)silyl]oxy}(pyridin-3-yl)methyl]-5-(4-{[(4-{4-[4-(trifluoromethyl)phenyl]-1,3-thiazol-2-yl}phenyl)sulfonyl]amino}benzyl)pyrrolidine-1-carboxylate, trifluoroacetic acid salt from step A in 2 mL of a 3:3:1 mixture of acetonitrile:trifluoroacetic acid:water was heated to 55° C. for 2 h. The crude reaction mixture was purified by reverse phase HPLC (TMC Pro-Pac C18; 10-100% 0.1% trifluoroacetic acid in acetonitrile/0.1% trifluoroacetic acid in water gradient). The pure fractions were lyophilized overnight to afford the title compound as a white solid. LC-MS: m/z (ES) 651.5 (MH)$^+$.

Using the Biological Assays described above, the human β3 functional activity of Example 222 was determined to be less than 10 nM.

EXAMPLES 223-238

Following similar procedures outlined in Example 222 above, the examples in the following table were prepared.

Using the Biological Assays described above, the human β3 functional activity of each compound was determined and shown in the following table as the following ranges:

1-10 nM (++);

11-100 nM (+++); and 101-1000 nM (++++).

TABLE 4

| Example | *Diastereomer | R | MW | MS (MH)$^+$ | Human β3 functional |
|---|---|---|---|---|---|
| 223 | R | 4-phenyl-2-[4-(trifluoromethyl)phenyl]-1,3-thiazol-2-yl | 650.2 | 651.4 | ++ |
| 224 | S | 4-iodophenyl | 549.1 | 550.0 | +++ |
| 225 | S | naphthalen-2-yl | 473.2 | 474.4 | +++ |
| 226 | S | (pyridin-2-yl)methyl | 438.2 | 439.1 | ++++ |
| 227 | S | 4-(1H-pyrazol-1-yl)phenyl | 489.2 | 490.1 | +++ |
| 228 | S | isoquinolin-6-yl | 474.2 | 475.2 | ++++ |

TABLE 4-continued
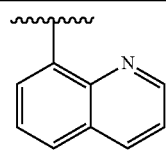
| Example | *Diastereomer | R | MW | MS (MH)+ | Human β3 functional |
|---|---|---|---|---|---|
| 229 | S | 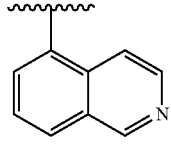 [SMILES: *c1cccc2cnccc12] | 474.2 | 475.4 | ++++ |
| 230 | S | 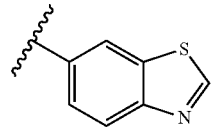 [SMILES: *c1ccc2ncsc2c1] | 474.2 | 475.4 | ++++ |
| 231 | S | 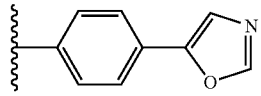 [SMILES: *c1ccc(-c2cnco2)cc1] | 480.1 | 481.3 | ++++ |
| 232 | S | 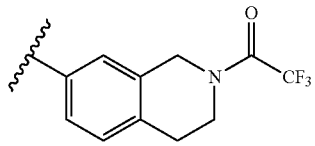 [SMILES: *c1ccc2c(c1)CN(C(=O)C(F)(F)F)CC2] | 490.1 | 491.4 | +++ |
| 233 | S | 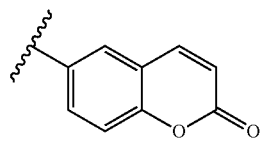 [SMILES: *c1ccc2oc(=O)ccc2c1] | 574.2 | 575.2 | ++++ |
| 234 | S | 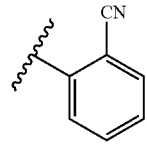 [SMILES: *c1ccccc1C#N] | 491.1 | 492.0 | ++++ |
| 235 | S | 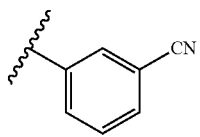 [SMILES: *c1cccc(C#N)c1] | 448.2 | 449.1 | ++++ |
| 236 | S | 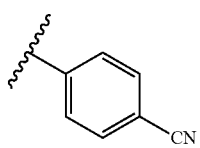 [SMILES: *c1ccc(C#N)cc1] | 448.2 | 449.1 | ++++ |
| 237 | S | | 448.2 | 449.3 | ++++ |

TABLE 4-continued

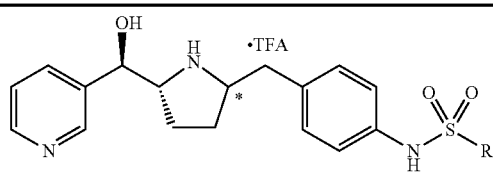

| Example | *Diastereomer | R | MW | MS (MH)+ | Human β3 functional |
|---|---|---|---|---|---|
| 238 | S | (2-iodophenyl) | 549.0 | 550.0 | ++++ |

EXAMPLE 239

4-{[(Hexylamino)carbonyl]amino}-N-[4-({(2S,5R)-5-[(R)-hydroxy(pyridin-3-yl)methyl]pyrrolidin-2-yl}methyl)phenyl]benzenesulfonamide, trifluoroacetic acid salt

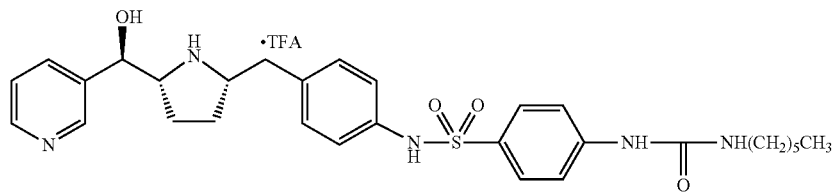

Step A: Tert-butyl(2R,5S)-2-[(R)-{[tert-butyl(dimethyl)silyl]oxy}(pyridin-3-yl)methyl]-5-(4-{[(4-{[(hexylamino)carbonyl]amino}phenyl)sulfonyl]amino}benzyl)pyrrolidine-1-carboxylate, trifluoroacetic acid salt

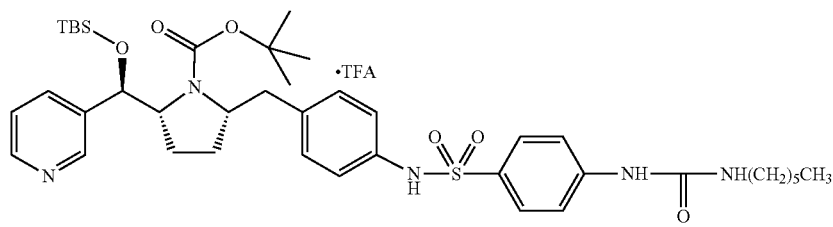

To a stirred solution of 0.057 g (0.24 mmol) of 4-cyanobenzenesulfonyl chloride in 5 mL of dichloromethane cooled to −78° C. under a nitrogen atmosphere was added 0.024 g (0.24 mmol) of n-hexylamine and the resulting solution was stirred for 30 min. This was then added via cannula to a stirred solution of 0.030 g (0.060 mmol) of i-4 and 0.084 mL (0.60 mmol) and triethyamine at ambient temperature. The resulting solution was stirred for 2 h, evaporated to dryness and purified by reverse phase HPLC (TMC Pro-Pac C18; 10-100% 0.1% trifluoroacetic acid in acetonitrile/0.1% trifluoroacetic acid in water gradient) to give the title compound as a colorless solid. LC-MS: m/z (ES) 780.2 (MH)+.

Step B: 4-{[(hexylamino)carbonyl]amino}-N-[4-({(2S,5R)-5-[(R)-hydroxy(pyridin-3-yl)methyl]pyrrolidin-2-yl}methyl)phenyl]benzenesulfonamide, trifluoroacetic acid salt

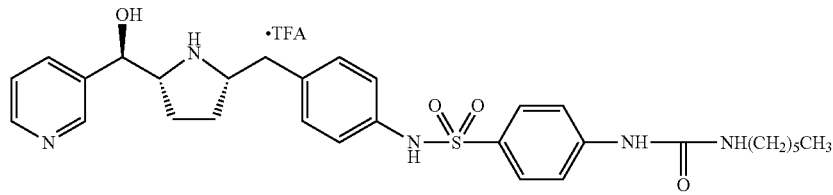

A solution of 0.020 g (0.022 mmol) of tert-butyl(2R,5S)-2-[(R)-{[tert-butyl(dimethyl)silyl]oxy}(pyridin-3-yl)methyl]-5-(4-{[(4-{[(hexylamino)carbonyl]amino}phenyl)sulfonyl]amino}benzyl)pyrrolidine-1-carboxylate, trifluoroacetic acid salt from Step A in 2 mL of a 3:3:1 mixture of acetonitrile:trifluoroacetic acid:water was heated to 55° C. for 2 h. The crude reaction mixture was purified by reverse phase HPLC (TMC Pro-Pac C 18; 10-100% 0.1% trifluoroacetic acid in acetonitrile/0.1% trifluoroacetic acid in water gradient). The pure fractions were lyophilized overnight to give the title compound as a white solid. LC-MS: m/z (ES) 566.3 (MH)$^+$.

Using the Biological Assays described above, the human β3 functional activity of Example 239 was determined to be less than 10 nM.

EXAMPLES 240 AND 241

(4S)-2-bromo-N-[2-bromo-4-({(2S,5R)-5-[(R)-hydroxy(pyridin-3-yl)methyl]pyrrolidin-2-yl}methyl)phenyl]-5,6-dihydro-4H-cyclopenta[d][1,3]thiazole-4-carboxamide and (4R)-2-bromo-N-[2-bromo-4-({(2S,5R)-5-[(R)-hydroxy(pyridin-3-yl)methyl]pyrrolidin-2-yl}methyl)phenyl]-5,6-dihydro-4H-cyclopenta[d][1,3]thiazole-4-carboxamide, trifluoroacetic acid salt

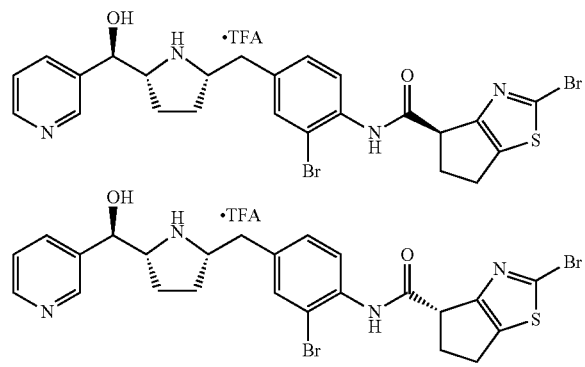

Step A: Tert-butyl(2S,5R)-2-[3-bromo-4-({[(4R)-2-bromo-5,6-dihydro-4H-cyclopenta[d][1,3]thiazol-4-yl]carbonyl}amino)benzyl]-5-[(R)-hydroxy(pyridin-3-yl)methyl]pyrrolidine-1-carboxylate and tert-butyl (2S,5R)-2-[3-bromo-4-({[(4S)-2-bromo-5,6-dihydro-4H-cyclopenta[d][1,3]thiazol-4-yl]carbonyl}amino)benzyl]-5-[(R)-hydroxy(pyridin-3-yl)methyl]pyrrolidine-1-carboxylate

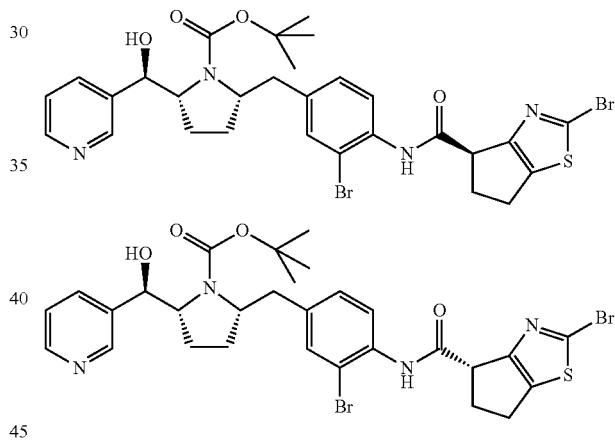

To a solution of 0.069 g (0.15 mmol) of i-49 and 0.041 g (0.17 mmol) of i-28 in 1 mL of anhydrous N,N-dimethylformamide under an atmosphere of nitrogen was added 0.031 g (0.22 mmol) of 1-hydroxy-7-azabenzotriazole and 0.057 g (0.30 mmol) of 1-(3-dimethylaminopropyl)-3-ethylcarbodiimide hydrochloride. The resulting suspension was stirred at ambient temperature for 24 h. The crude reaction mixture was purified by silica gel chromatography eluting with a 0-100% ethyl acetate in hexanes gradient to afford the title compounds as a mixture of diastereomers as a colorless gum. The two diastereoisomers were separated by chiral HPLC employing a Daicel CHIRALCEL® OD® column (eluent:17-45% IPA in Heptane). The first eluting diastereomer was designated as isomer 1 and is a colorless solid (0.019 g, 18%): LC-MS: m/z (ES) 533.2 (MH)$^+$. The second eluting diastereomer was designated as isomer 2 and is a colorless solid (0.019 g, 18%). LC-MS: m/z (ES) 693 (MH)$^+$.

Step B: (4S and 4R)-2-bromo-N-[2-bromo-4-({(2S, 5R)-5-[(R)-hydroxy(pyridin-3-yl)methyl]pyrrolidin-2-yl}methyl)phenyl]-5,6-dihydro-4H-cyclopenta[d][1,3]thiazole-4-carboxamide

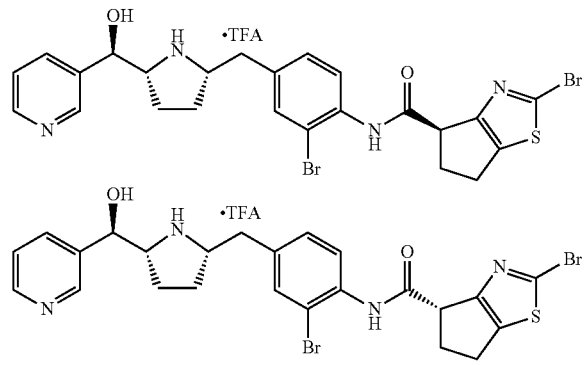

Step B (Isomer 1): (4S or 4R)-2-bromo-N-[2-bromo-4-({(2S,5R)-5-[(R)-hydroxy(pyridin-3-yl)methyl]pyrrolidin-2-yl}methyl)phenyl]-5,6-dihydro-4H-cyclopenta[d][1,3]thiazole-4-carboxamide To a solution of 0.019 g (0.027 mmol) of isomer 1 from step A above dissolved in 1 mL of anhydrous dichloromethane was added 0.15 mL of TFA. The resulting mixture was stirred at ambient temperature for 2 h and then evaporated to dryness in vacuo. The crude reaction mixture was purified by reverse phase HPLC (TMC Pro-Pac C18; 0-60% 0.1% trifluoroacetic acid in acetonitrile/0.1% trifluoroacetic acid in water gradient) to yield the title compound as a white solid. The pure fractions were lyophilized overnight to afford a single diastereomer, designated as Example 240, of the title compound as a white solid (0.019 g, 95%). LC-MS: m/z (ES) 593 (MH)+.

Using the Biological Assays described above, the human β3 functional activity of Example 240 was determined to be less than 1000 nM.

Step B (Isomer 2): (4S or 4R)-2-bromo-N-[2-bromo-4-({(2S,5R)-5-[(R)-hydroxy(pyridin-3-yl)methyl]pyrrolidin-2-yl}methyl)phenyl]-5,6-dihydro-4H-cyclopenta[d][1,3]thiazole-4-carboxamide The same procedure was employed for the deprotection of isomer 2 from step A above to afford a single diastereomer of the title compound, designated as Example 241, as a white solid. LC-MS: m/z (ES) 593 (MH)+.

Using the Biological Assays described above, the human β3 functional activity of Example 241 was determined to be less than 100 nM.

EXAMPLES 242-244

Following similar procedures outlined above, the examples in the following table were prepared. When necessary, the conditions for the separation of the diastereomers are designated as follows:

Separation Method B: Daicel CHIRALCEL® OD® column eluting with an IPA in Heptane mixture.

Using the Biological Assays described above, the human β3 functional activity of each compound was determined and shown in the following table as the following ranges:
11-100 nM (+++); and
101-1000 nM (++++).

TABLE 5

| Example | *Diastereomer | Separation Method | R | MW | MS (MH)+ | Human β3 functional |
|---|---|---|---|---|---|---|
| 242 | S | None | ![thiazole-NH2] | 501, 503 | 502, 504 | ++++ |
| 243 | S | B | ![iodo-cyclopenta-thiazole] Isomer 1 | 638, 640 | 639, 641 | ++++ |

TABLE 5-continued

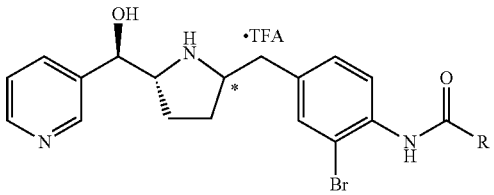

| Example | *Diastereomer | Separation Method | R | MW | MS (MH)+ | Human β3 functional |
|---|---|---|---|---|---|---|
| 244 | S | B | 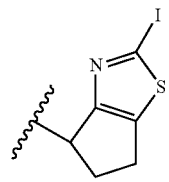<br>Isomer 2 | 638, 640 | 639, 641 | +++ |

EXAMPLE 245

2-Fluoro-N-((1S)-2-{[4-({(2S,5R)-5-[(R)-hydroxy(pyridin-3-yl)methyl]pyrrolidin-2-yl}methyl)phenyl]amino}-1-2-oxoethyl)benzamide

Step A: Tert-butyl(2S,5R)-2-[4-({(2S)-2-[(2-fluorobenzoyl)amino]propanoyl}amino)benzyl]-5-[(R)-hydroxy(pyridin-3-yl)methyl]pyrrolidine-1-carboxylate, trifluoroacetic acid salt To a solution of 0.090 g (0.20 mmol) of i-72 in 2 mL of dichloromethane was added 0.027 mL (0.20 mmol) of triethylamine followed by 0.032 g (0.20 mmol) of commercially available 2-fluorobenzoyl chloride. The resulting mixture was stirred for 1 h then all volatiles were removed in vacuo. The crude reaction mixture was purified by reverse phase HPLC (TMC Pro-Pac C18; 0-90% 0.1% trifluoroacetic acid in acetonitrile/0.1% trifluoroacetic acid in water gradient) and the pure fractions were lyophilized overnight to afford the title compound as a white solid (0.035 g, 30%). LCMS: m/z (ES) 577 (MH)+.

Step B: 2-Fluoro-N-((1S)-2-{[4-({(2S,5R)-5-[(R)-hydroxy(pyridin-3-yl)methyl]pyrrolidin-2-yl}methyl)phenyl]amino}-1-methyl-2-oxoethyl)benzamide, trifluoracetic acid salt

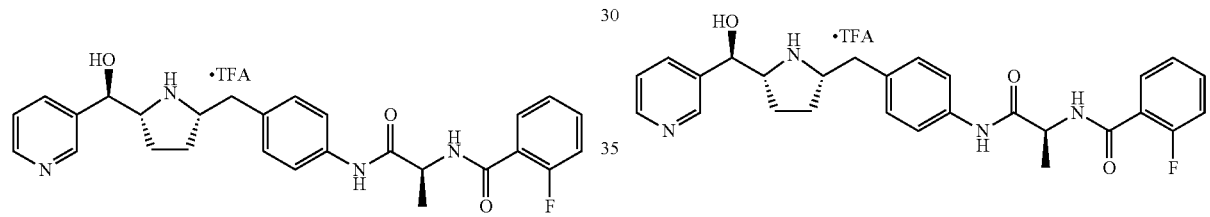

To a stirred solution of 0.033 g (0.057 mmol) of tert-butyl (2S,5R)-2-[4-({(2S)-2-[(2-fluorobenzoyl)amino]propanoyl}amino)benzyl]-5-[(R)-hydroxy(pyridin-3-yl)methyl]pyrrolidine-1-carboxylate, trifluoroacetic acid salt from step A above in 2.5 mL of dichloromethane was added 0.5 mL of trifluoroacetic acid. The resulting mixture was stirred for 1 h then all volatiles were removed in vacuo. The crude reaction mixture was purified by reverse phase HPLC (TMC Pro-Pac C18; 0-70% 0.1% trifluoroacetic acid in acetonitrile/0.1% trifluoroacetic acid in water gradient) and the pure fractions were lyophilized overnight to afford the title compound as a white solid (0.027 g, 67%). LCMS: m/z (ES) 477 (MH)+.

Using the Biological Assays described above, the human β3 functional activity of Example 245 was determined to be less than 1 nM.

EXAMPLE 246

(2S)-2-{[(4-Fluorophenyl)sulfonyl]amino}-N-[4-({(2S,5R)-5-[(R)-hydroxy(pyridin-3-yl)methyl]pyrrolidin-2-yl}methyl)phenyl]propanamide

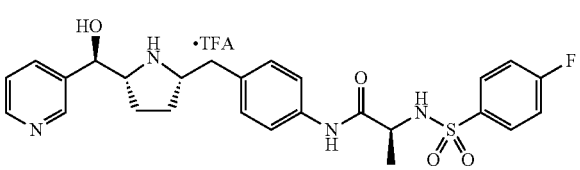 [SMILES: C[C@H](NS(=O)(=O)c1ccc(F)cc1)C(=O)Nc1ccc(C[C@@H]2CC[C@H]([C@H](O)c3cccnc3)N2)cc1]

Step A: Tert-butyl(2S,5R)-2-{4-[((2S)-2-{[(4-fluorophenyl)sulfonyl]amino}propanoyl)amino]benzyl}-5-[(R)-hydroxy(pyridin-3-yl)methyl]pyrrolidine-1-carboxylate, trifluoroacetic acid salt

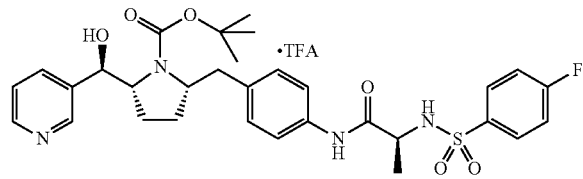 [SMILES: C[C@H](NS(=O)(=O)c1ccc(F)cc1)C(=O)Nc1ccc(C[C@@H]2CC[C@H]([C@H](O)c3cccnc3)N2C(=O)OC(C)(C)C)cc1]

To a solution of 0.085 g (0.19 mmol) of i-72 in 3 mL of dichloromethane was added 0.039 mL (0.28 mmol) of triethylamine followed by 0.036 g (0.19 mmol) of commercially available 4-fluorobenzenesulfonyl chloride. The resulting mixture was stirred for 1 h then all volatiles were removed in vacuo. The crude reaction mixture was purified by reverse phase HPLC (TMC Pro-Pac C18; 0-90% 0.1% trifluoroacetic acid in acetonitrile/0.1% trifluoroacetic acid in water gradient) and the pure fractions were lyophilized overnight to afford the title compound as a white solid (0.047 g, 35%). LCMS: m/z (ES) 613 (MH)+.

Step B: (2S)-2-{[(4-Fluorophenyl)sulfonyl]amino}-N-[4-({(2S,5R)-5-[(R)-hydroxy(pyridin-3-yl)methyl]pyrrolidin-2-yl}methyl)phenyl]propanamide

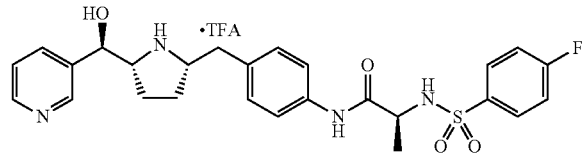 [SMILES: C[C@H](NS(=O)(=O)c1ccc(F)cc1)C(=O)Nc1ccc(C[C@@H]2CC[C@H]([C@H](O)c3cccnc3)N2)cc1]

To a stirred solution of 0.047 g (0.065 mmol) of tert-butyl (2S,5R)-2-{4-[((2S)-2-{[(4-fluorophenyl)sulfonyl]amino}propanoyl)amino]benzyl}-5-[(R)-hydroxy(pyridin-3-yl)methyl]pyrrolidine-1-carboxylate, trifluoroacetic acid salt from step A above in 2.5 mL of dichloromethane was added 0.5 mL of trifluoroacetic acid. The resulting mixture was stirred for 1 h, then all volatiles were removed in vacuo. The crude reaction mixture was purified by reverse phase HPLC (TMC Pro-Pac C18; 0-70% 0.1% trifluoroacetic acid in acetonitrile/0.1% trifluoroacetic acid in water gradient) and the pure fractions were lyophilized overnight to afford the title compound as a white solid (0.030 g, 62%). LCMS: m/z (ES) 513 (MH)+.

Using the Biological Assays described above, the human β3 functional activity of Example 246 was determined to be less than 100 nM.

EXAMPLES 247-261

Following similar procedures outlined above, the examples in the following table were prepared.

Using the Biological Assays described above, the human β3 functional activity of each compound was determined and shown in the following table as the following ranges:

less than 1 nM (+);

1-10 nM (++);

11-100 nM (+++); and 101-1000 nM (++++).

TABLE 6

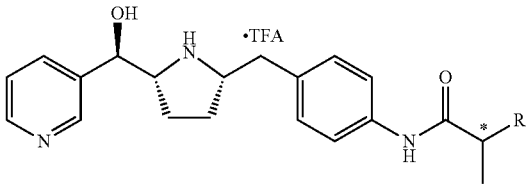

| Example | *Diastereomer | R | MW | MS (MH)+ | Human β3 functional |
|---|---|---|---|---|---|
| 247 | S | ![pyridine-2-carboxamide N-methyl] | 473 | 474 | ++++ |
| 248 | S | ![2-fluorobenzamide N-methyl] | 491 | 491 | +++ |
| 249 | S | ![acetamide] | 396 | 397 | +++ |

TABLE 6-continued
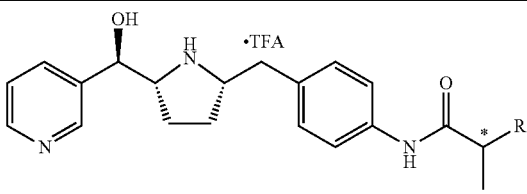
| Example | *Diastereomer | R | MW | MS (MH)+ | Human β3 functional |
|---|---|---|---|---|---|
| 250 | S | 2,6-difluorobenzamide | 494 | 495 | + |
| 251 | S | thiazole-4-carboxamide | 465 | 466 | ++ |
| 252 | S | 1H-1,2,4-triazole-3-carboxamide | 449 | 450 | ++ |
| 253 | S | pyrazine-2-carboxamide | 460 | 461 | +++ |
| 254 | S | NH₂ | 354 | 355 | +++ |
| 255 | S | 2,3-difluorobenzamide | 494 | 495 | + |
| 256 | S | 2-fluorobenzenesulfonamide | 512 | 513 | +++ |
| 257 | S | benzenesulfonamide | 494 | 495 | +++ |
| 258 | S | phenylmethanesulfonamide | 508 | 509 | +++ |

TABLE 6-continued

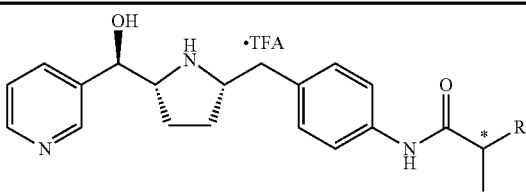

| Example | *Diastereomer | R | MW | MS (MH)+ | Human β3 functional |
|---|---|---|---|---|---|
| 259 | S | 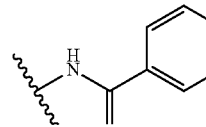 | 476 | 477 | ++ |
| 260 | S | 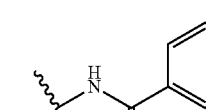 | 458 | 459 | + |
| 261 | R | 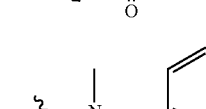 | 490 | 491 | +++ |

EXAMPLE 262

(4R)—N-[4-({(2S,5R)-5-[(R)-(5-fluoropyridin-3-yl)(hydroxy)methyl]pyrrolidin-2-yl}methyl)phenyl]-5,6-dihydro-4H-cyclopenta[d][1,3]thiazole-4-carboxamide, trifluoroacetic acid salt

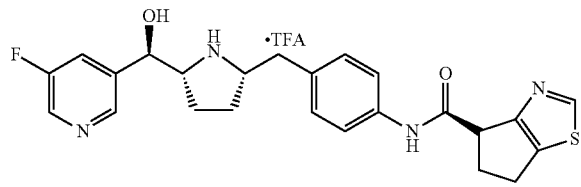

Example 262 was prepared from i-46 and i-48 using a procedure analogous to that used to prepare Example 95. Due to the fact that i-48 is an enantiopure carboxylic acid no chiral separation was needed in the synthesis. $^1$H-NMR (500 MHz, DMSO-$d_6$) δ 10.18 (s, 1 H), 8.91 (s, 1 H), 8.43-8.42 (m, 2H), 7.64-7.61 (m, 2H), 7.52 (d, J=8.5 Hz, 2H), 7.10 (d, J=8.5 Hz, 2H), 4.43 (d, J=6.4 Hz, 1H), 4.06-4.03 (m, 1H), 3.20-3.16 (m, 2H), 3.03-2.97 (m, 1H), 2.91-2.85 (m, 1H), 2.75-2.70 (m, 2H), 2.62 (dd, J=13.3, 6.6 Hz, 1H), 2.53 (dd, J=13.3, 6.8 Hz, 1H), 1.61-1.54 (m, 1H), 1.45-1.33 (m, 2 H), 1.21-1.15 (m, 1H). LC-MS: m/z (ES) 453.4 (MH)+.

Using the Biological Assays described above, the human β3 functional activity of Example 262 was determined to be less than 10 nM.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I, or a pharmaceutically acceptable salt thereof, or a stereoisomer thereof, or a pharmaceutically acceptable salt of the stereoisomer thereof:

I

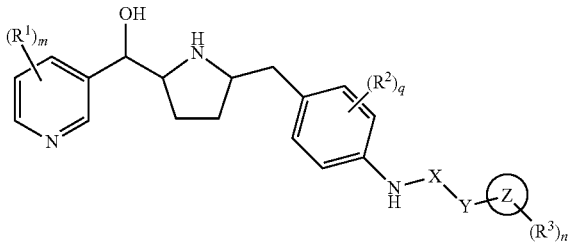

wherein m is 0, 1, 2, 3 or 4;
n is 0, 1, 2, 3, 4 or 5;
p is 0, 1 or 2;
q is 0, 1, 2, 3 or 4;
X is —CO— or —SO$_2$—;

Y is selected from the group consisting of:
(1) $C_1$-$C_5$ alkanediyl, $C_2$-$C_5$ alkenediyl, and $C_2$-$C_5$ alkynediyl, wherein each of alkanediyl, alkenediyl and alkynediyl is optionally substituted with one to three groups independently selected from halogen, $OR^a$, $S(O)_p$—$C_1$-$C_3$ alkyl;
(2) $(CR^aR^a)_j$-Q-$(CR^aR^a)_k$ wherein j and k are integers independently selected from 0, 1 and 2,
(3) a bond, and
(4) phenylene optionally substituted with one to three groups independently selected from $R^1$;

Z is selected from the group consisting of:
thiazolyl, oxazolyl, 1,2,4-triazolyl, 1,2,3-triazolyl, tetrazolyl, pyrrolidinyl, imidazolyl, pyrazolyl, 1,2,4-oxadiazolyl and 1,2,5-oxadiazolyl;

$R^1$ is selected from the group consisting of:
(1) $C_1$-$C_5$ alkyl optionally substituted with 1 to 5 halogen atoms,
(2) $C_3$-$C_6$ cycloalkyl,
(3) halogen,
(4) nitro,
(5) cyano,
(6) —$C(O)R^a$,
(7) —$C(O)_2R^a$,
(8) —$C(O)NR^aR^b$, and
(9) -$QR^b$;

$R^2$ is selected from the group consisting of halogen and $C_1$-$C_5$ alkyl;

$R^3$ is selected from the group consisting of:
(1) $C_1$-$C_6$ alkyl optionally substituted with 1 to 5 groups independently selected from halogen, —$OR^a$ and —$CO_2R^a$ and —$CONR^aR^b$,
(2) —$(CH_2)_t$-phenyl or —$(CH_2)_t$—O-phenyl, wherein t is 0, 1, 2, 3, 4, or 5, and wherein said phenyl in each is optionally substituted with 1 to 3 groups independently selected from halogen, $C_1$-$C_5$ alkyl optionally substituted with 1-5 halogen atoms, and —$OR^a$,
(3) oxo,
(4) thioxo,
(5) halogen,
(6) —CN,
(7) $C_3$-$C_6$ cycloalkyl,
(9) —$OR^a$,
(10) —$C(O)OR^a$,
(11) —$C(O)R^a$,
(12) —$C(O)NR^aR^b$,
(12) —$NR^aR^b$,
(13) —$NR^aC(O)R^b$,
(14) —$NR^aC(O)OR^b$, and
(15) —$NR^aC(O)NR^aR^b$;

$R^a$ is selected from the group consisting of hydrogen and $C_1$-$C_6$ alkyl optionally substituted with 1 to 5 halogen atoms;

$R^b$ is selected from the group consisting of:
(1) hydrogen,
(2) $C_1$-$C_6$ alkyl optionally substituted with 1 to 5 groups selected from
(a) hydroxy,
(b) halogen,
(c) —$CO_2R^a$,
(d) —$S(O)_p$—$C_1$-$C_3$ alkyl,
(e) —$C_3$-$C_8$ cycloalkyl,
(f) $C_1$-$C_6$ alkoxy optionally substituted with 1 to 5 halogens, and
(g) phenyl optionally substituted with 1 to 5 groups independently selected from halogen, nitro, —$NR^aR^a$, trifluoromethyl, trifluoromethoxy, $C_1$-$C_5$ alkyl and —$OR^a$,
(3) $C_3$-$C_8$ cycloalkyl, or
(4) phenyl optionally substituted with 1 to 5 groups selected from
(a) halogen,
(b) nitro,
(c) —$NR^aR^a$,
(d) —OH,
(e) $C_1$-$C_6$ alkoxy optionally substituted with 1 to 5 halogens,
(f) —$S(O)_p$—$C_1$-$C_6$ alkyl, and
(g) $C_1$-$C_6$ alkyl optionally substituted with up to 5 groups selected from hydroxy, halogen, trifluoromethyl, cyano, —$CO_2R^a$, $C_3$-$C_8$ cycloalkyl, and -$QR^c$;

$R^c$ is selected from the group consisting of:
(1) Z optionally substituted with up to 5 groups selected from halogen, trifluoromethyl, cyano, $C_1$-$C_5$ alkyl and $C_1$-$C_5$ alkoxy, and
(2) $C_1$-$C_6$ alkyl;

Q is selected from the group consisting of:
(1) —$N(R^a)$—,
(2) —O—, and
(3) —$S(O)_p$—.

2. The compound of claim 1 wherein Y is methylene, —$CH(CH_3)$— or a bond.

3. The compound of claim 1 of Formula Ia, or a pharmaceutically acceptable salt thereof, or a stereoisomer thereof, or a pharmaceutically acceptable salt of the stereoisomer thereof:

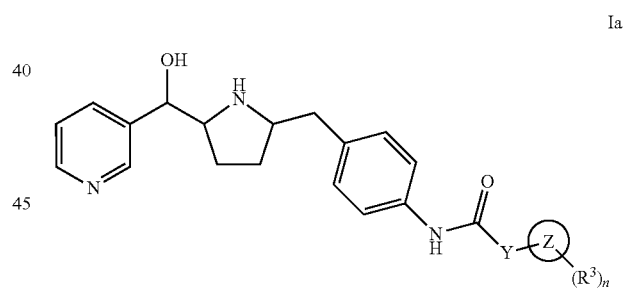

Ia wherein Y, Z, $R^3$ and n are as defined in claim 1.

4. The compound of claim 3 wherein Y is methylene, —$CH(CH_3)$—or a bond.

5. The compound of claim 3 wherein $R^3$ is selected from the group consisting of:
(1) $C_1$-$C_6$ alkyl optionally substituted with halogen or —$OR^a$,
(2) oxo,
(3) halogen,
(4) —$OR^a$,
(5) —$C(O)NR^aR^a$, and
(6) —$NR^aR^a$,
wherein $R^a$ is as defined in claim 3.

6. A compound of Formula Ia, or a pharmaceutically acceptable salt thereof, or a stereoisomer thereof, or a pharmaceutically acceptable salt of the stereoisomer thereof:

Ia

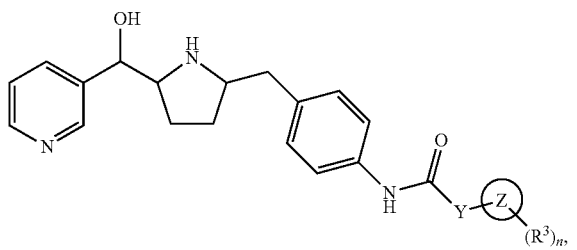

wherein n is 0, 1 or 2;

Y is selected from the group consisting of methylene, —CH(CH₃)— and a bond;

Z is selected from the group consisting of thiazolyl, 1,2,4-triazolyl, and pyrazolyl, and R³ is selected from the group consisting of:
(1) methyl,
(2) oxo, and
(3) —NH₂.

7. A pharmaceutical composition comprising a compound of claim 1 and a pharmaceutically acceptable carrier.

8. A compound or a pharmaceutically acceptable salt thereof, or a stereoisomer thereof, or a pharmaceutically acceptable salt of the stereoisomer thereof selected from:

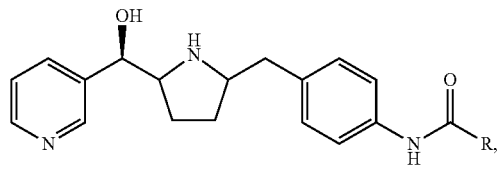

wherein R is selected from:

| R |
|---|
| 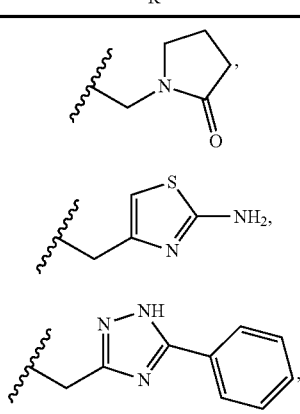 |
| 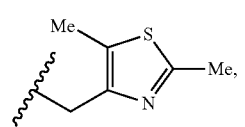 [SMILES: *Cc1nc(C)sc1C] |

-continued

| R |
|---|
| 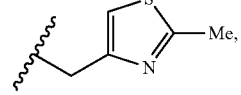 |
| 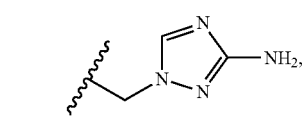 [SMILES: *Cn1cnc(N)n1] |
| 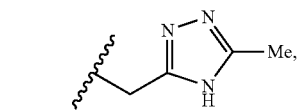 |
| 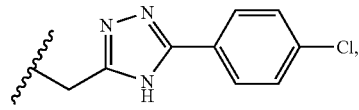 [SMILES: *Cc1nnc(-c2ccc(Cl)cc2)[nH]1] |
| 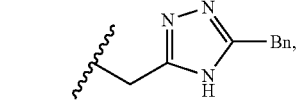 [SMILES: *Cc1nnc(Cc2ccccc2)[nH]1] |
| 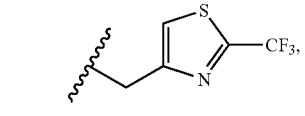 [SMILES: *Cc1csc(C(F)(F)F)n1] |
| 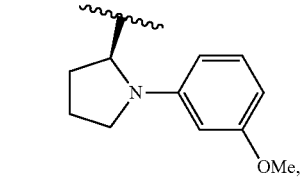 [SMILES: *[C@@H]1CCCN1c1cccc(OC)c1] |
| 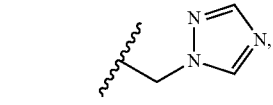 [SMILES: *Cn1cncn1] |
| 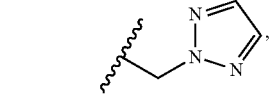 |
| 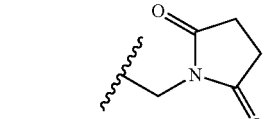 |
| 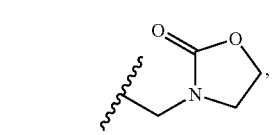 [SMILES: *CN1CCOC1=O] |

| 161 -continued | 162 -continued |
|---|---|
| R | R |
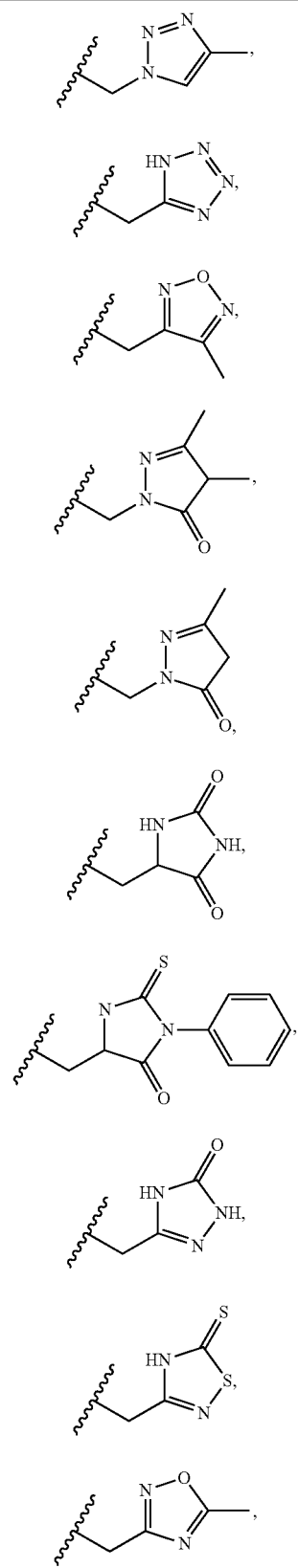
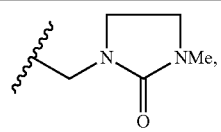
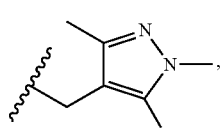
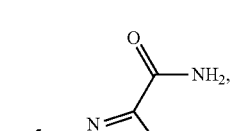
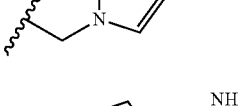
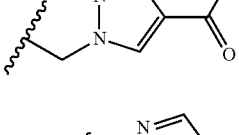
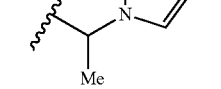
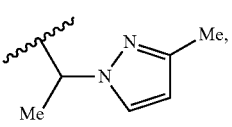 [SMILES: *C(C)n1ccc(C)n1]
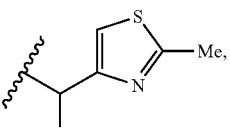
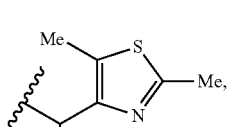
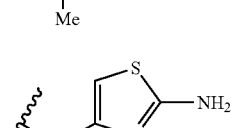
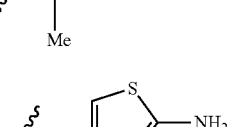
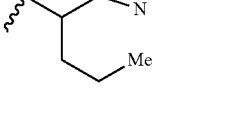

-continued
| R | R |
|---|---|
| 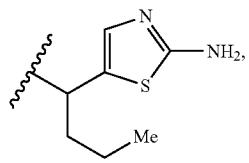 [SMILES: *C(CCC)c1cnc(N)s1] | 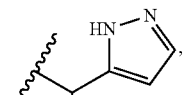 |
| 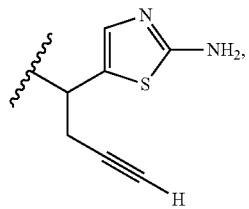 [SMILES: *C(CC#C)c1cnc(N)s1] | 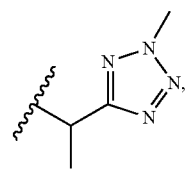 |
| 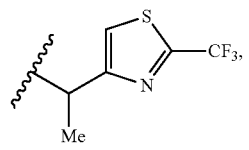 [SMILES: *C(C)c1csc(C(F)(F)F)n1] | 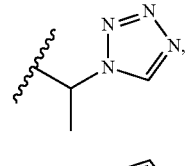 |
| 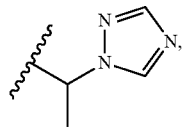 [SMILES: *C(C)n1cncn1] | 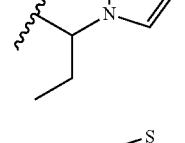 |
| 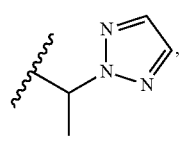 [SMILES: *C(C)n1nccn1] | 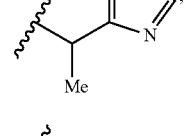 |
| 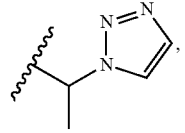 [SMILES: *C(C)n1ccnn1] | 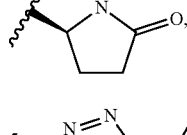 |
| 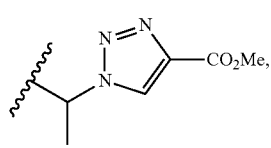 [SMILES: *C(C)n1cc(C(=O)OC)nn1] | 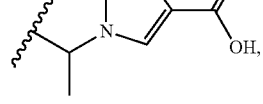 |
| 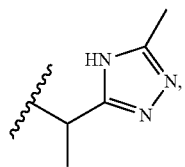 [SMILES: *C(C)c1nnc(C)[nH]1] | 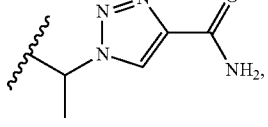 |
| 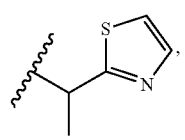 [SMILES: *C(C)c1nccs1] | 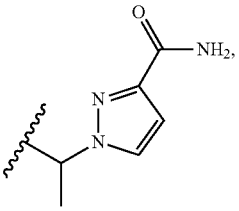 |
| 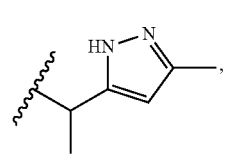 [SMILES: *C(C)c1cc(C)n[nH]1] | 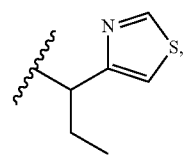 [SMILES: *C(CC)c1cscn1] |

| R |
|---|
| 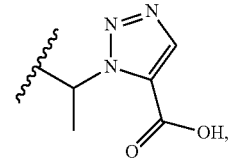 [SMILES: *C(C)n1nncc1C(=O)O] |
| 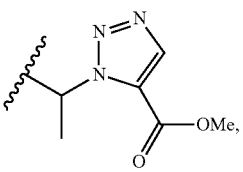 [SMILES: *C(C)n1nncc1C(=O)OC] |
| 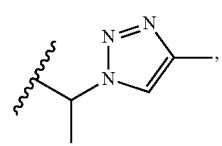 |
| 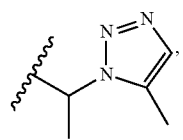 [SMILES: *C(C)n1nncc1C] |
| R |
|---|
| 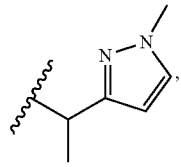 [SMILES: *C(C)c1ccn(C)n1] |
| 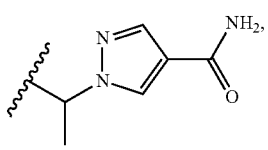 [SMILES: *C(C)n1cc(C(N)=O)cn1] |
| 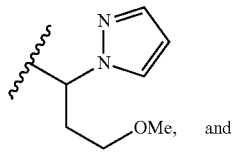 [SMILES: *C(CCOC)n1cccn1 ; "and"] and |
| 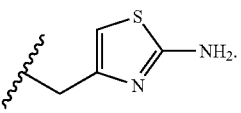 [SMILES: *Cc1csc(N)n1] |
* * * * *